(12) United States Patent
Pathak et al.

(10) Patent No.: US 7,919,112 B2
(45) Date of Patent: Apr. 5, 2011

(54) IMPLANTABLE TISSUE COMPOSITIONS AND METHOD

(75) Inventors: Chandraskekhar P. Pathak, Phoenix, AZ (US); Sanjay M. Thigle, Maharashtra (IN)

(73) Assignee: Pathak Holdings, LLC, Phoenix, AZ (US)

( * ) Notice: Subject to any disclaimer, the term of this patent is extended or adjusted under 35 U.S.C. 154(b) by 800 days.

(21) Appl. No.: 11/661,062

(22) PCT Filed: Aug. 24, 2005

(86) PCT No.: PCT/US2005/030187
§ 371 (c)(1),
(2), (4) Date: Feb. 22, 2007

(87) PCT Pub. No.: WO2006/026325
PCT Pub. Date: Mar. 9, 2006

(65) Prior Publication Data
US 2007/0254005 A1    Nov. 1, 2007
US 2009/0130162 A2    May 21, 2009

Related U.S. Application Data

(60) Provisional application No. 60/604,737, filed on Aug. 26, 2004.

(51) Int. Cl.
A61F 2/00 (2006.01)
(52) U.S. Cl. .............................. 424/426; 424/423; 514/2
(58) Field of Classification Search ................ 424/426, 424/423; 514/2
See application file for complete search history.

(56) References Cited

U.S. PATENT DOCUMENTS

| | | |
|---|---|---|
| 3,640,741 A | 2/1972 | Etes |
| 3,779,942 A | 12/1973 | Bolles |
| 3,846,382 A * | 11/1974 | Ramsey et al. ............... 428/402 |
| 3,949,068 A | 4/1976 | Polin |
| 4,268,495 A | 5/1981 | Muxfeldt et al. |
| 4,481,009 A | 11/1984 | Nashef |
| 4,490,497 A | 12/1984 | Evrard et al. |
| 4,631,188 A | 12/1986 | Stoy et al. |
| 4,740,534 A | 4/1988 | Matsuda et al. |
| 4,755,593 A * | 7/1988 | Lauren ........................... 530/356 |
| 4,938,763 A | 7/1990 | Dunn et al. |
| 5,002,794 A * | 3/1991 | Ratner et al. ................... 427/488 |
| 5,213,808 A | 5/1993 | Bar-Shalom et al. |
| 5,399,351 A | 3/1995 | Leshchiner et al. |
| 5,410,016 A | 4/1995 | Hubbell et al. |
| 5,480,914 A | 1/1996 | Meadows |
| 5,514,379 A | 5/1996 | Weissleder et al. |
| 5,514,380 A | 5/1996 | Song et al. |
| 5,529,914 A | 6/1996 | Hubbell et al. |
| 5,583,114 A | 12/1996 | Barrows et al. |
| 5,612,052 A | 3/1997 | Shalaby |
| 5,618,563 A | 4/1997 | Berde et al. |
| 5,645,583 A | 7/1997 | Villain et al. |
| 5,741,323 A | 4/1998 | Pathak et al. |
| 5,814,621 A | 9/1998 | Kanaya et al. |
| 5,844,016 A | 12/1998 | Sawhney et al. |
| 5,849,035 A | 12/1998 | Pathak et al. |
| 5,879,688 A | 3/1999 | Coury et al. |
| 5,993,972 A * | 11/1999 | Reich et al. ................. 428/423.1 |
| 6,132,986 A | 10/2000 | Pathak et al. |
| 6,156,345 A | 12/2000 | Chudzik et al. |
| 6,156,531 A | 12/2000 | Pathak et al. |
| 6,176,871 B1 | 1/2001 | Pathak et al. |
| 6,177,514 B1 | 1/2001 | Pathak et al. |
| 6,261,544 B1 | 7/2001 | Coury et al. |
| 6,322,593 B1 | 11/2001 | Pathak et al. |
| 6,465,001 B1 | 10/2002 | Hubbell et al. |
| 6,479,079 B1 | 11/2002 | Pathak et al. |
| 6,528,107 B2 | 3/2003 | Chinn et al. |
| 6,566,406 B1 | 5/2003 | Pathak et al. |
| 6,596,471 B2 | 7/2003 | Pathak et al. |
| 6,632,446 B1 | 10/2003 | Hubbell et al. |
| 6,713,646 B2 | 3/2004 | Zhang et al. |
| 6,887,974 B2 | 5/2005 | Pathak |
| 7,129,210 B2 | 10/2006 | Lowinger et al. |
| 7,153,519 B2 | 12/2006 | Hubbell et al. |
| 7,211,651 B2 | 5/2007 | Pathak |
| 7,323,189 B2 | 1/2008 | Pathak |
| 7,413,781 B2 | 8/2008 | Hubbell et al. |
| 7,476,246 B2 | 1/2009 | Pathak |
| 7,592,418 B2 | 9/2009 | Pathak et al. |
| 7,597,882 B2 | 10/2009 | Pathak et al. |

(Continued)

FOREIGN PATENT DOCUMENTS

WO    94/24962 A1    11/1994

(Continued)

OTHER PUBLICATIONS

Levy et al. J. Controlled Release (1990) 11(1-3): 245-54. abstract only; downloaded from file CAPLUS on STN Jan. 30, 2010.*

*Primary Examiner* — Sandra Saucier
*Assistant Examiner* — Susan Hanley
(74) *Attorney, Agent, or Firm* — Dardi & Herbert, PLLC

(57) ABSTRACT

Novel implantable tissue fixation methods and compositions are disclosed. Methods and compositions of tissue, fixed using polymeric and/or variable length crosslinks, and di- or polymercapto compounds are described. Also described are the methods and compositions wherein the tissue is fixed using biodegradable crosslinkers. Methods and compositions for making radio-opaque tissue are also described. Methods and compositions to obtain a degradable implantable tissue-synthetic biodegradable polymer composite are also described. Compositions and methods of incorporating substantially water-insoluble bioactive compounds in the implantable tissue are also disclosed. The use of membrane-like implantable tissue to make an implantable drug delivery patch are also disclosed. Also described are the compositions and methods to obtain a coated implantable tissue. Medical applications implantable tissue such as heart valve bioprosthesis, vascular grafts, meniscus implant, drug delivery patch are also disclosed.

14 Claims, 11 Drawing Sheets

U.S. PATENT DOCUMENTS

| | | |
|---|---|---|
| 2001/0025196 A1* | 9/2001 | Chinn et al. .................. 623/2.17 |
| 2002/0111532 A1 | 8/2002 | Pathak et al. |
| 2002/0119563 A1 | 8/2002 | Pathak et al. |
| 2002/0120328 A1 | 8/2002 | Pathak et al. |
| 2002/0127266 A1 | 9/2002 | Sawhney et al. |
| 2002/0127719 A1* | 9/2002 | Stone ........................... 435/378 |
| 2002/0198590 A1* | 12/2002 | Ung-Chhun ................. 623/1.15 |
| 2003/0077310 A1 | 4/2003 | Pathak et al. |
| 2004/0002456 A1 | 1/2004 | Pathak |
| 2004/0013626 A1* | 1/2004 | Gref et al. .................. 424/70.13 |
| 2005/0106724 A1* | 5/2005 | Schierholz et al. ............ 435/366 |
| 2005/0169882 A1 | 8/2005 | Lowe et al. |
| 2005/0209705 A1* | 9/2005 | Niederauer et al. ....... 623/23.63 |
| 2006/0165752 A1 | 7/2006 | Pathak et al. |
| 2007/0003525 A1 | 1/2007 | Moehlenbruck et al. |

FOREIGN PATENT DOCUMENTS

| | | |
|---|---|---|
| WO | WO 98/12274 | 3/1998 |
| WO | 02/00274 A1 | 1/2002 |
| WO | 02/07785 A2 | 1/2002 |
| WO | 2004/069296 A1 | 8/2004 |
| WO | 2006/026325 A2 | 3/2006 |
| WO | 2006/133373 A2 | 12/2006 |
| WO | 2007/030512 A2 | 3/2007 |
| WO | 2007/056761 A2 | 5/2007 |
| WO | 2008/073965 A2 | 6/2008 |
| WO | 2008/076973 A2 | 6/2008 |

* cited by examiner

IMPLANTABLE TISSUE COMPOSITIONS AND METHOD

CROSS-REFERENCE TO RELATED APPLICATIONS

This application is a national stage entry of PCT/US05/30187, filed Aug. 24, 2005, which claims benefit of priority to U.S. provisional application No. 60/604,737, filed Aug. 26, 2004, the contents of which are incorporated by reference.

FIELD OF THE INVENTION

The present invention relates to methods and compositions for the preparation of biological tissues or extracellular matrices and their medical applications.

BACKGROUND OF THE INVENTION

The use of human or animal tissue for medical or surgical use is a rapidly growing therapeutic field. Many uses of processed biological tissues for implantation into humans have been reported. The commercial products or products under development include wound healing dressings, tissue heart valves, ligament substitutes, pericardial patches and membranes, vascular grafts and the like. The use of animal tissue offers an inexpensive source of materials to fabricate tissue-based medical products. The problems with the animal tissue transplantation include inflammation, unwanted degradation, control over the degradation process, calcification, inability to release bioactive compounds in a controlled manner, and rejection of the transplanted tissue.

The primary component of many biological tissues is a protein called collagen. Collagen-based biomaterials generally induce a mild inflammatory response, which results in degradation of the protein. This degradation can be prevented by chemical modification or crosslinking of tissue proteins and is achieved by reacting difunctional and polyfunctional crosslinkers capable of forming irreversible and stable intermolecular chemical crosslinking between two collagen chains. Chemical crosslinking may also increase strength and durability of the tissue. Many heart valve bioprosthesis manufacturers use glutaraldehyde as a crosslinking agent for stabilization of the bioprosthesis tissue. The chemistry of glutaraldehyde is complex but well documented. Glutaraldehyde reacts with free amine groups from lysine residues on collagen and forms Schiff base addition products. Although glutaraldehyde is the most commonly used chemical fixative for biological tissues, there are a number of drawbacks associated with its use in the production of bioprosthetic devices. For example, the long term durability of glutaraldehyde-fixed bioprostheses is not well established. Another drawback to glutaraldehyde fixation of bioprostheses relates to the release of cytotoxic glutaraldehyde on the tissue surface thereby hindering the growth of cells, especially endothelial cells, on the surface of the tissue. Glutaraldehyde fixed tissue is also susceptible to calcification which leads to device failure.

To overcome limitations of glutaraldehyde crosslinking, other chemical crosslinking agents capable of reacting with amine, carboxyl and hydroxyl group have been explored. Tissue crosslinking chemistry has been recently reviewed. However, none of alternative chemistries have resulted into a commercial clinical heart valve product. Tissue crosslinking chemistry is challenging due to a variety of reasons. From the chemistry point of view, the crosslinking reaction is a heterogeneous reaction, where the reactant (tissue) is always in a separate phase (solid state phase) as compared to the crosslinker (solution, oiled or liquid phase). This limits the accessibility of tissue functional groups for crosslinking reaction. The solid state nature of tissue also makes it difficult for large crosslinker molecules such as, by way of example, and not limitation, polymers to penetrate inside the tissue matrix and crosslink the reactive sites. Generally, the crosslinking reaction must be done without denaturing the protein. The denatured tissue/collagen (gelatin) is more susceptible to enzymatic degradation and denatured proteins have inferior mechanical properties as compared to non-denatured tissue. To prevent denaturing of tissue, the use of aggressive organic solvents and high temperatures in tissue crosslinking is generally avoided. It is generally believed that an aqueous medium with physiological conditions (pH 7.2, 37° C.) is best suited for tissue crosslinking. Fixation under physiological conditions is most likely to preserve the natural conformation of proteins present in the tissue. Glutaraldehyde is one of the few crosslinking agents capable of reacting with the tissue in water under physiological conditions.

In known approaches, most of the tissue crosslinking is restricted to di- or polyfunctional small compounds such as, by way of example, and not limitation, glutaraldehyde. Small compounds can easily penetrate solid tissue matrix and can crosslink surface as well as bulk components of the tissue matrix. In order for crosslinking to occur, two or more reactive functional groups must react with two polymeric chains to form an interchain crosslinked moiety. Most tissue crosslinkers are single chemical entities and therefore have fixed molecular length. The fixed length crosslinker can only react with those sites which are within the close proximity of its reactive functional groups. Therefore, it cannot crosslink the tissue if the reactive sites present on the tissue are at a shorter or longer distance than the length of crosslinker. Also, during the crosslinking reaction, one of the crosslinking functional group reacts with the crosslinkable moiety such as, by way of example, and not limitation, collagen. After the reaction, the other functional group must react with other reactive site on the collagen to complete the crosslinking reaction. This often may not be possible due to limited length and mobility of crosslinker. This results in a number of dangling bonds with incomplete crosslinking. Therefore, the length of a crosslinker serves as a major limitation in achieving a high degree of crosslinking. Thus, there is a need for tissue crosslinking methods wherein the crosslinks formed may have variable lengths.

Polymeric crosslinkers can be useful in crosslinking the tissue due to high molecular flexibility of polymeric molecular coil and polymer's ability to impart additional properties to the tissue matrix. However, polymeric crosslinkers are large molecules which cannot diffuse/penetrate inside the tissue matrix and react with sites present in the bulk of the tissue. This limits the ability of polymeric crosslinker to surface crosslinking only. Known techniques generally do not teach the successful use of polymeric crosslinkers in tissue crosslinking. There is a need for methods and compositions that permit the incorporation and crosslinking of tissue using polymers or that generate polymeric crosslinks.

Shape memory biomaterials have the ability to change to a predetermined shape when subjected to an appropriate energy stimulus. Nitinol alloy is one of the well-known shape memory biomaterials. Many applications of Nitinol materials have been commercialized. These applications include peripheral vascular stent and stent grafts, vena cava filters, etc. Bioprosthetic tissues having shape memory properties can be extremely useful in making novel medical devices. There is a need for tissue-based biomaterials that can remember shape maintained during fixation or stabilization and tissue-based materials with the ability to remember and recover the shape when deformed by a mechanical force.

Unfixed or non-crosslinked animal tissue undergoes enzymatic degradation when implanted in human/animal body. Usually such degradation is followed after a moderate to severe inflammatory response; presumably due to an immunological reaction to the foreign biological materials in the host body. Non-crosslinked animal tissue such as, by way of example, and not limitation, porcine small-intestinal submucosa has been commercialized as a wound dressing material. In many medical applications, it is desirable to have a biological degradable tissue with no or little inflammatory response and control over its degradation profile and properties. Known techniques generally do not teach methods and compositions that will affect the degradation behavior of biological tissue. Therefore, there is also a need for methods and compositions that can reduce the inflammatory response to the animal or human tissue. Compositions and methods that will control the degradation time of the implanted tissue are also needed.

Animal tissue used in commercial bioprostheses such as heart valve, vascular graft and vascular patch is limited by tissue thickness, size and protein (chemical) composition. For example, bovine pericardium, a widely used animal tissue has a thickness ranging 1 to 2 mm which may too thick for some medical applications such as low profile stent graft application. The useful tissue recovered from one animal is also limited in size. Typical area of bovine pericardial or porcine pericardial tissue may range from 50 to 150 square inches. This size and thickness limitation may limit the use of tissue in making large medical device such as tissue based dialysis catheters. The tissue size limits also increases production costs due to lower yields. The higher size of implantable tissue may permit to manufacture more devices per tissue and reduce manufacturing costs. Therefore there is need for tissue, especially membrane like tissue, which can be made in wide ranges of size, thickness and with different chemical compositions for bioprosthesis applications.

Synthetic biodegradable polymers have received considerable interest in the medical and pharmaceutical field at least because they can perform temporary therapeutic functions and are eliminated from the body once their therapeutic function has been accomplished. Some of the well-known applications of biodegradable polymers include surgical sutures, staples, or other wound closure devices, as a carrier for bioactive substances for controlled drug delivery, etc. Several types of biodegradable polymers have been reported in the subject literature, however, polymers prepared from hydroxy acids have received much attention due to their degradability and toxicological safety. Homopolymers and copolymers based on the I-lactic acid, dl-lactic acid and glycolic acid are among the most widely used polymers for medical applications. These polymers can be formulated into variety of physical forms such as, by way of example, and not limitation, fibers or filaments with acceptable mechanical properties and degradation profile and nontoxic degradation products. Synthetic biodegradable polymers such as, by way of example, and not limitation, polyanhydrides, polylactones, and polyhydroxyacids have been extensively investigated for controlled drug delivery applications as well as for a scaffold for tissue engineering. These polymers can release a bioactive compound upon bioerosion and thus permit localized controlled therapeutic delivery. There is a need for biological tissue, preferably degradable biological tissue, which can release a bioactive compound in a controlled manner, preferably using a hydrolysis or bioerosion mechanism. There is also a need for materials which can provide properties of synthetic biodegradable material and biological tissues.

Polyethylene oxide (PEO) or polyethylene glycol (PEG) is a water soluble biocompatible polymer which is being used in several commercially available pharmaceutical and medical products. PEG is water soluble and non-ionic in nature. When injected in human or animal body, it is rapidly cleared by the body. When it is immobilized either physically or chemically on a polymer surface, it renders the surface highly resistant to protein adsorption. The resistance to protein adsorption is believed to be responsible for reduced bacterial and cell adhesion to PEG-rich surfaces. The reduction in protein adsorption also increases the biocompatibility of blood- and tissue-contacting materials. Hydrated PEG chain is not recognized by the immune system, therefore it is used to reduce the immunogenicity and antigenicity of proteins and hence increase their circulation time. Nonionic hydrogels, such as, by way of example, and not limitation, the poly(ethylene glycol) (PEG)-based hydrogels, are biocompatible and are non-cell adhesive. Tissue-based bioprostheses which combine the properties of PEG and biological tissue may be useful for many medical applications.

In view of the foregoing, there is a need for compositions and methods that provide biostable implantable tissue. There is also a need for biodegradable biological tissue with control over its degradation time and with the ability to release bioactive compounds.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
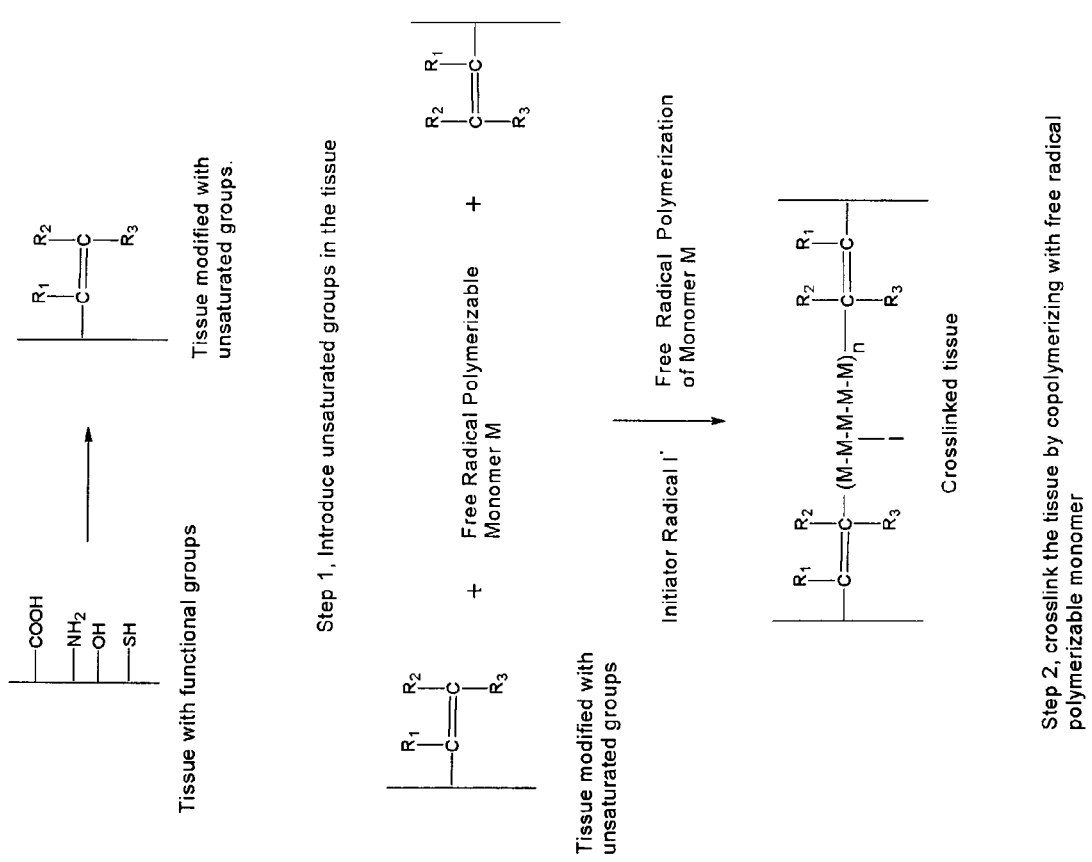
FIG. 1 is a schematic representation of exemplary steps involved in tissue crosslinking by free radical polymerization, in accordance with an embodiment of the present invention.

Unless otherwise indicated illustrations in the figures are not necessarily drawn to scale.

SUMMARY OF THE INVENTION

To achieve the forgoing and other objects and in accordance with the purpose of the invention, a variety of implantable tissue compositions and methods thereof are described.

One embodiment of the present invention provides a composition of matter, comprising an uncrosslinked biological tissue, wherein the tissue is chemically modified with unsaturated polymerizable groups Another embodiment of the present invention provides a composition of matter comprising a biological tissue modified with unsaturated groups, wherein unsaturated groups are used in chemical crosslinking of the tissue.

Another embodiment of the present invention provides a composition of matter comprising a biological tissue modified with unsaturated groups, wherein the cross-linked biological tissue is produced by treating the tissue under effective cross-linking condition comprising a free radical initiator or photoinitiator. Preferably the crosslinking is done in presence of a mono or polyunsaturated compound capable of copolymerizing with the unsaturated groups in the tissue.

Another embodiment of the present invention provides a composition of matter comprising a biological tissue modified with unsaturated groups, wherein unsaturated groups are copolymerized with free radical polymerizable comonomers. The comonomers may include functional monomers with reactive functional groups such as epoxide or isocyanate; monomers with charged groups; monomers that undergo crosslinking and biodegradation; monomers that produce thermosensitive polymers; monomers with long alkyl chains; monomers that produce crystalline or semicrystalline polymers; monomers that produce functional polymers upon hydrolysis such as polyvinyl alcohol and monomers that have radio-opaque moieties.

Another embodiment of the present invention provides a composition of matter comprising a biological tissue modified and crosslinked with unsaturated groups, wherein unsaturated modified groups and/or crosslinks with unsaturated groups are copolymerized with free radical polymerizable comonomers.

Another embodiment of the present invention provides a composition of matter comprising a biological tissue modified with unsaturated groups, wherein unsaturated groups are copolymerized with free radical polymerizable comonomers that have biodegradable or hydrolizable groups. The biodegradable monomers may be hydrophilic or hydrophobic.

Another embodiment of the present invention provides a composition of matter comprising a biological tissue modified with unsaturated groups, wherein a cross-linked biological tissue is produced by treating the unsaturated groups modified tissue under effective cross-linking conditions with an organic di or poly-mercapto compounds. Preferably, the di or poly-mercapto organic compound is a solute in a fluid comprising a solvent.

Another embodiment of the present invention provides a composition of matter comprising a membrane like biological tissue and a surgical adhesive. The membrane like tissue and surgical adhesive are formulated to form a "surgical adhesive patch". The surgical adhesive patch could be biodegradable.

Yet another embodiment of the present invention relates to a cross-linked biological tissue produced by treating the tissue under effective cross-linking conditions with a biodegradable crosslinker. Preferably, the biodegradable crosslinker is a solute in a fluid comprising a solvent.

Yet another embodiment of the present invention provides a composition comprising a radio-opaque implantable animal tissue.

Yet another embodiment of the present invention relates to a biological tissue having shape memory properties.

Yet another embodiment of the present invention relates to a biological tissue wherein certain parts or regions of the tissue are made biostable while the remaining parts of the tissue are made biodegradable. The biostable and biodegradable regions with in the tissue can be of any geometry.

Yet another embodiment of the present invention relates to a non-crosslinked degradable biological tissue produced by treating the tissue under effective treatment conditions with a monofunctional regent capable of reacting with primary amine groups on the tissue. Preferably, the monofunctional reagent is: a polyether derivative or an activated acid derivative such as n-hydroxysuccinimide derivative, or a cyclic lactide such as glycolide or lactide or an isocyanate derivative or an anhydride derivative.

Yet another embodiment of the present invention relates to the substantially biostable or biodegradable tissue produced by treating the tissue under effective treatment conditions with a cyclic lactone to produce a tissue-polylactone graft copolymer.

Yet another embodiment of the present invention relates to a biological tissue/synthetic biodegradable polymer composite produced by treating the tissue with a fluid comprising synthetic biodegradable polymer.

Yet another embodiment of the present invention relates to a biological tissue synthetic biodegradable polymer composite wherein synthetic biodegradable polymer is chemically bonded to the biological tissue.

Another embodiment of the present invention relates to a degradable biological tissue-synthetic biodegradable polymer composite produced by treating a non-crosslinked tissue under effective treatment conditions with a synthetic biodegradable polymer. Preferably, the synthetic biodegradable polymer is polylactone or polyhydroxyacid derivative in a fluid comprising a solvent. The synthetic biodegradable polymer can also be a crosslinked polymer.

Yet another embodiment of the present invention relates to a biological tissue produced by treating the tissue with a fluid comprising synthetic biodegradable polymer and a bioactive compound.

Yet another embodiment of the present invention provides a composition of matter that promotes the localized controlled delivery of at least one drug.

Yet another embodiment of the present invention provides an animal tissue based controlled drug delivery patch that releases at least one bioactive compound.

Yet another embodiment of the present invention relates to a method of cross-linking a tissue is provided. The method comprises: linking the free radical polymerizable groups on the tissue with a covalent bond; crosslinking the free radical polymerizable groups using free radical mechanism or cyclic dimerization.

Yet another embodiment of the present invention relates to a method of cross-linking a tissue is provided. The method comprises: covalently linking the compounds containing at least one free radical polymerizable group on the tissue; crosslinking the free radical polymerizable group using a di or poly-mercapto organic compounds.

Yet another embodiment of the present invention relates to a method of cross-linking a tissue is provided. The method comprises: crosslinking the tissue with compounds containing at least one free radical polymerizable group; further crosslinking the free radical polymerizable group using free radical chemistry such as free radical dimerization and polymerization, free radical crosslinking or free radical copolymerization with monomer.

In still another embodiment of the present invention, a method for making a biodegradable biological tissue is provided. The method comprises: treating the tissue under effective cross-linking conditions with a fluid comprising a biodegradable crosslinker.

In still another embodiment of the present invention, a method for incorporating a biodegradable polymer in a biological tissue is provided. The method comprises: dehydrating the biological tissue; treating the dehydrated tissue with a solution of biodegradable polymer in an organic solvent; removing the solvent from the treated tissue.

In still another embodiment of the present invention, a method for incorporating a biodegradable polymer and a bioactive compound in a biological tissue is provided. The method comprises: dehydrating the biological tissue; treating dehydrated tissue with a solution of biodegradable polymer and bioactive compound in an organic solvent; removing the solvent from the treated tissue.

In still another embodiment of the present invention, a method for making a drug delivery patch from a membrane like tissue is provided. The method comprises: dehydrating the membrane like biological tissue; treating dehydrated membrane like tissue with a solution of biodegradable polymer and a bioactive compound in an organic solvent; removing the solvent from the treated tissue; releasing the compound from the biodegradable polymer. Preferably the bioactive compound is a cell cycle inhibitor such as Lovastatin (HMG-CoA inhibitor or statin), paclitaxel, and Rapamycin. The biodegradable polymer may be hydrophobic or hydrophilic. The biodegradable polymer can be a crosslinked polymer.

In still another embodiment of the present invention, a method of coating a biological tissue with biodegradable polymer is provided. The method comprises: dehydrating the biological tissue; spraying a coating solution comprising biodegradable polymer in a solvent; removing the solvent from the treated tissue.

In still another embodiment of the present invention, a method of coating a biological tissue with biodegradable polymer is provided. The method comprises: dehydrating the biological tissue; dipping the dehydrated tissue in a coating solution comprising biodegradable polymer in a solvent; removing the solvent from the treated tissue.

In still another embodiment of the present invention, a method for making a radio-opaque implantable tissue is provided. The method comprises: treating a biological tissue with a radio-opaque compound under effective treatment conditions to covalently bond the radio-opaque compound to the tissue. The preferred radio-opaque compound is iodinated organic compound.

In still another embodiment of the present invention, a method treating the tissue under effective cross-linking conditions with a di or polymercapto organic compound is provided.

In still another embodiment of the present invention, a method of coating a biological implantable tissue with a biodegradable hydrogel is provided. The method comprises: treating a tissue with a precursor or biodegradable hydrogel components; crosslinking the precursors to produce a biodegradable hydrogel coating on the surface of the tissue.

In still another embodiment of the present invention, a method of coating a biological implantable tissue with biodegradable hydrogel comprising cells/bioactive compound is provided. The method comprises: treating a tissue with a precursor or biodegradable hydrogel components comprising cells and/or bioactive compounds; crosslinking the precursors to produce a biodegradable hydrogel coating with entrapped cells/drug in the coating on the surface of the tissue.

In still another embodiment of the present invention, a method of coating a biological tissue with non-crosslinked biodegradable hydrogel is provided. The method comprises: dehydrating the biological tissue; treating the dehydrated tissue with a solution of biodegradable polymer in an organic solvent; removing the solvent from the treated tissue; exposing the tissue to a biological environment to hydrate the tissue and biodegradable polymer.

In still another embodiment of the present invention, a method for incorporating a biodegradable polymer and bioactive substance in biological tissue is provided. The method comprises; forming groves or holes on tissue surface; filling the grooves or holes with a biodegradable polymer and bioactive compound; releasing the bioactive compound in a controlled manner.

Another embodiment of the present invention provides a degradable animal tissue coated with or incorporated with, Demineralized Bone Matrix (DBM) and/or purified Bone Marrow Proteins (BMP)'s. This mixture provides a matrix that allows the cellular components of the body to migrate into it and thus produce osteoinduction where needed. The matrix composition, enzymes (such as thrombin and plasmin), BMPs, growth factors and DBM and their concentrations, calcium salts such as calcium phosphates are adequately formulated to optimize the longevity of this temporal scaffolding structure and the osteoinduction which needs to occur. All of the animal tissue components are biodegradable, but during osteogenesis the mixture provides a non-collapsible scaffold that can determine the shape and location of the newly formed bone.

Another embodiment of the present invention provides a composition of matter comprising a degradable tissue coated with a biodegradable polymer comprising at least one growth factor and/or a drug.

Yet another embodiment of the present invention provides a composition of matter that promotes wound healing, comprising: a biodegradable implantable animal tissue coated with biodegradable polymer and an effective concentration of at least one growth factor, wherein the concentration of growth factor is effective in promoting wound healing.

Another embodiment of the present invention provides a composition of matter that promotes the growth of cells, comprising: a degradable animal tissue; a hydrogel coating on the surface of degradable tissue; and an effective concentration of at least one growth factor, wherein the concentration of the growth factor is effective in promoting the directed migration of the animal cells. In another embodiment, genetically altered cells and/or other cells may also be included in the tissue coated hydrogels of this invention.

Yet another embodiment of the present invention provides a composition of matter that promotes the proliferation and/or differentiation of animal cells, comprising: an implantable animal tissue, a hydrogel; and an effective concentration of at least one growth factor, wherein the concentration is effective in promoting proliferation and/or differentiation of animal cells.

Yet another embodiment of the present invention provides a composition of matter that promotes the localized delivery of at least one growth factor. Preferably the growth factor is vascular endothelial growth factor (VEGF) or BMP or mixtures thereof.

Yet another embodiment of the present invention provides a process for promoting the healing of wounds, comprising applying to the wound, a composition that contains a non-crosslinked animal degradable animal tissue modified with a synthetic polymer and an effective concentration of at least one growth factor or one small molecule therapeutic, wherein the concentration is effective to promote wound healing.

Another embodiment of the present invention provides a degradable implantable animal tissue based composition that promotes the localized delivery of a poorly water soluble form of a bioactive compound, such as chlorhexidene; chlorhexidene diacetate monohydrate or chlorhexidene dihydrochloride; chlorhexidene gluconate, silver salts such as silver chloride, silver iodide, silver acetate, silver lactate, cell cycle inhibitor such as paclitaxel, lovastatin, rapamycin, sinvastatin, rifampin; or anti-arrhythmic agent such as amiodarone.

In still another embodiment of the present invention, a method for tissue crosslinking or fixation is provided. The method comprises; linking the free radical polymerizable groups on the tissue with a covalent bond; crosslinking the free radical polymerizable groups using free radical polymerizable monomers comprising primary amine group. Further crosslinking the primary amine groups using di or polyfunctional crosslinker such as glutaraldehyde.

In yet another embodiment of the present invention, method for making a degradable tissue matrix comprising substantially water insoluble drug or bioactive compound is provided. The method comprises: dehydrating the membrane like biological tissue; treating dehydrated membrane like tissue with a solution of a substantially water insoluble bioactive compound in an organic solvent; removing the solvent from the treated tissue.

In still another embodiment of the present invention, a method for making a tissue capable of remembering the shape is provided.

In another embodiment, in another embodiment of the present invention, a method for making a tissue is provided wherein certain parties of the tissue are biostable and/or biodegradable.

Other features, advantages, and object of the present invention will become more apparent and be more readily understood from the following detailed description, which should be read in conjunction with the accompanying drawings.

DETAILED DESCRIPTION OF THE PREFERRED EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments.

In order to clarify the terminology present invention, the following definitions are provided. Unless defined otherwise, all technical and scientific terms used herein have the same meaning as is commonly understood by one who is skilled in the art.

"Biodegradable" denotes a material that will degrade in a biological environment by either a biologically assisted mechanism, such as, by way of example, and not limitation, an enzyme catalyzed reaction, or by a chemical mechanism which can occur in a biological medium, such as, by way of example, and not limitation, hydrolysis.

"Biostable" denotes a high chemical stability of a compound in an aqueous environment, which is similar to the environment, found in the human body, such as, by way of example, and not limitation, phosphate buffered saline (pH 7.2).

"Bioactive" refers to one or all of the activities of a compound that show pharmacological or biological activity in human or animal body. Such biological activity is preferred to have therapeutic effect. Substances or compounds that are bioactive are referred to as "drugs" or "bioactive compounds." The bioactive compounds that can be used include, but are not limited to, antiviral agents; antiinfectives such as, by way of example, and not limitation, antibiotics; antipruritics; antipsychotics; cholesterol- or lipid-reducing agents; cell cycle inhibitors; anticancer agents; antiparkinsonism drugs; HMG-CoA inhibitors; antirestenosis agents; antiinflammatory agents; antiasthmatic agents; anthelmintic; immunosuppressives; muscle relaxants; antidiuretic agents; vasodilators; nitric oxide; nitric oxide-releasing compounds; beta-blockers; hormones; antidepressants; decongestants; calcium channel blockers; growth factors such as, by way of example, and not limitation, bone growth factors or bone morphogenic proteins; wound healing agents; analgesics and analgesic combinations; local anesthetic agents; antihistamines; sedatives; angiogenesis-promoting agents; angiogenesis-inhibiting agents; tranquilizers and the like. Cellular elements which can be used for therapeutic use include, but are not limited to mammalian cells including stem cells, cellular components or fragments, enzymes, DNA, RNA, and genes may also be included as bioactive components.

The term "minimally invasive surgery" or (MIS) is used herein includes, but is not limited to, surgical techniques such as, by way of example, and not limitation, laparoscopy, thoracoscopy, arthroscopy, intraluminal endoscopy, endovascular techniques, catheter-based cardiac techniques (such as, by way of example, and not limitation, balloon angioplasty), and interventional radiology.

The term "dehydration" broadly refers to any method that removes the water from the tissue without denaturing the tissue. This includes, but is not limited to processes such as, by way of example, and not limitation, lyophilization, vacuum drying, air drying, or solvent-based drying such as, by way of example, and not limitation, exposing the tissue to various alcohol-based solutions.

"Sustained release" or "long term release or deliveries" are phrases used interchangeably herein, to denote longer than the expected delivery of a bioactive compound from the tissue matrix. In some embodiments, delivery will be at least a day or more, and may extend to weeks, months, or a few years. However, alternate embodiments encompass shorter term release. The long term release can be achieved by any of a number of mechanisms.

A "hydrogel" refers to a semisolid composition constituting a substantial amount of water, and in which polymers or mixtures thereof are dissolved or dispersed. The hydrogels may be physically or chemically crosslinked.

The term "fluid" generally refers to solutions, emulsions, and suspensions.

The term "exposing" refers to soaking the tissue in a fluid comprising the treatment agent for a period of time sufficient to treat the tissue. The soaking may be performed by, but is not limited to, incubation, swirling, immersion, mixing, or vortexing.

Polymeric nomenclature variations such as, by way of example, and not limitation, poly(lactic acid), polylactic acid, or polylactic acid refer to the same polymer, unless or otherwise stated clearly. This is also true for all others polymers referred to herein.

The term "macromonomer" or "macromer" refers to oligomeric or polymeric materials capable of undergoing fee radical polymerization.

The term "activated" means increasing the chemical reactivity of a given functional group so that it can react with the target molecule under mild conditions. By way of example and not limitation, the acid functionality in acrylic acid is not reactive enough to react with amine groups of the tissue in water at pH 7.2 at room temperature. The reactivity of acid group can be increased sufficiently so that it can react with proteins or tissue in water at pH 7.2 at room temperature. This may be achieved by forming n-hydroxy succinimide ester of acid functional group. Many activation chemistries are known in the peptide synthesis or protein modification art and will be apparent to one skilled in the art, in light of the teachings of the present invention. Preferred activating moieties include, but are not limited to, disuccinimidyl moieties, n-hydroxy disuccinimidyl moieties, sulfo-disuccinimidyl moieties, and mixtures thereof.

The phrase "effective cross-linking condition" generally refers to, but is not limited to, exemplary conditions such as treating a biological tissue like bovine pericardium tissue (size 2 cm by 2 cm) with 20 ml 0.4% glutaraldehyde solution in distilled water or in 20 mM phosphate buffered saline (PBS, pH 7.2) for 24 to 48 hours at room temperature (around 25° C.).

"In situ" denotes at a local surgical site, especially within or in contact with living organisms, tissue, organs, or the body.

"Biodegradable polymer" denotes those polymers or macromolecules which degrade or hydrolyze inside the human or animal body without producing harmful degradation products. Polylactic acid or poly(lactic acid) or poly(lactide) or PLA is term used for a polymer which is made from lactide or lactic acid. Similarly, PGA is term used for polyglycolic acid or polyglycolate. Such polymers are generally referred to as polylactones or polyhydroxyacids.

The term "hydrophobic" is defined as materials or polymers having a low degree of water absorption or attraction.

The term "hydrophilic" is defined as materials or polymers having a strong affinity for water.

The term "Tissue Engineering" is defined as the use of a combination of cells, engineering materials, and suitable biochemical factors to synthesize biological tissues.

The term "tissue" or "extracellular matrix" (ECM) includes human or animal tissue suitable for human or animal implantation or medical use. The tissue defined herein includes but is not limited to items such as, by way of example, and not limitation, ligaments; meniscus; basal membrane; bladder tissue, tendons; cartilage tissue; tubular tissue such as, by way of example, and not limitation, arterial tissue and vein tissue; heart valve tissue; demineralized bone tissue; tissues used to construct heart valves such as, by way of example, and not limitation, dura mater and pericardium tissue; transparent issue such as, by way of example, and not limitation, cornea and lens tissue; membrane-like tissue such as, by way of example, and not limitation, porcine pericardium; bovine pericardium; porcine intestine tissue and lung tissue, more specifically porcine sub-mucosa tissue; bladder tissue; human tissue that is generated and discarded during human childbirth, e.g., human placenta and umbilical cord tissue generated during child birth; amniotic membrane tissue; and the like. Among the tubular tissue, tissue such as, by way of example, and not limitation, bovine mesenteric vein, bovine thoracic artery, bovine ureter, sheep carotid arteries are used in preferred embodiments. The tissue can be derived from, but is not limited to, sources such as, by way of example, and not limitation, bovine, human, porcine, horse, sheep, kangaroo, rat, mouse, dog, cat, or rabbit. Tissue derived from human source is generally preferred. Human processed tissue such as AlloDerm® marketed by LifeCell Corporation, NJ may also be used. If the tissue used is from an animal source, the animal may be genetically modified to yield a uniform tissue type or tissue that has similar biological properties as human tissue. For example, the tissue may be obtained from cloned animals. Many cloning technologies including those that have already developed or yet to be developed may, for example, and without limitation, be used to obtain a cloned animal tissue. The animals may also be genetically modified so that the antigens which are recognized by the human immune system are suppressed. The tissue may also be obtained from technologies employed in the tissue engineering art. In one embodiment using a tissue engineering approach, a tissue is generated by growing animal or human derived cells on a biodegradable scaffold. For example, Apligraf™ is a commercially available human tissue engineering product that may also be used in certain applications. In one embodiment, an engineered tissue that is provided as a sheet or membrane is used. In some embodiments, tissue that is not denatured may be preferred. Tissue that is acellular or processed to remove cells or cell debris is used in other embodiments. In some embodiments, it may be preferable to use animal tissue that is substantially free from infectious or harmful animal viruses or proteins such as, by way of example, and not limitation, BSE.

"Bioprosthesis" is defined to include any prosthesis which is derived in whole or part from animal or other organic tissue and which is suitable for human or animal implantation. Thus, the term generally includes, but is not limited to, devices such as animal tissue based heart valves, vascular grafts, annuloplasty rings and other medical devices such as, by way of example, and not limitation, vascular grafts or patch, heart replacements devices, urinary tract and bladder replacements, bowel and tissue resections in general and the like. In general, though not required, the type of tissue utilized as the starting material as well as its modification will depend on the intended use. For example, in the heart valve application, a biostable mechanically durable tissue may, for example, and without limitation, be used. In such an application, a bovine pericardium or porcine aortic root that is crosslinked with a biostable crosslinker may, for example, and without limitation, be used. If the tissue is to be used as a biodegradable drug delivery patch or degradable tissue engineering scaffold, then a non-crosslinked or biodegradable tissue may, for example, and without limitation, be used.

"Crosslink" is defined as understood by those skilled in the bioprosthesis or polymer chemistry art. In general, crosslinking refers to the method of forming covalent bonds or crosslinks between polymeric/macromolecular molecules. The crosslinking process also generally refers to a fixation process which stabilizes the tissue by making the tissue less antigenic and thus less susceptible to enzymatic degradation. A "crosslinking agent" is defined as a compound capable of forming the crosslinking. For example, glutaraldehyde is generally known in the art as crosslinking agent for the tissue.

PEG or PEO is a term used for polymer containing ethylene oxide repeat units.

The term "polymerizable" denotes that molecules have the capacity to form additional covalent bonds resulting in monomer interlinking to oligomer or polymer formation, for example, molecules contain carbon-carbon double bonds of acrylate-type molecules. Such polymerization is characteristically initiated by free-radical formation, for example, resulting from photon absorption of certain dyes and chemical compounds to ultimately produce free-radicals. The term polymerizable is also applicable to compounds which can undergo condensation polymerization and form a linear or crosslinked polymer.

The following examples are provided as a means of illustrating some embodiments of the present invention and are in no way considered limiting of the present invention.

Methods and Compositions for the Preparation of Biostable Tissues.

An exemplary tissue crosslinking method embodiment of the present invention is herein provided for biological tissues to be used in, by way of example, and not limitation, bioprosthetic medical devices such as, by way of example, and not limitation, heart valves, vascular grafts, surgical patch, ligament and meniscus implants.

One embodiment of the present invention provides for a method of crosslinking a tissue comprising steps of treating the tissue under effective cross-linking conditions with a crosslinker comprising unsaturated polymerizable groups and further crosslinking the unsaturated polymerizable groups using free radicals. An alternate embodiment of the present invention provides for a method of crosslinking a tissue comprising steps of treating the tissue under effective cross-linking conditions with a crosslinker comprising unsaturated polymerizable groups and further crosslinking the unsaturated polymerizable groups by free radical copolymerization. The present invention also provides for a method for forming a crosslinked tissue comprising the steps of providing a tissue suitable for human implantation; exposing the tissue to a fluid comprising a functional monomer capable of reacting with a tissue until a portion of the tissue functional groups are covalently bonded to the monomer; and copolymerizing the functional monomer-treated tissue under effective cross-linking conditions with a compound having at least one free radical polymerizable group. Yet another embodiment of the present invention uses a cross-linked biological tissue produced by treating the tissue under effective cross-linking conditions with a biodegradable crosslinker. In one embodiment, the biodegradable crosslinker may be a solute in a fluid comprising a solvent. It is to be understood that in some applications of the present invention may, for example, and without limitation, be used to produce a general composition of matter and/or a bioactive tissue.

As will be set forth in some detail below, one aspect of the present invention provides for a composition of matter that promotes the localized controlled delivery of at least one drug.

FIG. 1 is a schematic representation of exemplary steps involved in tissue crosslinking by free radical polymerization, in accordance with an embodiment of the present invention. Such crosslinking is achieved in two steps. In the first step, the biological tissue of interest is contacted with one or more of the disclosed compounds under conditions effective to introduce unsaturated polymerizable or dimerizable groups in the tissue, i.e., modified with unsaturated polymerizable groups. In the second step, the unsaturated groups are used to form crosslinks between components of the tissue, i.e., the unsaturated groups on the modified tissue are copolymerized with free radical polymerizable monomer and free radical initiator to form a crosslinked tissue with a polymeric crosslink.

The first step shown by way of example in the FIG. 1 for the preparation of tissue with unsaturated groups will next be described in some detail. The unsaturated group modifying agents that may, for example, and without limitation, be used in accordance with embodiments of the present invention comprise an organic functional small molecule, typically, but not limited to, a monomer with functional groups capable of reacting with tissue. Thus, exemplary compounds suitable for use with the described embodiments of the present invention can be generally represented by the following structural formula:

Where F is a functional group reactive with proteins present in extra cellular matrix such as, by way of example, and not limitation, collagen, elastin, keratin and the like; U is an unsaturated group capable of undergoing free radical copolymerization, cyclic dimerization or reaction with thiol group; and X is an organic molecule or radical covalently linking F and U. X may comprise Carbon-Carbon, Carbon-Hydrogen, Carbon-Nitrogen, Carbon-Oxygen, Carbon-Sulfur, Nitrogen-Hydrogen and Oxygen-Hydrogen covalent bonds. X may be polymeric or non-polymeric. F is a functional group that is sufficiently reactive with the components of the tissue such as, by way of example, and not limitation, collagen or elastin molecules present in the biological tissue. For example, functional groups reactive with collagen and suitable for use may include, but not limited to, anhydride, isocyanate, epoxy, n-hydroxysuccinimide, n-hydroxysulfosuccinimide, aldehyde or other protein reactive functionalities known in the art or yet to be developed. It is preferred to have one F per molecule if the tissue crosslinking is not desired. If tissue crosslinking is desired, then the number of F moieties can be two or more per molecule. If the number of F moieties is two or more, the F moieties can be the same functional groups (homo-functional) or different functional groups (hetero-functional). U is an unsaturated group capable of undergoing free radical polymerization or copolymerization. U also can undergo a dimerization reaction. U can have at least one carbon-carbon double bond or triple bond capable of undergoing free radical polymerization. The preferred unsaturated groups include, but not limited to, acrylamides, methacrylamides, acrylates, diacrylates, oligoacrylates, acrolein, methacrolein, fumarates, maleates, methacrylates, dimethacrylates, oligomethoacrylates, itaconates, cinnamic acid derivatives or other biologically acceptable free radical polymerizable groups. The number of U moieties may be one or more per molecule. The arrangement of X, F and U in the molecule may vary in any order according to various embodiments of the present invention. There may be more than one F or U group per molecule.

In various embodiments of the present invention, molecules which are capable of modifying the tissue with unsaturated groups include, but not limited to, glycidyl methacrylate, glycidyl acrylate, acrylic acid N-hydroxysuccinimide ester, methacrylic acid N-hydroxysuccinimide ester; fumaric acid N-hydroxysuccinimide ester; maleic acid N-hydroxysuccinimide ester; itaconic acid N-hydroxysuccinimide ester; acrylic anhydride, methacrylic anhydride, acryloyl chloride, methacryloyl chloride, 2-isocyanatoethyl methacrylate, 2-hydroxyethyl methacrylate, maleic anhydride, fumaric anhydride, cinnamic acid NHS ester, cinnamoyl chloride and the like. Compounds like activated unsaturated di- or polyfunctional acids such as, by way of example, and not limitation, fumaric acid N-hydroxysuccinimide ester; maleic acid N-hydroxysuccinimide ester; itaconic acid N-hydroxysuccinimide ester may crosslink the tissue as well as introduce unsaturated groups. Other dual function compounds (i.e., capable of crosslinking and introducing unsaturated groups) will be apparent to one skilled in the art, in light of the teachings of the present invention.

Figure 2:
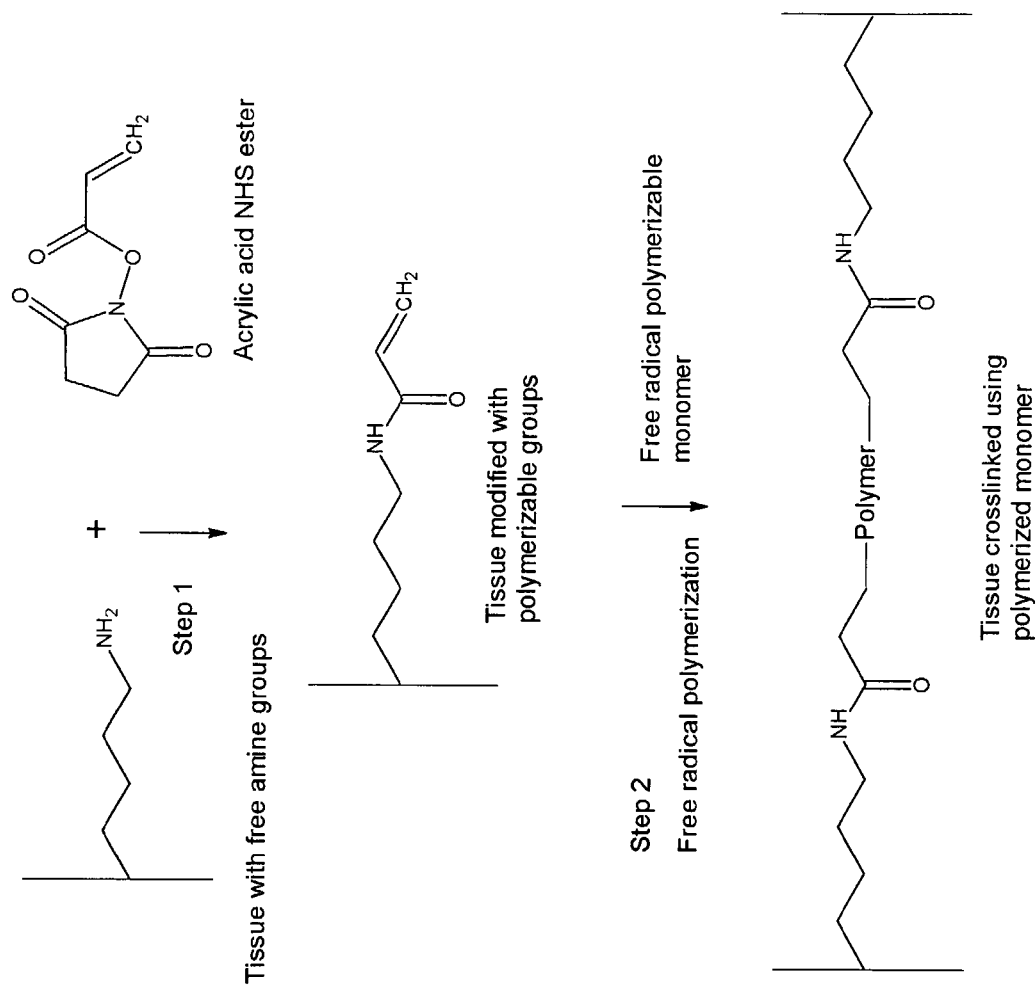
FIG. 2 is an exemplary reaction scheme for tissue crosslinking using acrylic acid n-hydroxysuccinimide (NHS) ester, in accordance with an embodiment of the present invention.
Figure 3:
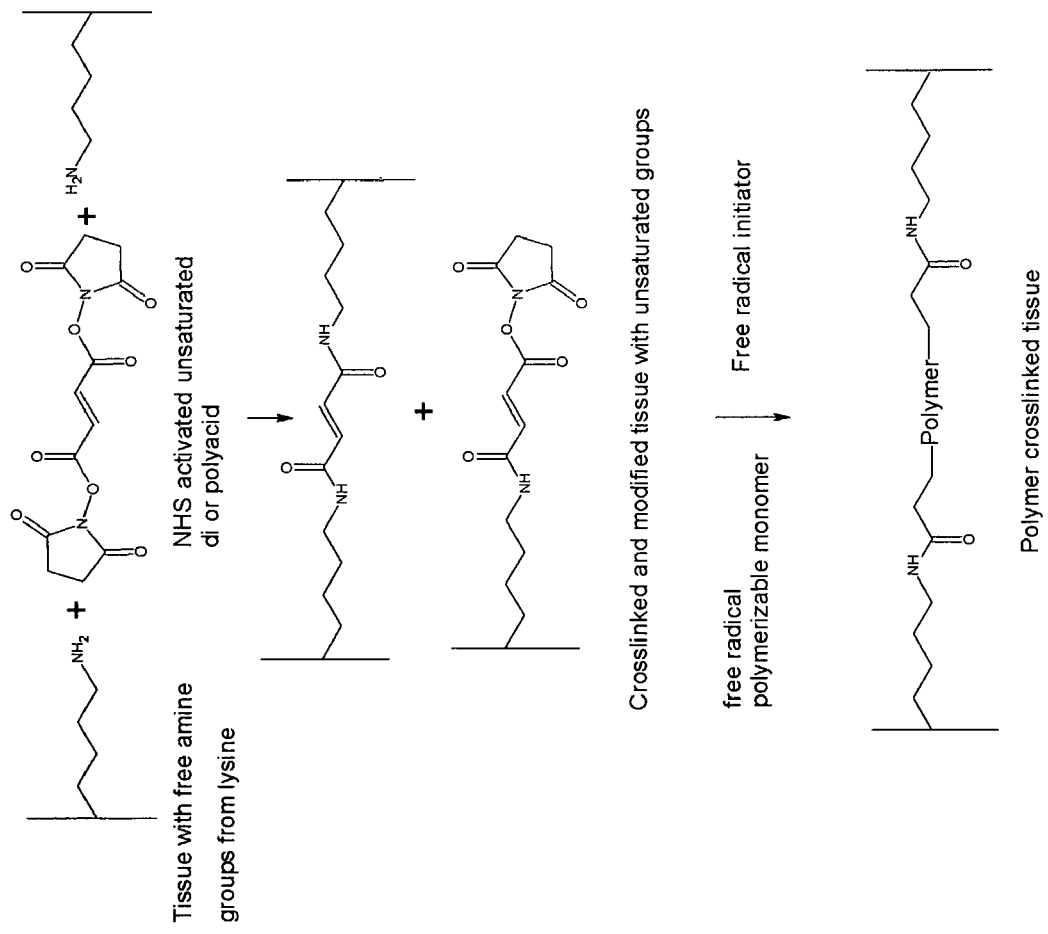
FIG. 3 is an exemplary reaction scheme for tissue crosslinking using di- or polyunsaturated acid n-hydroxysuccinimide (NHS) ester, in accordance with an embodiment of the present invention.

The tissue modification using functional monomers taught by way of example in the present detailed description can be made using any synthetic methodologies known to the skilled in the art of synthetic polymer chemistry, in light of the teachings of the present invention. In one embodiment, another aspect of the present invention is directed to a method of introducing an unsaturated group tissue. The method comprises treating the tissue under effective treatment conditions with a polymerizable organic compound. In one preferred approach, bovine pericardium tissue is modified with an activated unsaturated acid compound. The modification method comprises exposing the tissue to a fluid comprising activated unsaturated acids that can react with amino groups in tissue under mild conditions. As used herein, the term "activated" is applied to an acid moiety-containing compound containing an additional moiety such that the activated acid can react with amino groups under mild conditions. Preferred activating moieties include, but are not limited to, disuccinimidyl moieties, n-hydroxy disuccinimidyl moieties, sulfo-disuccinimidyl moieties, and mixtures thereof. In one embodiment, bovine pericardium tissue is modified using acrylic acid succinimide ester (ANHS). Briefly, bovine pericardium pieces, cut from a freshly obtained bovine pericardial sac, are treated acrylic acid succinimide ester (ANHS) dissolved in dimethyl sulfoxide. The reaction is carried out, for example, in aqueous medium buffered with PBS (pH 7.2). The modification reaction is, for example, carried out for 6 hours at ambient temperature (25° C.) and then for 12 hours at 4° C. with gentle shaking. ANHS is sparingly soluble in water, therefore a solubility enhancing compound such as, by way of example, and not limitation, dimethyl sulfoxide may, for example, and without limitation, be used to facilitate the reaction between activated acid groups and primary amine groups on the tissue. In place of dimethyl sulfoxide, other solvents may also be used. Water soluble solvents are more preferred. Preferred solvents include but not limited to ethanol, methanol, isopropanol, n-methylpyrrolidinone, dimethyl acetamide, dimethyl formamide, tetrahydrofuran, dixoane, acetone, methyl ethyl ketone and the like. The reaction occurs in mild conditions, in water (PBS, pH 7.2) and is usually complete in about 24 hours, more preferably within about six hours. Acidic or alkaline pH conditions may be used to alter reaction kinetics, but mild reaction conditions are generally preferred. The reaction may be carried out in pH ranging from 9 to 6, more preferably 6 to 8 and even more preferably at pH 6.5 to 7.5. Many buffering agents may be used to control the pH. Sodium bicarbonate buffer may be used to achieve pH around 9, phosphate buffer, triethanol amine buffer, 4-(2-Hydroxyethyl)piperazine-1-ethanesulfonic acid Sodium salt (MES) buffer, 4-(2-Hydroxyethyl)piperazine-1-ethanesulfonic acid (HEPES) buffer and the like may be used to control the pH around 7. Acetate buffer may be used to maintain the pH around 4. The tissue modification can also be substantially completed in about 10 minutes and therefore may permit the use of this method during a surgical procedure to modify an autologous tissue. In another embodiment of this method, the modification reaction is carried out under mild acidic conditions; for example, without limitation, a MES buffer, (pH 6.5). In this case, the ANHS is added every 1.5 hours for example, without limitation, to replace the hydrolyzed ANHS. ANHS is generally deactivated by reaction with water generating acrylic acid. The NHS groups of ANHS react with primary amines groups of the tissue forming stable amide bonds. In another embodiment, the modification reaction is carried out, for example, without limitation, in organic solvent such as, though not limited to, dimethyl sulfoxide. Tissue is exposed to, for example, without limitation, 0.2% solution methacrylic anhydride and 1.0% triethylamine in dimethyl sulfoxide for 24-48 hours. The treated tissue is then removed and washed, for example, without limitation, with PBS 3 times to remove solvents and stored until further use. Triethyl amine is used as a base catalyst in modification reactions. Other organic base catalyst such as pyridine, trimethyl amine, N,N-diisopropylethylamine (DIPEA) and the like may also be used. The concentration of methacrylic anhydride and activated NHS ester may be used to control the number of unsaturated groups in the tissue. The concentration of methacrylic anhydride and activated NHS ester during the modification reaction may vary from 0.01% to 25%, most preferably 0.5% to 5% even more preferably 0.2% to 2%. Room temperature reaction conditions (20-25° C.) are most preferred. Temperature higher than 60° C. (above shrink temperature of tissue) is least preferred. The ANHS or methacrylic anhydride reacts with primary amines groups on the tissue. The reaction variables such as, by way of example, and not limitation, time, temperature, concentration, pressure may be controlled in such a way that about 1 to about 100 percent primary amine groups on the tissue are modified. More preferably, about 10 to about 95 percent amine groups are modified, even more preferably about 40 to about 95 percent amine groups are modified. FIG. 2 is an exemplary reaction scheme for tissue crosslinking using acrylic acid n-hydroxysuccinimide (NHS) ester, in accordance with an embodiment of the present invention; and, FIG. 3 is an exemplary reaction scheme for tissue crosslinking using di- or polyunsaturated acid n-hydroxysuccinimide (NHS) ester, in accordance with an embodiment of the present invention. Those skilled in the art, in light of the teachings of the present invention, will recognize that many changes could be made to the tissue modification procedure exemplified above and such changes are considered to be within the scope of the present invention.

In another embodiment, polymerizable groups are introduced using glycidyl methacrylate as a tissue modification agent (see Example 37, step 1 described below). The glycidyl group can react with a number of reactive functional groups such as, by way of example, and not limitation, primary and secondary amines, carboxyl, hydroxyl, and thiol groups. This reactivity with multiple functional groups permits one to modify proteins such as, by way of example, and not limitation, collagen and elastin which are major components of some tissue types. In some cases, tissues may possess high concentration of glycosaminoglycans. An example of such tissue, without limitation, is cartilage tissue. Glycidyl methacrylate may be especially useful to modify such tissues rich with glycosaminoglycans such as, by way of example, and not limitation, hyaluronic acid. Glycidyl methacrylate may also undergo transesterification reaction with hydroxyl groups in the tissue. Many reaction conditions, such as, by way of example, and not limitation, aqueous or non-aqueous medium, time, temperature, concentration may, for example, and without limitation, be used to control degree of substitution. In one preferred embodiment, the reaction temperature is maintained below 55° C., well below shrink temperature of the tissue. A base catalyst such as, for example, without limitation, triethyl amine, trimethyl amine, pyridine is used to accelerate the reaction. A phase transfer catalyst such as, for example, without limitation, tetrabutylamine hydrobromide, tetrapropylamine hydrochloride, may also be employed to facilitate the substitution. The glycidyl methacrylate or glycidyl acrylate may, for example, and without limitation, be used, for example, without limitation, with uncrosslinked tissue or crosslinked tissue such as, for example, without limitation, glutaraldehyde fixed tissue. In one preferred embodiment, 5 pieces of 28 mm pericardial tissues are treated with a 300 ml solution containing 200 ml PBS, 25 ml glycidyl methacrylate and 25 ml triethylamine at 50° C. for 4 hours. Alternatively, the reaction can also be done at room temperature for about 24 hours. The concentration of glycidyl methacrylate may be varied form 1 ml to 25 ml to control the amount of unsaturated groups in the modified tissue.

Figure 4:
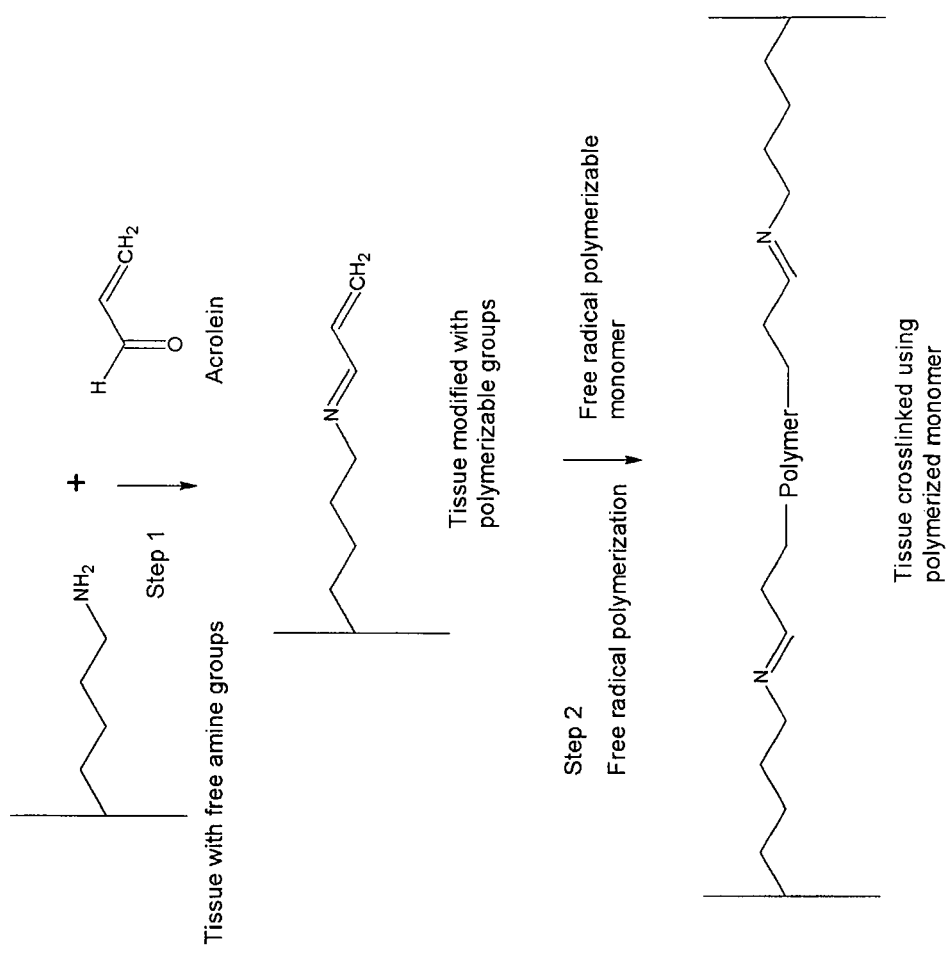
FIG. 4 is an exemplary reaction scheme for tissue crosslinking using unsaturated aldehydes, in accordance with an embodiment of the present invention.

In an alternate preferred embodiment, an unsaturated monoaldehyde such as, for example, without limitation, acrolein or methacrolein is used to modify the tissue with unsaturated groups. Acrolein is highly soluble in water and therefore its modification reaction is very similar to, for example, without limitation, glutaraldehyde fixation chemistry except that no crosslinking occurs. FIG. 4 depicts the reaction scheme for tissue crosslinking using unsaturated aldehydes, in accordance with an embodiment of the present invention. The acrolein reacts with primary amines groups on the tissue. Reaction variables such as, by way of example, and not limitation, time, temperature, concentration, pressure are controlled in such a way that about 1 to about 100 percent primary amine groups on the tissue are modified. More preferably, about 10 to about 95 percent amine groups are modified, even more preferably about 40 to about 95 percent amine groups are modified. In the present embodiment, an aqueous reaction medium is preferred for the modification reaction. Non-aqueous or semi aqueous medium also may, for example, and without limitation, be used in some embodiments. The concentration of acrolein or methacrolein may range from about 0.1% to about 20%, more preferably about 0.1% to about 5%, even more preferably about 0.1% to about 2%. To prevent unwanted free radical polymerization of acrolein or methacrolein, solutions may be supplemented with free radical polymerization inhibitors such as, by way of example, and not limitation, hydroquinone in the reaction mixture. Like glutaraldehyde, acrolein or methacrolein also have antimicrobial properties and therefore may help in reducing bacterial and viral contamination of the tissue.

Unsaturated acid derivatives such as, by way of example, and not limitation, methacrylic anhydride, acrylic anhydride, acryloyl chloride, methacryloyl chloride may also be used to introduce unsaturated groups into the tissue. Primary amine residues are target of such modification chemistries. In one embodiment, methacrylic anhydride is used to modify bovine pericardial tissue. The reaction is carried out in basic buffered medium at low temperature for several days to achieve the desired degree of modification. In another embodiment, the reaction is carried out in aprotic solvent such as, by way of example, and not limitation, dimethylsulfoxide (DMSO) in presence of triethylamine (TEA) as a base catalyst. Five 1 cm by 1 cm pieces are treated with 10 ml DMSO containing 0.02 ml methacrylic anhydride and 0.2 ml TEA. The reaction was carried out at ambient temperature (30°) for 24-48 hours In many of the modification chemistries discussed above, the tissue modification may be carried out in aqueous medium or non-aqueous medium such as, by way of example, and not limitation, organic solvent. The preferred organic solvents are commonly used organic solvents dimethyl sulfoxide, n-methylpyrrolidinone, ethanol and the like. However, other organic solvents may also be employed. Reaction conditions such as, by way of example, and not limitation, time, temperature, concentration will depend on the degree of substitution desired.

The unsaturated group modification methods, which are taught by way of example in the present detailed description, may be modified to obtain a desired degree of substitution. Synthetic methods as such, and otherwise, will be apparent to those skilled in the art, in light of the teachings of the present invention. In most cases, up to about 70 to about 100 percent modification of primary amine groups is preferred to suppress the immune response and to be useful in the crosslinking reactions motioned below.

The unsaturated group incorporation methods for tissues as discussed above may also be used to modify collagen solid particles or collagen sponges or fibers in the solid state. For example, collagen sponges obtained from commercial vendors like Kensey Nash may be treated with ANHS solution or with methacrylic anhydride in DMSO to incorporate acrylic/methacrylic groups in the collagen sponge. The unsaturated group modified collagen sponge is then crosslinked using methods similar to the tissue crosslinking methods mentioned in this document. The crosslinked collagen sponge may have a higher degradation time as compared to uncrosslinked sponge and may be useful in tissue engineering applications especially in bone tissue engineering applications. The crosslinked collagen may be incorporated with BMP to accelerate the bone formation. Though not required, the BMP may be added prior to crosslinking and polymerization reaction.

The first step shown by way of example in the FIG. 1 for the crosslinking of unsaturated group modified tissue will next be described in some detail. In the second step, the unsaturated groups introduced by tissue modification methodologies discussed above are used in tissue crosslinking. In one approach, the unsaturated groups are dimerized, polymerized, or copolymerized and crosslinked with monomers that can undergo free radical polymerization or cyclic dimerization. In another approach, the unsaturated groups are reacted with di- or polyfunctional mercapto compounds to introduce the crosslinking in the tissue.

Crosslinking of Unsaturated Groups in the Tissue Using Free Radical Crosslinking Another aspect of the present invention is directed to a method of crosslinking a tissue, including treating the unsaturated group modified tissue under effective crosslinking conditions with a free radical crosslinking mechanism. In one embodiment of the present invention, a method for crosslinking collagen-containing biological tissue under effective conditions wherein at least a portion of the tissue functional groups form a covalent bond with a compound having the formula F—X—U, wherein F, X, and U are as defined above, then treating the tissue under effective crosslinking conditions with a compound having at least one free radical polymerizable group. Accordingly, the tissue used in this type of crosslinking is first modified using unsaturated groups as discussed above. More preferably, the tissue modified with unsaturated groups such as, by way of example, and not limitation, acrylamide, methacrylamide, acrylate or methacrylate group is used in the crosslinking reaction. In one embodiment of the present invention, the method of crosslinking the tissue is achieved by steps that include, without limitation, treating unsaturated group modified tissue under effective cross-linking conditions with a free radical polymerizable monomer.

In one embodiment, unsaturated group modified tissue is gradually dehydrated in series of aqueous alcohol solutions. The dehydration may also be done using other techniques such as, by way of example, and not limitation, lyophilization or vacuum drying and the like. The dehydrated tissue is then exposed to or incubated in a monomer/monomers solution (n-vinyl pyrrolidinone as an example) containing free radical photoinitiator. The incubation is carried out until the infusion of monomer/initiator is complete throughout the tissue matrix. This may require incubation from minutes to few days. More preferably, tissue is incubated for about 0.1 minute to about 16 hours. Even more preferably, for about 5 minutes to about 2 hours. The monomer/photoinitiator-soaked tissue is then exposed to long wavelength ultraviolet light until polymerization and crosslinking is achieved. The photoinitiator in presence of UV light initiates polymerization of monomer. The unsaturated groups on the tissue copolymerize with the monomer and crosslink the tissue. The overall tissue crosslinking reaction is shown in the example of FIG. 1. In order to effectively crosslink the tissue, the growing polymer free radical must copolymerize or react with unsaturated groups on two collagen chains. This is achieved, for example, without limitation, by selecting a number of polymerization variables such as, by way of example, and not limitation, monomer concentration, percent acrylate modification of the tissue, initiator concentration, UV light intensity, temperature, and the like. In one preferred embodiment, acrylic acid succinimide ester modified or glycidyl methacrylate tissue is dehydrated in aqueous ethanol solutions. The ethanol-treated tissue is then transferred to n-vinyl pyrrolidinone (NVP) solution containing Irgacure 2959 [(4-(2-hydroxyethoxy)phenyl-(2-hydroxy-2-propyl)ketone)] as a long wavelength ultraviolet photoinitiator. The NVP-soaked tissue is irradiated up to 5 minutes using long wavelength UV light (Black-Ray UV lamp, 360 nm flood light, 10000 mW/cm2 intensity). The irradiated tissue is washed with PBS solution to remove unpolymerized monomer and polymerized but uncrosslinked soluble polyvinyl pyrrolidinone polymer.

Glycidyl methacrylate tissue incubated in n-vinyl pyrrolidinone solution but not exposed to light is referred to as the dark control. Untreated tissue is referred as control tissue. Table 1 gives pepsin digestion data on pericardial tissue fixed/crosslinked using glycidyl methacrylate/n-vinyl pyrrolidinone or glycidyl methacrylate/acrylic acid. The data of Table 1 indicates that the untreated control tissue and dark control tissue degraded completely in a pepsin solution indicating their susceptibility to enzymatic degradation. The tissue treated with glycidyl methacrylate and subsequently treated with n-vinyl pyrrolidinone or acrylic acid monomer and free radical initiation showed less than 9 percent weight loss when exposed to pepsin solution indicating their high stability towards enzymatic degradation. The source of the tissue such as, by way of example, and not limitation, bovine pericardium or sheep pericardium did not show a significant difference in weight loss indicating the applicability of this treatment to tissues from different animals. Table 2 lists shrink temperature values for control and treated tissue. Again, the n-vinyl pyrrolidinone-treated tissue showed a significantly higher shrink temperature as compared to untreated control tissue indicating tissue stability and crosslinking.

TABLE 1

Pepsin digestion data for sheep and bovine pericardium tissue fixed using glycidyl methacrylate and free radical polymerizable monomer.

| Tissue Treatment | Pepsin Digestion Weight Loss (%) |
|---|---|
| Control tissue (untreated tissue) | 100* |
| Dark control (all treatments except exposure to light) | 100* |
| Crosslinked sheep tissue (exposure to UV light and photoinitiator, monomer acrylic acid) | 8.3 |
| Crosslinked sheep tissue (exposure to UV light and photoinitiator, n-vinyl pyrrolidinone) | 6.5 |
| Crosslinked bovine tissue (exposure to UV light and photoinitiator and n-vinyl pyrrolidinone) | 2.5 |

*The tissue is totally disintegrated and could not be washed and weighed.

TABLE 2

Shrink Temperature data for control and crosslinked tissue

| Tissue treatment | Shrink Temperature measured by DSC (° C.) |
|---|---|
| Untreated control sheep tissue | 60.9 |
| Sheep pericardium tissue fixed using glycidyl methacrylate and n-vinyl pyrrolidinone | 82.1 |

The crosslinked tissue exhibited a different texture to a human hand as compared to uncrosslinked tissue indicating crosslinking. The crosslinked tissue showed substantially higher shrink temperature as compared to uncrosslinked tissue indicating crosslinking formation. Unlike glutaraldehyde tissue, the crosslinked tissue is found to be non-cytotoxic. In another embodiment of the present invention, a thermal initiator such as, by way of example, and not limitation, azobisisobutyronitrile is used to initiate polymerization and crosslinking of tissue. Yet in another embodiment, radiation or electron beam irradiation or short UV is used to polymerize and crosslink the tissue in presence NVP as comonomer. In these systems, no initiator needs to be added. In some embodiments, a free radical photoinitiator may be chemically or physically attached to tissue being fixed. One aspect of such treatment is that the solution can be fixed without external free radical polymerization initiator.

Those skilled in the art of free radical polymerization chemistry will understand that many changes could be made in the polymerization and crosslinking of tissue, in light of the teachings of the present invention. The polymerization and crosslinking could be initiated using a number of monomers. For example, many monofunctional monomers which form linear soluble polymers could be used in copolymerization and crosslinking of tissue and these include, but not limited to, acrylic and methacrylic esters such as, by way of example, and not limitation, methyl methacrylate, 1-Adamantyl methacrylate, 1-allyloxy-2,3-propane diol, ethyl methacrylate, dimethylaminoneopentyl acrylate, propyl methacrylate, isopropyl methacrylate, n-acryloyl sarcosine methyl ester, dimethylaminoethyl methacrylate, hexyl methacrylate, butyl methacrylate, dicyclopentenyl acrylate, 2-ethyl hexyl methacrylate, 2-methacryloyloxyethyl phosphorylcholine, ethoxyethyl methacrylate, octyl methacrylate, 2-hydroxy-4-acryloylethoxy benzophenone, stearyl methacrylate, 2-hydroxyethyl methacrylate, 2-aminoethyl methacrylate, glycidyl methacrylate, isocyanatoethyl methacrylate, cyclohexyl methacrylate, methyl acrylate, ethyl acrylate, propyl acrylate, isopropyl acrylate, hexyl acrylate, butyl acrylate, 2-ethyl hexyl acrylate, octyl acrylate, stearyl acrylate, 2-hydroxyethyl acrylate, glycidyl acrylate, isocyanatoethyl acrylate, ethoxyethyl acrylate, cyclohexyl acrylate, 2,2,3,4,4,4-hexafluorobutyl acrylate; 2,2,3,4,4,4-hexafluorobutyl methacrylate; 2,2,3,3,3-Pentafluoropropyl acrylate; 2,2,3,3,3-Pentafluoropropyl methacrylate; trifluoroethyl methacrylate, trifluoroethyl acrylate; tetrafluoroethylene, fluorinated vinyl ethers, alkyl acrylamides and methacrylamides such as, by way of example, and not limitation, acrylamide, methacrylamide, n-propyl acrylamide, butyl acrylamide, isobutyl acrylamide, ethyl acrylamide, tertiarybutyl acrylamide, n-propyl methacrylamide, butyl methacrylamide, isobutyl methacrylamide, ethyl methacrylamide, tertiarybutyl methacrylamide, pentyl methacrylamide; pentyl acrylamide; styrene and styrene derivatives such as, by way of example, and not limitation, methyl styrene, chlorostyrene; vinyl ethers such as, by way of example, and not limitation, glycidyl vinyl ether; acrylonitrile, acrylic acid, methacrylic acid, allyl alcohol, allyl amine, polysiloxane or polyether based macromonomers, polyurethane acrylates and methacrylate and the like. Many monofunctional monomers which form linear soluble polymers could be used in copolymerization and crosslinking of the tissue and these include, but not limited to, n-vinyl pyrrolidinone, acrylic acid, 2-hydroxyethyl methacrylate, glyceryl methacrylate, polyethylene glycol acrylate, 2-hydroxypropyl acrylate, monomers used in commercial soft and hard contact lens manufacturing, 2-hydroxypropyl methacrylate, acrylamide, vinyl acetate, silicone-based acrylates and methacrylates, silicone-based monomers used on contact lens manufacturing, n-isopropyl methacrylate, glycidyl methacrylate, glycidyl acrylate, methacrylic acid, acrylonitrile, styrene, methyl methacrylate, methyl acrylate, PEG or PEO acrylates and methacrylates, monomers obtained from fatty acid and fatty acid derivatives, monomers obtained from low molecular weight polyethylene, polypropylene other vinyl polymers and the like. Monomers which are soluble or substantially soluble in water (solubility greater than 1 percent in water) are preferred. The polymerization and crosslinking reaction can be performed in aqueous, semiaqueous or nonaqueous medium. In general, water or alcohol water mixtures are preferred. In water, extreme high or low pH with prolonged exposure times, typically greater than 1 hour are not preferred at least because such conditions can damage or denature the tissue. The preferred pH range is between about 10 to about 2; pH range between about 9 to about 6 is even more preferred, and physiologic pH range around about 7.2 is most preferred. Many buffers can be used to control the pH. Buffers such as, by way of example, and not limitation, phosphate buffer, triethanol amine buffer, acetate buffer, borate buffer, bicarbonate buffer, HEPES buffer are preferred. Among non aqueous media, monomers that can be used as solvents are preferred. For example, n-vinyl pyrrolidinone is a liquid and can solubilize a variety of other monomers without significantly affecting the tissue. Other preferred liquid monomers include liquid PEG-based monomers, n-vinyl caprolactum, 2-hydroxyethyl methacrylate, glyceryl methacrylate, and glycidyl methacrylate, organic solvents such as, by way of example, and not limitation, n-methylpyrrolidinone, dimethylsulfoxide, dimethylformamide, dimethylacetamide etc.; lower ketones (i.e., having from about 3 to 6 carbons) such as, by way of example, and not limitation, methyl ethyl ketone or cyclohexanone; and polyhydroxy compounds such as, by way of example, and not limitation, glycerol, ethylene glycol, or polyethylene glycols having molecular weights less than about 1000 also could be used for polymerization and crosslinking. The free radical initiation necessary for polymerization could also be achieved by exposing the tissue to gamma radiation, electron beam radiation, UV radiation, using photoinitiator or thermal initiators. The gamma radiation, electron beam irradiation or short UV irradiation may not need external free radical initiator. The photoinitiator could be selected depending on the wavelength of interest. For long wavelength UV light, initiator Irgacure 2959, Irgacure 651 (2,2-dimethoxy-2-phenyl acetophenone), benzophenone and the like could be used. For visible light initiation, initiating systems eosin-triethanol amine (irradiation wavelength 512 nm), methylene blue-triethanol amine system (irradiation wavelength 632 nm) and the like could be used. The choice of various photoinitiators and their corresponding wavelength can be found in photopolymerization literature art. Preferred photopolymerization conditions, photoinitiators are described in U.S. Pat. No. 5,410,016 (Hubbell, et al), which is cited here for reference only as one suitable technique. There are many free radical polymerization systems that are known in the dental cement art, contact lens manufacturing art, or in the radiation-cured coating art which can be used in polymerization or crosslinking of unsaturated group modified tissue. However, initiating systems based on long UV or visible light initiated systems are preferred due to higher penetration of light inside the tissue. In general, the higher the wavelength light, the greater penetration in side the tissue. The penetration of light into the tissue can also be controlled by controlling photoinitiator concentration or a chromophore that selectively absorbs light from irradiation sources. The amount of free radical initiator in the formulation may range from about 0.01% to about 2 percent relative to the weight of monomer. Most preferably, the preferred initiator amount is about 0.05% to about 1%. Various light sources such as, by way of example, and not limitation, xenon lamp, mercury lamp, halogen lamp, argon ion laser, solid sate semiconductor based lasers may, for example, and without limitation, be used for photopolymerization and crosslinking of tissues. The light used in the photopolymerization could be transported using fiber optic or liquid guide as known in the photochemistry art or surgical laser instrumentation art. Various types of thermal initiators could also be used; these include, but not limited to, azo-based initiators such as, by way of example, and not limitation, azobisisobutyronitrile, peroxide-based initiators such as, by way of example, and not limitation, benzoyl peroxide, inorganic initiators such as, by way of example, and not limitation, potassium persulfate or ammonium persulfate and the like. The polymerization medium could be aqueous or non-aqueous. In one embodiment, the tissue is dehydrated by lyophilization and then incubated with an aqueous solution of polyethylene glycol acrylate. The polyethylene glycol acrylate is then photopolymerized and crosslinked in water in presence of unsaturated group modified tissue.

The polymerization and crosslinking may also be conducted in water under mild conditions. For example, without limitation, unsaturated group modified tissue is incubated in a 50% aqueous solution of acrylamide or 2-hydroxyethyl methacrylate containing 2% Irgacure 2959 for 24 hours. Acrylamide concentration could be varied from about 10% to about 60% in water with 0.1% Irgacure 2959. The incubated tissue is removed and exposed to long U light for 10 minutes to polymerize and crosslink the tissue. The unreacted monomers are removed by washing. In one embodiment, glycidyl methacrylate modified bovine pericardial tissue (see Example 37 described below) was exposed to with 10-50% acrylamide solution containing 0.1% Irgacure 2959 for 30 minutes and then exposed to long wavelength UV lamp (360 nm light) for 5 minutes. The resultant tissue showed significantly higher shrink temperature as compared to untreated pericardial tissue.

The degree of polymerization and crosslinking can also be controlled by adding special additives known in the free radical polymerization art. For example, a chain transfer agent such as, by way of example, and not limitation, mercapto ethanol may be added to control the molecular weight of polymer formed in the tissue. Other chain transfer agents that can be used include, but are not limited to, biocompatible thiol, bromine or chlorine containing organic compounds. These compounds include, but are not limited to cysteine (amino acid), carbon tetrachloride, chloroform and the like. Inhibitor may be added to monomers to prevent unwanted polymerization during storage. The monomer may be purged with inert gas to remove dissolved oxygen. The molecular weight of polymer produced may range from 1000 to 5 million g/mole, more preferably 5000 to 150000 g/mole, even more preferably 10000 to 10000 g/mol. The choice of molecular weight will depend on the intended use. Typically tissue-polymer composite which require superior mechanical properties may use high molecular weight polymer (>10000 g/mole).

Polymeric crosslinks formed by free radical polymerization generally results into polymers with varying degree of molecular weights or chain lengths. The molecular weight distribution of polymer will depend on experimental conditions used. Typically, the molecular weight distribution, which is generally defined as ratio of weight average molecular weight (Mw) to number average molecular weight (Mn), is 1.1 to 4, more typically 1.3 to 2.5 for most polymeric systems formed by free radical polymerization. Since polymer formed during crosslinking reaction as described above have a range of molecular weight, the polymeric chain length may also vary. Thus, this invention overcomes the limitation of fixed molecular length crosslinking methods such as glutaraldehyde crosslinking and forms polymeric crosslinks with various lengths or molecular weights.

Monomers used may be purified before using them in the polymerization and crosslinking reaction. The purification may be achieved by techniques such as, by way of example, and not limitation, vacuum distillation, column chromatography, recrystallization and the like. Oxygen in the atmosphere may act as an inhibitor and can alter polymerization kinetics. The effect of oxygen can be minimized by conducting the polymerization and crosslinking under inter gas atmosphere. Inert gases such as, by way of example, and not limitation, nitrogen, carbon dioxide, and argon are most preferred.

In one embodiment, the tissue is first crosslinked using a crosslinker containing two or more tissue reactive groups and a polymerizable double bond. The double bond in the crosslinker is then further crosslinked using free radical polymerization. One aspect of this type of crosslinking is that two methods of crosslinking are used in preparing the crosslinked tissue. For example, tissue may be first crosslinked by di- or polyfunctional unsaturated compounds such as, by way of example, and not limitation, n,n-methylenebisacrylamide using a Michael addition reaction known in the synthetic organic chemistry art or a derivative of unsaturated di- or polyacid. This type of crosslinking is similar to glutaraldehyde crosslinking known in the art. The dangling or unreacted double bonds in the crosslinking reaction and double bonds in the crosslinks may be copolymerized and crosslinked using free radical photopolymerization as described earlier. This concept further is illustrated by way of example, and not limitation, in FIG. 3 using unsaturated di-polyacid derivative as an example. The preferred di- or polyunsaturated compounds that may be used include, but are not limited to, n,n-methylenebisacrylamide, polyethylene glycol diacrylate, polyethylene glycol dimethaacrylate, trimethylol propane triacrylate, trimethylol propane trimethacrylate; dipentaerythritol methacrylate, and the like. In one exemplary approach, the tissue is first crosslinked or modified with di- or polyunsaturated diacids (see FIG. 3). These diacids include, but are not limited to, fumaric acid, itaconic acid, maleic acid, castor oil, and the like. Unsaturated acids such as, by way of example, and not limitation, fumaric acid, maleic acid and itaconic acid are preferred due to their high reactivity and ability to copolymerize with variety of monomers. The di- or polyunsaturated acids could be incorporated into the tissue using several chemical methods known in the protein modification art. For example, unsaturated acids like fumaric acid could be incorporated by incubating the tissue in a 1% solution of fumaric acid in PBS or MEM buffer at about pH 4.0 to about 8.0 in the presence of 1-Ethyl-3-(3-dimethylaminopropyl)carbodiimide Hydrochloride (EDC) as an esterification catalyst (2%) and n-hydroxy succinimide as co-catalyst (2%). In a preferred method (see Example 32 described below), an activated derivative of fumaric acid is prepared separately. The preferred derivative is n-hydroxysuccinimide ester (NHS) or n-hydroxysulfosuccinimide ester (SNHS) or fumaryl chloride. The SNHS ester is soluble in water and does not need organic solvents to disperse it. Tissue such as, by way of example, and not limitation, pericardial tissue is first reacted with fumaric acid NHS derivative in PBS. The modified tissue shows increased shrink temperature as compared to unmodified tissue indicating crosslinking. The tissue is also less cytotoxic or non-cytotoxic when compared with tissue fixed using 0.4% glutaraldehyde. The fumaric acid-modified tissue is further reacted or crosslinked with monomers capable of undergoing free radical polymerization as mentioned previously. In one exemplary approach, fumaric acid-modified tissue is reacted or copolymerized with n-vinyl pyrrolidinone using UV photopolymerization. The polymerization reaction variables as well as types of monomers copolymerized can be changed to obtain a desirable implantable tissue material. Bovine pericardial tissue modified with fumaryl chloride and crosslinked with n-hydroxysuccinimide showed higher shrink temperature as compared to unmodified tissue indicating crosslinking.

Yet another embodiment of the present invention provides for a method for making radio-opaque implantable tissue including the steps of providing a tissue suitable for human implantation; exposing the tissue to fluid including a radio-opaque compound capable of reacting with a tissue; and covalently bonding a radio-opaque compound to the tissue. Monomers containing radio-opaque atoms such as, by way of example, and not limitation, iodine or metal ions are used for polymerization and crosslinking. The incorporation of radio-opaque polymerizable monomers will provide radio-opacity to the tissue. The preferred monomers that may, for example, and without limitation, be used are polymerizable derivatives or iodinated compounds such as, by way of example, and not limitation, polymerizable monomer obtained by esterification of triiodobenzoic acid and 2-hydroxyethyl methacrylate. Other iodinated derivatives that may be converted into polymerizable monomers by esterification of hydroxyl groups include, but are not limited to iohexyl, metrizamide, iopamidol, iopentol, iopromide, erythrosin, and ioversol. The polymerizable derivative of metrizamide is most preferred. The radio-opacity is controlled by the changing the amount of radio-opaque monomer incorporated in the tissue. The iodine content of tissue may vary from about 20 to about 300 mg iodine per gram of tissue weight. More preferably, the amount of iodine may be about 40 to about 200 mg/g of tissue.

Tissue could be chemically modified with unsaturated group and free radical initiating group such as, by way of example, and not limitation, eosin or benzophenone. For example, eosin could be physically adsorbed or chemically bound to the tissue using the esterification of carboxyl group on the eosin molecule. Such initiator and unsaturated group modified tissue can be crosslinked using free radical initialing chemistry such as, by way of example, and not limitation, photoinitiation chemistry as discussed previously. In a similar manner, tissue could be chemically modified with thermal initiator and polymerizable group on the same protein chain. One aspect of such systems is that no external free radical initiator is needed to initiate free radical polymerization and crosslinking.

In some embodiments, the tissue could be modified with chemical groups which undergo cyclic dimerization upon exposure to heat or light energy could be attached to tissue and then subsequently dimerized to crosslink the tissue. The compounds which undergo cyclic dimerization include, but are not limited to, cinnamic acid, coumarin, chalcone and thymine. Many functional groups which undergo cyclic dimerization are known in the photochemistry art and could be used; however the derivatives of cinnamic acid are most preferred. Cinnamic acid and its derivatives are known to undergo photodimerization on irradiation with ultraviolet light. This reaction is highly specific and does not require free radical photoinitiator. It can be carried out in liquid, solid, or solution state. Photocurable polymers which can be cured or crosslinked by photodimerization reaction of cinnamic acid have been extensively used in arts related to lithography, paints and printing. In a preferred embodiment, the tissue is first modified with cinnamic acid derivative such as, by way of example, and not limitation, n-hydroxysulfosuccininide derivative of cinnamic acid or cinnamoyl chloride. The modified tissue is then exposed to long wavelength ultraviolet light (360 nm) or visible light to dimerize and crosslink the unsaturated groups in the tissue.

Prosthetic Tissue with Biostable and Biodegradable Regions

Figure 5:
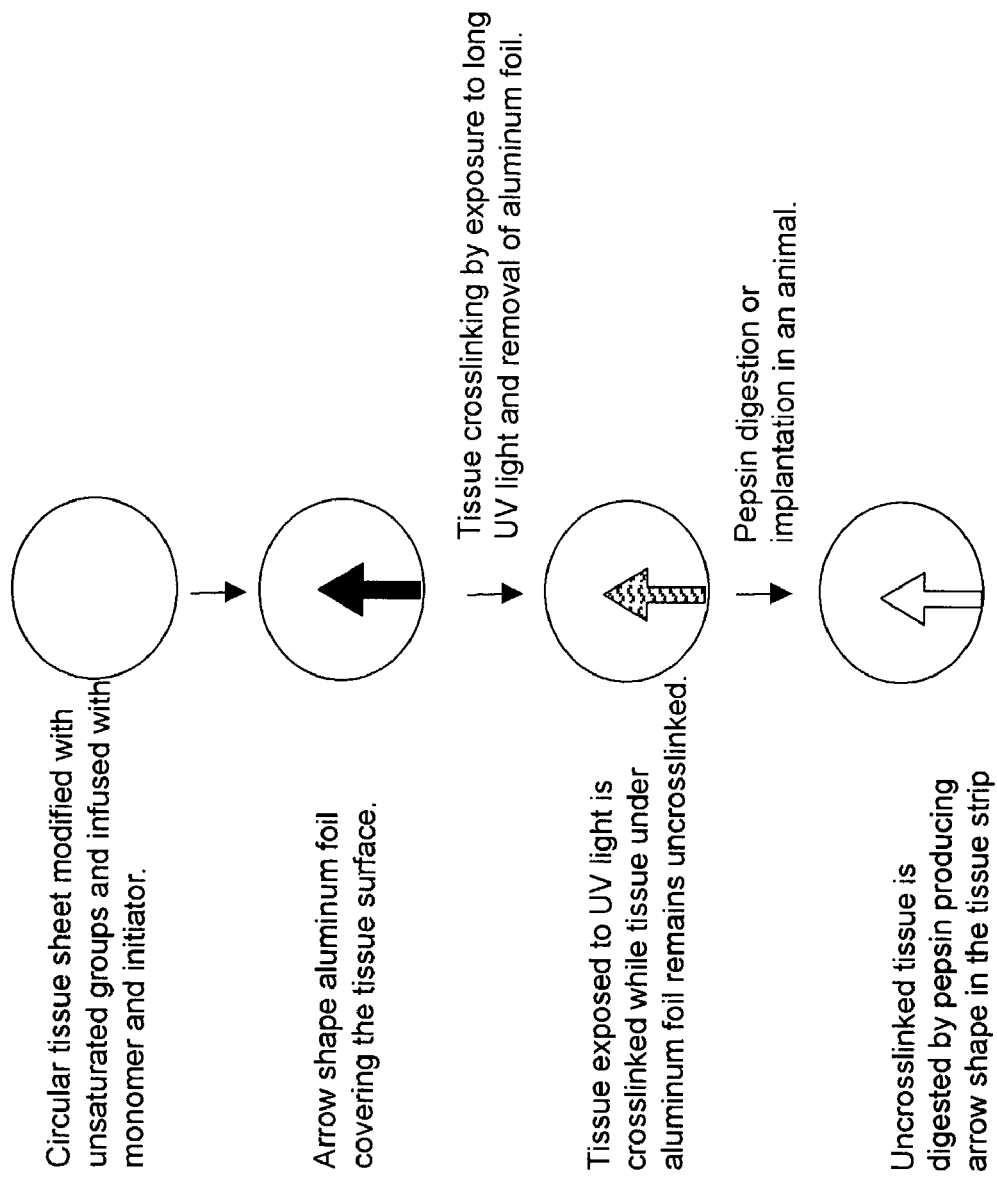
FIG. 5 is a schematic representation of the exemplary preparation of tissue with patterns of biostable and biodegradable regions within the tissue, in accordance with an embodiment of the present invention.

In some embodiments, photopolymerization and crosslinking is controlled by the exposure of light to certain parts of the tissue. This may, for example, and without limitation, be used to crosslink only selected parts of the tissue. In one exemplary embodiment, the tissue was exposed to the light through a mask which permits exposure of light only on a selected predetermined area. The tissue exposed to the light undergoes polymerization and crosslinking. Parts of the tissue, which are not exposed to light remain uncrosslinked and therefore remain susceptible for degradation. This concept is illustrated, by way of example, and not limitation, in FIG. 5. In one exemplary embodiment (see Example 40 described below), a 2 cm diameter tissue treated with glycidyl methacrylate as shown in Example 37 part 1. The tissue is incubated in, by way of example, and not limitation, n-vinyl pyrrolidinone solution containing photoinitiator (Example 37, part 2). The incubated tissue is kept on a glass plate. Two 4 mm diameter aluminum foil sections or arrow shape foil sections are cut and placed on the tissue. The tissue is then exposed to long wavelength UV light for, by way of example, and not limitation, 5 minutes for polymerization and crosslinking of the tissue. The same procedure is repeated from other side of the tissue. The tissue is then exposed to pepsin solution. The areas of the tissues which are covered by aluminum foil showed substantial degradation and is completely solubilized while the light-exposed tissue did not show signs of degradation and was mechanically intact. Thus a pattern of degradable and non-degradable regions is created in the same tissue. Many types of patterns of crosslinked and non-crosslinked tissue may be generated which include rectangular, circular or complex patterns or shapes inside the tissue matrix using this approach. The selective crosslinking and polymerization approach could be, for example, used to selectively reinforce certain parts of medical devices such as, by way of example, and not limitation, heart valve. Certain high-stressed sections of bovine pericardial heart valve tissue are susceptible to calcification and mechanical failure. Such sections may be selectively crosslinked by exposing those sections to light. It can also be used in vivo tissue engineering application.

In some embodiments, the solvents and other crosslinking constituents used during the polymerization and crosslinking process may be subjected to mild or high pressure to obtain a suitable crosslinking density.

Shape Preserving Tissue Fixation

Figure 6:
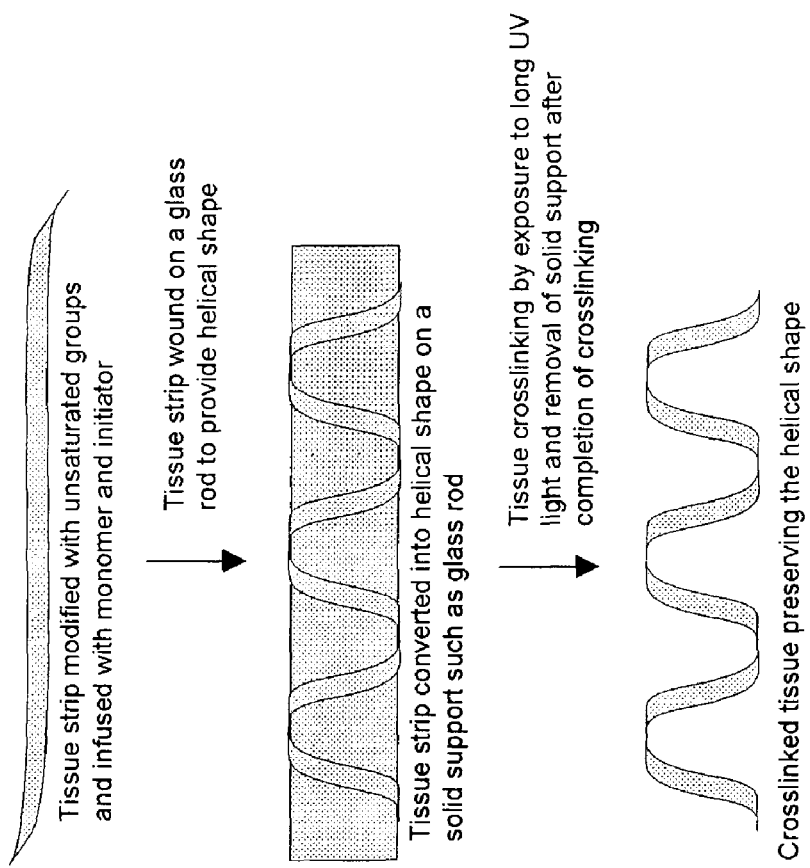
FIG. 6 is a schematic representation of an exemplary shape-preserving tissue fixation method, in accordance with an embodiment of the present invention.

In some preferred embodiments, the collagen fibers may be strained or oriented along the direction of pull prior to polymerization and crosslinking. The tissue orientation may be, for example, and not by way of limitation, achieved through the use of mechanical force. For example, unsaturated group modified bovine pericardial tissue is dried, infused with n-methylpyrrolidinone and photoinitiator 2959 and then stretched to about 110 to about 150% of its length to orient the fibers along the direction of force. The monomer and initiator infusion could also be made after orienting the tissue. The strained tissue is then exposed to long UV light for polymerization and crosslinking. The polymerization and crosslinking will "lock in place" the oriented structure of the proteins/fibers in the tissue and thus yielding a tissue with superior mechanical properties, especially along the axis of orientation. Modification of various variables used in this method such as, by way of example, and not limitation, direction of force applied, axis of orientation, % stretching or compression used, polymerization conditions, monomers used must be optimized for a given application. It was discovered that some monomers which produced highly crosslinked and rigid polymers can substantially preserve the shape of a crosslinked tissue. This concept is schematically illustrated, by way of example, and not limitation, in FIG. 6. In one exemplary embodiment (see Example 29 described below), a 15 cm long and 3 mm wide strip of bovine pericardial tissue modified with glycidyl methacrylate was infused with triethyleneglycol dimethacrylate or tetraethyleneglycol dimethacrylate monomer containing 500 ppm Irgacure 651 photoinitiator. The monomer infused strip is then spirally wound, by way of example, and not limitation, on a 5 mm diameter mandrel (glass rod) in a helical shape. The tissue was then exposed to long UV light for 5 minutes (Black-Ray UV lamp, 360 nm light, 10000 mW/cm2 intensity) for polymerization and crosslinking of the monomer. The glass rod was removed. The tissue shape of helical coil was substantially preserved after removal of glass rod or mandrel. When coiled tissue was stretched along the axis of the helical coil, and the stress is removed, the tissue substantially returned to the helical coil shape indicating shape memory property. This ability to remember the shape after fixation on crosslinking can be beneficial in making novel medical devices. For example, it can be used to form a tissue-based stent-like devices. The light exposure and polymerization can be done in situ at a surgical site. The monomer and photoinitiator infused tissue strip is immobilized, by way of example, and not limitation, on an angioplasty catheter. The catheter is capable of emitting 360 nm light carried using, by way of example, and not limitation, fiber optic cable on the balloon surface. The tissue is transported at the angioplasty site using, for example, without limitation, standard balloon angioplasty techniques, expanded and exposed to emitting 360 nm light until polymerization is complete (typically less than 5 minutes). The balloon is withdrawn and coiled tissue is left at the angioplasty site which provides mechanical support similar to metal-like stent. In another modification of this approach, a monomer infused unsaturated group modified pericardial tissue as mentioned previously was converted or sewn into a 6 mm diameter tube. The tube was then mounted on a 6.1 mm diameter stainless steel mandrel and compressed to reduce the length of the tube (10 to 50 percent reduction in length). The compressed tissue is then exposed to UV light to crosslink the monomer and fix the tissue. The shape of the tissue is preserved in a compressed shape. The mandrel is removed and the compressed tissue tube held the shape with accordion-like wrinkles in the tube. The tube is compressible along the axis of the tube. Such a tube may be useful to make peripheral vascular and coronary graft and other medical devices. Any desired drug such as, by way of example, and not limitation, heparin, by way of example and not limitation, may be incorporated in the tube to influence the desired biological or therapeutic outcome.

One embodiment of the present invention provides for a method for making a tissue capable of remembering a shape.

In one embodiment, a radiation polymerization or electron beam-induced polymerization technique is used to form a crosslinked tissue. Such a reaction can be carried out in the solid state. The gamma radiation or electron beam irradiation generates several free radicals in the tissue. The generated free radicals react with unsaturated groups in the tissue to promote crosslinking. Radiation polymerization may not require free radical initiators. The dose of radiation will depend on the amount of polymerization and crosslinking desired. It is contemplated that such optimization can be readily undertaken by one skilled in the art, in light of the teachings of the present invention, without undue experimentation. Low to moderate radiation doses, typically below about 3-5 MRAD, are preferred at least because high radiation dose may also degrade collagen molecular chain.

One aspect of the present invention is that many monomers with different properties such as, by way of example, and not limitation, charge density, hydrophobicity, thermosensitivity could be used to impart different properties to the crosslinked tissue. In one embodiment, a functional monomer such as, by way of example, and not limitation, glycidyl methacrylate which has a glycidyl group is copolymerized along with vinyl pyrrolidinone. The polymerization of glycidyl methacrylate provides glycidyl functional groups on the crosslinked polymer chain which could be further reacted using standard epoxy chemistry for additional crosslinking or other types of tissue modifications. Functional monomers that could be used, but are not limited to, are 2-isocyanate methacrylate, acrylic acid, methacrylic acid, 2-hydroxyethyl methacrylate, glyceryl methacrylate and the like. As those skilled in the art will appreciate, chemical variables such as time, temperature, concentrations, pressure, catalysts and the like may be controlled to promote additional crosslinking. Moreover, the use of these variables will, at least, depend on a particular chemical reaction used in crosslinking.

In another embodiment, monomers containing long alkyl chains are used in polymerization and crosslinking. The introduction of a long chain through crosslinking can reduce its calcification potential and may improve hemocompatibility of the crosslinked tissue. It is hypothesized that long chain alkyl chains, typically more about 8 carbons (C8), more typically with carbon lengths such as, by way of example, and not limitation, C16-C18, specifically bind to albumin and thus improve hemocompatibility of the tissue. However, shorter alkyl chains, typically >C4, may also be advantageous for some applications.

In some embodiments, the monomers that give fluorinated polymers upon polymerization may, for example, and without limitation, be used to incorporate fluorinated polymers in the tissue. The monomers including fluorinated monomers such as, by way of example, and not limitation, acrylates and methacrylates with fluorinated alkyl chains may, for example, and without limitation, be used. The fluorinated monomer include, but are not limited to, 2,2,3,4,4,4-hexafluorobutyl acrylate; 2,2,3,4,4,4-hexafluorobutyl methacrylate; 2,2,3,3, 3-pentafluoropropyl acrylate; 2,2,3,3,3-pentafluoropropyl methacrylate; trifluoroethyl methacrylate, trifluoroethyl acrylate, tetrafluoroethylene and the like.

In another embodiment of the present invention, a silicone- or polydimethylsiloxane-based monomer or macromonomer is used in polymerization and crosslinking of the tissue. Many silicone- or polydimethylsiloxane-based monomers could be suitably used and are known to one skilled in the art. The incorporation of highly elastomeric silicone-based monomers incorporates silicone rubber in the tissue matrix which provides elastomeric properties and improves oxygen permeability of the tissue in many applications. Polypropylene glycol and some polyurethane acrylates and methacrylate-based monomers that also form elastomeric polymeric crosslinks may also be used. Commercially available polydimethyl siloxane-based macromonomers known in the soft contact lens manufacturing art can be useful in many applications, at least because use of such monomers is already commercialized in high oxygen permeable contact lens applications.

In another exemplary embodiment (see Example 11 described below), a monomer which produces a thermosensitive polymer such as, by way of example, and not limitation, poly(n-isopropyl acrylamide) is used in polymerization and crosslinking of tissue. The incorporation of thermosensitive polymer crosslinked network permits one to rehydrate the collagen chains at low temperature (<10° C.). At body temperature (37° C.), poly(n-isopropyl acrylamide) becomes hydrophobic. The hydrophobic domains thus formed may provide interesting properties to the tissue. For example, hydrophobic domains may, for example, and without limitation, be used to lock or dissolve hydrophobic drugs in the treated tissue. The hydrophobic domains may also provide additional protection against enzymatic degradation of the tissue. Many n-alkyl acrylamide-based monomers which upon polymerization yield thermosensitive polymers could be used, these include, but are not limited to, n-ethyl acrylamide, n-propyl acrylamide, n-isopropyl acrylamide, n-butyl acrylamide, n-isobutyl acrylamide, n-tertiarybutyl acrylamide, n-pentyl acrylamide, and the like. In one illustrative embodiment, glycidyl methacrylate treated pericardial tissue (see Example 37, part 1 described below) is exposed to, for example, without limitation, 50 percent n-isopropylacrylamide solution in water containing 0.1% Irgacure 2959 for 2 hours. The monomer infused tissue was exposed to long UV light for 5 minutes (Black-Ray UV lamp, 360 nm light, 10000 mW/cm2 intensity) for polymerization and crosslinking of the monomer. The tissue was washed with distilled cold water to remove monomer and polymerized but not covalently bound polymer. The tissue represents an example of pericardial tissue crosslinked using thermosensitive polymer. The tissue showed substantially higher shrink temperature as compared to untreated pericardial tissue indicating crosslinking using n-isopropylacrylamide. Any number of bioactive compounds such as, by way of example, and not limitation, paclitaxel, for example, could be diffused inside the matrix at low temperature (typically below 15° in water). At body temperature, n-hydroxysuccinimide becomes hydrophobic trapping the drug in the hydrophobic matrix and releasing it in a controlled manner. Hydrophobic drugs such as, by way of example, and not limitation, paclitaxel, rapamycin, chlorhexidene gluconate are preferred. Other hydrophobic drugs may also be used in alternate embodiments of the present invention. Certain polymeric monomers or macromonomers, such as, by way of example, and not limitation, monomer made from block copolymers of PEG and polypropylene oxide or polypropylene oxide, for example PEG-PPG-PEG acrylates and methacrylates which are soluble in water at low temperature may also be used. Alternatively, thermosensitive polymer-based crosslinkers can also be used to crosslink the tissue. The crosslinking may be carried out when the thermosensitive polymer crosslinker is soluble in water.

In another embodiment, the monomers containing charged groups such as, by way of example, and not limitation, sulfonic acid salts or carboxylic acid salts are used for polymerization and crosslinking. It is believed that incorporation of charged groups in the crosslinked tissue may reduce the propensity for calcification and improve hemocompatibility. The monomers containing charged groups that may be used, but are not limited to, are 2-acrylamido-2-methylpropane sulfonic acid, vinylsulfonic acid, styrene sulfonic acid, sulfoethylmethacrylate, sulfopropylmethacrylate, or other vinyl sulfonic acids; acrylic acid, methacrylic acid, fumaric acid, maleic anhydride, maleic acid, fumaric acid, itaconic acid, and the like. Monomers containing sulfonic acid salts are most preferred. The polymerization of such charged groups creates localized acidic or basic environment which may reduce calcification upon implantation. In one exemplary embodiment, crosslinking of glycidyl methacrylate modified tissue using 2-acrylamido-2-methylpropane sulfonic acid showed substantially higher shrink temperature as compared to untreated tissue indicating crosslinking.

In another embodiment, the monomers containing free amine groups are used for polymerization and crosslinking of the tissue. The amine groups in the monomers can be used to introduce additional crosslinking in the tissue. The amine-containing monomers that may be used, but are not limited to, are 2-aminoethyl methacrylate, allyl amine, 3-aminostyrene, and the like. After polymerization, amine groups in the polymeric crosslinks may be further crosslinked using difunctional amine reactive crosslinkers such as, by way of example, and not limitation, glutaraldehyde, EDC, di- or polyepoxides based crosslinkers. For example, without limitation, tissue crosslinked using allyl amine is further treated with 0.2% glutaraldehyde solution for 24 hours. The glutaraldehyde treatment creates additional crosslinking tissue proteins and amine groups of polymerized allyl amine.

In some embodiments, monomers containing phosphorylcholine moiety may be used to crosslink the tissue. Monomers such as 2-methacryloyloxyethyl phosphorylcholine (MPC) could be infused into the tissue and homopolymerized or copolymerized to promote crosslinking and/or grafting. The MPC polymers and copolymers are well-known for their excellent biocompatibility and blood compatibility presumably due to cell membrane like properties of MPC copolymers In one embodiment, polyvinyl alcohol is incorporated in the tissue. This is achieved by polymerizing vinyl acetate monomer in the glycidyl methacrylate modified tissue. The polyvinyl acetate incorporated in the tissue is converted into polyvinyl alcohol by exposing the tissue to mild acid hydrolysis conditions. The polyvinyl alcohol incorporated in the tissue could be further crosslinked by methods known in the art such as, by way of example, and not limitation, glutaraldehyde crosslinking, metal ion crosslinking or freezing and thawing. Using a similar approach, semicrystalline polymer polyacrylonitrile can be incorporated in the tissue and is then partially hydrolyzed to produce polyacrylic acid. The partially hydrolyzed polyacrylonitrile produces strong mechanical hydrogels.

In another embodiment of the present invention, a monomer which forms a polymer with ability to form complexes with ions, drugs, small molecules and polymers is used in crosslinking and polymerization. In one exemplary embodiment, vinyl pyrrolidinone monomer is used to polymerize and crosslink the modified tissue as (see Example 37 described below). The polymerized polyvinyl pyrrolidinone (PVP) can form complexes with various bioactive compounds such as, by way of example, and not limitation, free iodine, iodide ions and antibiotics. Using a similar scheme, polyacrylic acid introduced by crosslinking with acrylic acid monomer is complexed with polyethylene glycol. It is understood that many other polymer-polymer complexes or polymer-small compound complexes could be used. A monomer-containing cyclodextran may also be used. The cyclodextran moiety is useful for complexing variety of bioactive compounds. The selection of such complexes will depend on the properties desired and can readily be practiced by one skilled in the art in light of the teachings of the present invention. For example, an iodine-polyvinyl pyrrolidinone complex may, for example, and without limitation, be used to impart antibacterial properties to the tissue. Polyacrylic acid or acid groups present in the tissue may be complexed or ionized with silver salts to produce an antimicrobial effect due to release of silver ions. Many silver salts can be used to form a silver salts; these include, but are not limited to, silver acetate, silver benzoate, silver chloride, silver carbonate, silver iodide, silver iodate, silver nitrate, silver laureate, silver sulfadiazine, silver palpitate, silver aspartate, silver succinate, and mixtures thereof. Silver phosphate, silver sulfadiazine, silver citrate, silver lactate, and mixtures thereof are preferred. In one embodiment, the ionized polyacrylic acid modified tissue material/collagen implant is incubated in a concentrated solution of sodium lactate (for example, without limitation, 0.1M to 1.0M) for about 10 to about 60 minutes, most preferably about 30 minutes. The materials are then transferred to a selected silver salt solution (e.g., silver lactate) for about 5 to about 120 seconds, preferably about 60 seconds, in order to produce an antimicrobial surface that retains silver ions and slowly releases them over an extended period.

In another embodiment of the present invention, a di- or polyfunctional water soluble macromonomers such as, by way of example, and not limitation, polyethylene glycol diacrylate or polyethylene glycol dimethaacrylate is used to polymerize and crosslink the animal tissue. In one embodiment, a 5 to 35%, more preferably 10-25%, even more preferably 23% solution of polyethylene glycol, molecular weight 10000 moles/g (PEG10KDA) is used to crosslink the tissue. Briefly, unsaturated groups modified tissue is soaked in the PEG10DA solution containing Irgacure 2959 as photoinitiator and heparin as a bioactive compound. The PEG10DA in the tissue is then polymerized and crosslinked. The tissue is washed with water to remove unreacted PEG10DA. The heparin entrapped in the crosslinked tissue-PEG10DA matrix is slowly released. Other monomers such as, by way of example, and not limitation, polyethylene glycol dimethaacrylate, polypropylene glycol diacrylate or methacrylate, to name a few, may also be used. Polyethylene glycol diacrylate with molecular weight from 400 to 100000 Daltons could be used to control the molecular porosity of the crosslinked polymer network. In some embodiments, the monomers containing degradable links are used to crosslink the tissue. The monomers could be small molecule in nature (typically molecular weight less than 2000) or polymeric macromonomers. In one embodiment, a polyethylene glycol based degradable macromonomer is used. Briefly, a biodegradable monomer is synthesized from polyethylene glycol. The polyethylene glycol chain is extended using oligomeric polyhydroxyacid or polylactone links and then terminated with acrylate polymerizable end groups. The polyhydroxyacid or polylactone links serve as biodegradable sites in the monomer. These sites undergo hydrolysis or biodegradation and break the polymeric crosslinks and making the tissue susceptible for enzymatic degradation. In another embodiment of the present invention, a liquid hydrophobic biodegradable monomer is synthesized by polymerization of cyclic lactones and modifying the terminal group with polymerizable groups such as, by way of example, and not limitation, acrylic group is used. Briefly, unsaturated group modified tissue and biodegradable monomers are copolymerized using a free radical polymerization technique such as, by way of example, and not limitation, photopolymerization. Upon crosslinking, the degradable polyhydroxyacid or polylactone links undergo hydrolysis and the tissue becomes non-crosslinked and therefore susceptible for enzymatic degradation. Depending on the type of polyhydroxyacid or polylactone used, the crosslinked tissue degradation may be controlled. The degradation may range from weeks to years. In general, oligoglycolate polymer crosslinks will degrade in weeks, oligolactate crosslinks will degrade in months and oligocaprolactone crosslinks will degrade in years. In one embodiment, the hydrophobic liquid biodegradable oligomer is polymerized in the presence of tissue microparticles obtained by cryogenic grinding. The polymerization is conducted in a mold and sodium chloride is used as a porosity-inducing compound. In another embodiment of the present invention, a degradable monomer containing hydrolizable bond is obtained from hydroxy alcohols such as, by way of example, and not limitation, hydroxy amine or ethanol amine. These hydroxy alcohols are reacted with acryloyl chloride or methacryloyl chloride to form ester-amide derivative. The ester bond is susceptible to hydrolysis upon implantation. Biodegradable monomers containing peptide links that can be broken down by enzymes such as, by way of example, and not limitation, collagenase, pepsin, etc. may also be used in crosslinking. The tissue-synthetic biodegradable crosslinked material composite may, for example, and without limitation, be used as scaffold for tissue engineering such as, by way of example, and not limitation, scaffold for bone tissue engineering. Cells, enzymes or bioactive compounds may be incorporated during polymerization and crosslinking process to enhance the therapeutic effect.

Di- or polyunsaturated monomers containing degradable bonds have also been disclosed in U.S. Pat. Nos. 6,713,646 (Zhang, et al) and 5,410,016 (Hubbell, et al), which are cited here for reference only. Such monomers and their copolymers with other known biocompatible monomers can also be used to form biodegradable hydrogels in the tissue matrix. Briefly, monomers described in the above cited references are reacted with tissue modified with unsaturated groups and polymerized as described above. The hydrogels incorporated into the tissue matrix degrade by hydrolysis making the tissue susceptible to enzymatic degradation.

In some embodiments, a glutaraldehyde-crosslinked tissue or EDC crosslinked tissue is first reacted with glycidyl acrylate or methacrylate to introduce unsaturated groups in the tissue. These unsaturated groups are then further crosslinked using various monomers as described above. This approach is especially useful for heart valve bioprosthesis made using bovine pericardial tissue or porcine aortic root tissue.

In some instances, more than one crosslinking method may be employed to obtain a desirable crosslinked tissue.

In an alternate embodiment of the present invention, the method for making the tissue is carried out such that part(s) of the tissue are biostable and/or biodegradable. Table 3 provides a summary of experiments performed to stabilize the tissue by various embodiments discussed above.

TABLE 3

Summary of experiments related to biostable tissue stabilized by polymeric crosslinks. The tissue was first modified with unsaturated groups and then crosslinked by free radical photopolymerization using various monomers

| Group | Type of Tissue | Unsaturated group modifying reagent | Monomer used in free radical polymerization | UV light exposure | Shrink Temperature (° C.) | Resistance to pepsin digestion | Visual Observation after 60 day subcutaneous implantation in rat |
|---|---|---|---|---|---|---|---|
| Untreated Control | Bovine pericardium | No treatment | No Treatment | No | 60 | Digested completely | Substantially degraded |
| No Unsaturated group control | BP | No treatment | Vinyl pyrrolidinone, 100% (VP) | Yes | 60 | Digested completely | — |
| Dark Control | BP | Glycidyl methacrylate (GM) | 100% VP | NO | 60 | Digested completely | Substantially degraded |
| VP fixed-1 | BP | GM | 100% VP | Yes | >95 | Very good | No degradation |
| VP fixed-2 | BP | GM | 100% 2-hydroxyethyle methacrylate | Yes | >95 | — | — |
| VP fixed-3 | BP | GM | 20% NIPAM | Yes | >95 | — | — |
| VP fixed-4 | BP | GM | 50% NIPAM + 50% VP | Yes | >95 | — | — |
| VP fixed-5 | BP | GM | Tetraethyleneglycol dimethacrylate | Yes | >95 | — | — |

TABLE 3-continued

Summary of experiments related to biostable tissue stabilized by polymeric crosslinks.
The tissue was first modified with unsaturated groups and then crosslinked by free
radical photopolymerization using various monomers

| Group | Type of Tissue | Unsaturated group modifying reagent | Monomer used in free radical polymerization | UV light exposure | Shrink Temperature (° C.) | Resistance to pepsin digestion | Visual Observation after 60 day subcutaneous implantation in rat |
|---|---|---|---|---|---|---|---|
| VP fixed-6 | BP | GM | 2-acrylamido-2-methylpropane sulfonic acid | Yes | — | — | — |
| VP fixed-7 | Bovine vein | GM | 100% VP | Yes | >95 | Very good | No degradation |
| VP fixed-8 | Bovine cornea | GM | 100% VP | Yes | — | — | — |
| VP fixed-9 | Bovine meniscus | GM | 100% VP | Yes | — | — | — |
| VP fixed-10 | Sheep skin | GM | 100% VP | Yes | >95 | Very good | — |
| Acrylic acid fixed | BP | GM | 100% Acrylic acid | Yes | >95 | Very good | |
| Acrylamide fixed | BP | GM | 50% acrylamide in water | Yes | >95 | Very good | |
| Acrylamide fixed | BP | GM | 10% acrylamide in water | Yes | >95 | Very good | |
| Fumaryl chloride | BP | Fumaryl chloride | 100% VP | Yes | >95 | Very good | |
| Methacrylic anhydride (MA) | BP | MA | 100% VP | Yes | >95 | Very good | |
| Methacrylic anhydride (MA) | BP | MA | 100% VP | No. Used thermal initiator | 73 | — | |

It clear that a variety of tissue types from various animal sources can be stabilized using the inventive methods described above. In many cases, the tissue did not show shrinkage in boiling water indicating high stability and crosslinking of collagen/protein molecules. The unmodified tissue, dark control tissue (tissue modified with unsaturated groups and infused with monomer and photoinitiator but not exposed to light) and unsaturated group control (tissue not modified with unsaturated group, but infused with monomer and photoinitiator solution and exposed to UV light) showed substantial degradation when subjected to pepsin digestion and low shrink temperature, typically around about 60° C. Thermally initiated polymerization also showed higher shrink temperature. Some fixed and unfixed tissues are subjected to rat subcutaneous implantation for 60 days. The fixed tissue showed excellent biostability with no sign of degradation. The untreated tissue and dark control tissue are either completely digested or substantially digested indicating poor biostability or biodegradation.

Crosslinking of Tissue with Di- or Polymercapto Compounds

Figure 7:
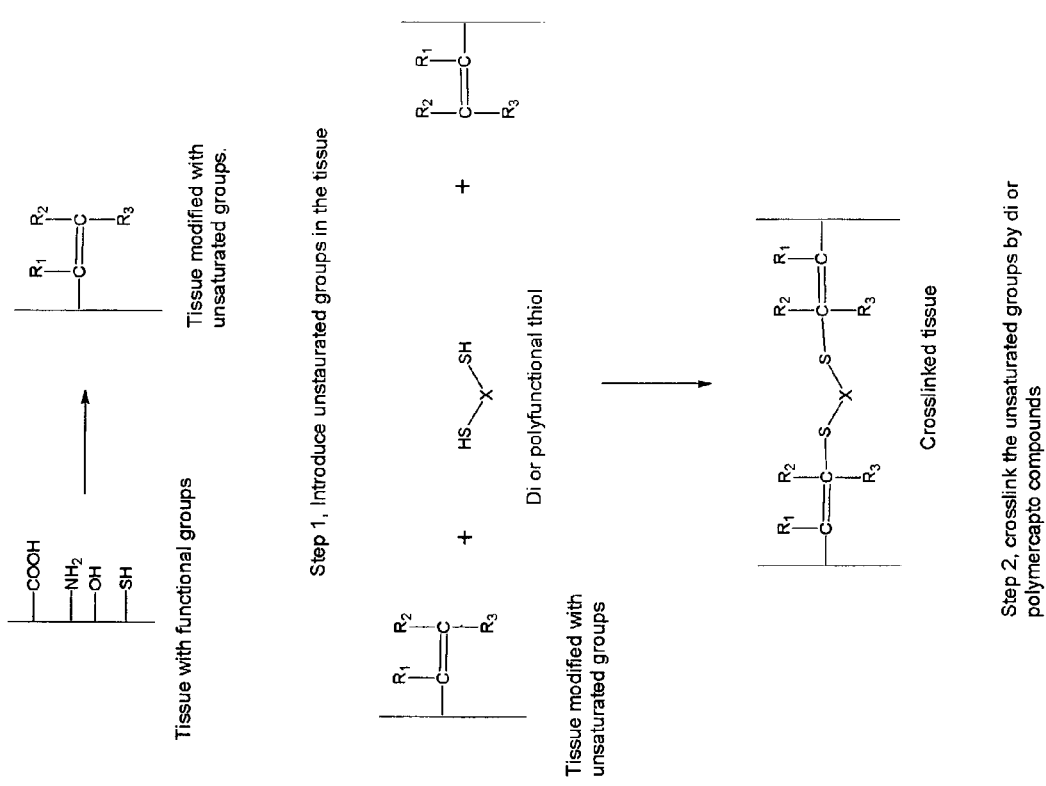
FIG. 7 is a schematic representation of exemplary steps involved in tissue crosslinking using mercapto compounds, in accordance with an embodiment of the present invention.

The tissue modified with polymerizable unsaturated groups may be crosslinked using di- or polyfunctional mercapto compounds. The modified tissue is treated under effective cross-linking conditions with a di- or polymercapto organic compounds to crosslink the tissue. FIG. 7 is a schematic representation of exemplary steps involved in tissue crosslinking using mercapto compounds, in accordance with an embodiment of the present invention.

In one embodiment, a method of cross-linking a tissue is provided that treats the tissue under effective cross-linking conditions with a di- or polymercapto organic compound.

By "di or polymercapto" is meant any compound including the structure:

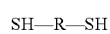

wherein R is an organic moiety having at least 1 carbon atom and SH is a thiol or mercapto group capable reacting with unsaturated carbons such as, by way of example, and not limitation, acrylamide, methacrylamide, acrylate or methacrylate groups. R may have one or more mercapto groups.

Many di- or polymercapto compounds may, for example, and without limitation, be used in tissue crosslinking. The preferred compounds include, but are not limited to, 1,3-propane thiol, 1,4-butane thiol, 1,5-hexane thiol, polyethylene glycol terminated with thiol, trimethylolpropane tris(3-mercaptopropionate), and the like. In one preferred embodiment, the di- or polymercapto organic compound is a trimethylolpropane tris(3-mercaptopropionate).

Preferably, the di- or polymercapto organic compound is a solute in a fluid including a solvent. The fluid including the di- or polymercapto organic compound also includes a solvent. The solvent can be any liquid in which the compound is soluble and in which the compound does not undergo degradation or side reactions. If the di- or polymercapto organic compound is not soluble in water, but is soluble in organic solvents, dimethyl sulfoxide (DMSO) or acetonitrile, for example, may, for example, and without limitation, be used as a co-solvent.

The concentration of the di- or polymercapto organic compound in the fluid is preferably between about 0.1 mg/mL and about 100 mg/mL. More preferably, the concentration is between about 1 mg/mL and about 20 mg/mL.

The pH of the fluid can be any pH which is not deleterious to the tissue being treated or the cross-linking reaction. The pH of the fluid can be adjusted by any appropriate technique. Typically, the pH of the fluid is between about pH 6 and about pH 10. This pH range allows cross-linking to be relatively rapid and have a relatively low amount of side-reactions. Preferably, the pH of the fluid is between about pH 7 and about pH 9. More preferably, the pH of the fluid is between about pH 8 and about 9.

The temperature of the fluid may be any temperature at which the cross-liking reaction is relatively rapid and a relatively low amount of side reactions occur. Preferably, the temperature of the fluid is between about 0° C. and about 45° C. More preferably, the fluid temperature is between about 0° C. and about 30° C. Conveniently, the reaction may be carried out at room temperature about 25 to about 30° C.

One skilled in the art will readily recognize, in light of the teachings of the present invention, that the duration of treatment is not critical, so long as the tissue and the di- or polymercapto organic compound remain in contact long enough for cross-linking to proceed to the desired extent. The duration of treatment may vary depending on the tissue being treated or the di- or polymercapto organic compound being used for cross-linking. Typically, treatment duration is in the range of from about 1 min to about 24 hr. Preferably, treatment duration is at least about 30 min, more preferably at least about 6 hr.

Tissue Crosslinking by Hydrogen Abstraction Mechanism

Aromatic ketones such as, by way of example, and not limitation, benzophenone are known to undergo hydrogen abstraction reaction when exposed to long UV light. In one aspect of the present invention, hydrogen abstraction reaction is exploited for tissue crosslinking. In one embodiment, a method of crosslinking a tissue is achieved by steps that include, without limitation, treating the tissue under effective cross-linking conditions with a crosslinker capable of undergoing hydrogen abstraction reaction; and crosslinking the tissue by hydrogen abstraction mechanism. Surmodics Inc. has commercialized a technology based on hydrogen abstraction reaction for medical device coatings and surface modifications. In one exemplary embodiment (see Example 34 described below), a benzophenone derivative of a polymer (polyethylene glycol terminated with benzophenone) is synthesized. This polymer is then infused into a tissue and the tissue is exposed to long UV light (360 nm). The benzophenone undergoes hydrogen abstraction reaction and crosslinks the tissue. Those skilled in the art of surface modification will readily recognize, in light of the teachings of the present invention, that that many reaction variables can such as, by way of example, and not limitation, polymer concentration, exposure time, light intensity, type of chromophore used may be changed to obtain an effectively crosslinked tissue. Many polymers that can be modified using benzophenone are useful in crosslinking. These include, but are not limited to, polyvinyl pyrrolidinone, heparin, polyvinyl alcohol, polyethylene glycol and their copolymers, and the like. Many different chemicals that undergo hydrogen abstraction reaction could be used. Chemicals that undergo hydrogen abstraction reaction in long UV or visible light range are preferred. One embodiment of the present invention provides for a method for forming a crosslinked tissue including the steps of providing a tissue suitable for human implantation; exposing the tissue to a fluid including a compound capable of reacting with a tissue and undergoing hydrogen abstraction reaction when exposed to light; covalently bonding at least portion of the tissue functional groups with the a compound capable of undergoing hydrogen abstraction reaction when exposed to light; and crosslinking the tissue under effective cross-linking conditions by exposing the tissue to a long UV or visible light.

In addition, proteins in the tissue may be chemically modified using a benzophenone derivative and then crosslinked by exposing to UV light at 360 nm. Benzophenone undergoes hydrogen abstraction reaction upon exposure to UV light and undergoes crosslinking. The crosslinking density can be controlled by amount of benzophenone substituted on the tissue proteins. In one embodiment, the present invention provides for an activated derivative of benzophenone carboxylic acid For example, carboxyl groups of 2-carboxyl benzophenone may be activated by forming n-hydroxysuccinimide ester or -hydroxysulfosuccinimide ester and then reacted with tissue in water (PBS pH 7.2). The benzophenone-modified tissue is exposed to high intensity 360 nm UV light to crosslink the tissue.

Compositions and methods for making biodegradable tissue or tissue/synthetic biodegradable polymer composite materials will next be discussed in some detail.

Tissue Crosslinked Using Degradable Crosslinker

In another aspect of the present invention, a method of cross-linking a tissue that is achieved by steps that include, without limitation, treating the tissue under effective cross-linking conditions with a crosslinker containing biodegradable chemical bonds.

A method is herein provided, by way of example, and not limitation, for cross-linking biological tissues to be used in the production of biodegradable animal tissue based medical devices and controlled drug delivery systems. This is achieved by contacting a biological tissue of interest with one or more of the disclosed compounds under conditions effective to cause the desired degree of tissue cross-linking. The crosslinks in the crosslinked tissue undergo biodegradation when implanted into human or animal body. Upon hydrolysis of the crosslinker, the tissue becomes susceptible to enzymatic degradation and degrades into non-toxic components. One aspect of the present invention is to provide a straightforward approach for producing biodegradable animal tissue-based bioprostheses having desirable mechanical and biocompatibility features and control over degradation of the tissue.

Figure 8:
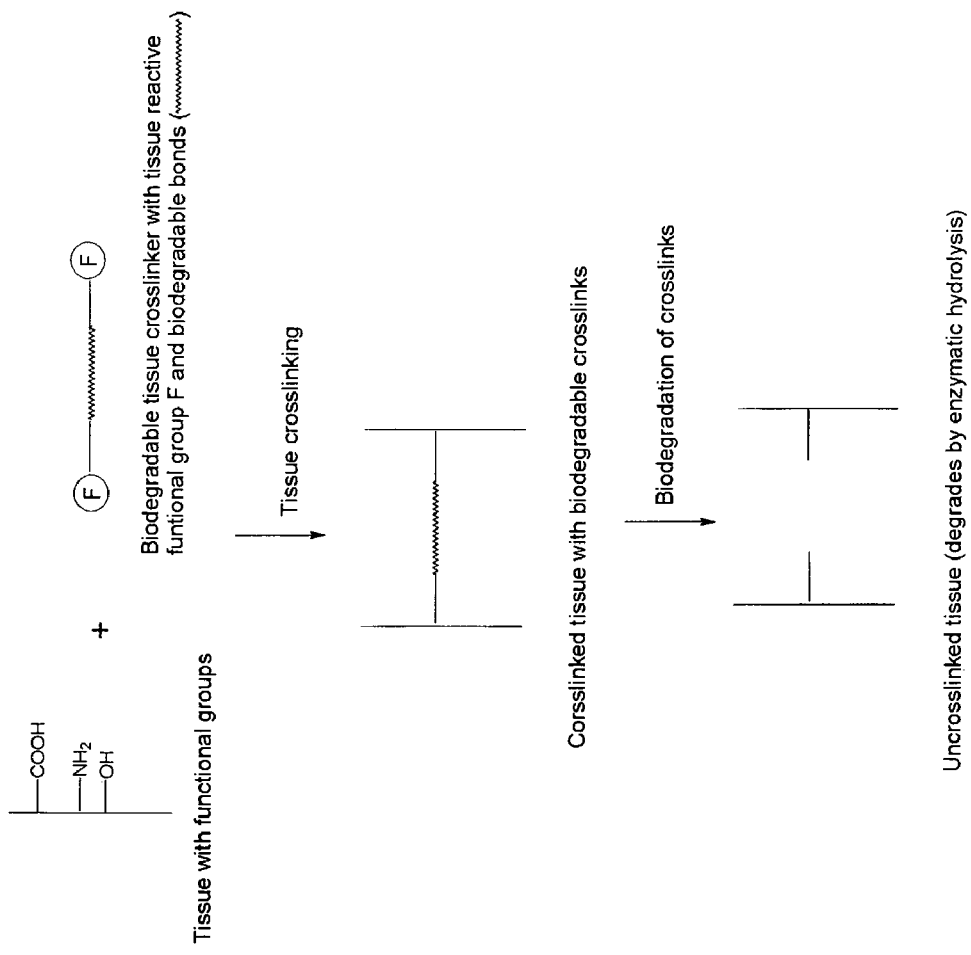
FIG. 8 is a schematic representation of an exemplary tissue crosslinking using biodegradable tissue crosslinker, in accordance with an embodiment of the present invention.

FIG. 8 is a schematic representation of an exemplary tissue crosslinking using biodegradable tissue crosslinker, in accordance with an embodiment of the present invention. The biodegradable crosslinkers compounds suitable for use with this invention can be generally represented by the following structural formula:

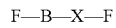

wherein F is a functional group reactive with collagen, elastin or other tissue-based constituents; and X is an organic molecule or radical at the core of the crosslinker. X may include Carbon-Carbon, Carbon-Hydrogen, Carbon-Nitrogen, Carbon-Oxygen, Carbon-Sulfur, Nitrogen-Hydrogen and Oxygen-Hydrogen covalent bonds.

F is a functional group that is sufficiently reactive with the collagen molecules present in the biological tissue to be treated such that the desired chemical bond is formed. For example, functional groups reactive with collagen and suitable for use may include, but are not limited to, anhydride, isocyanate, epoxy, n-hydroxysuccinimide, aldehyde or other protein reactive functionalities known in the art. It is desirable to have two or more functional groups per crosslinker for effective crosslinking.

B is a biodegradable link between two F moieties. "Biodegradable link" denotes a covalent bond or bonds that will degrade in a biological environment by either a biologically assisted mechanism, such as, by way of example, and not limitation, an enzyme catalyzed reaction or by a chemical mechanism which can occur in a biological medium, such as, by way of example, and not limitation, hydrolysis.

The biodegradable linkages B may be chosen such that the resulting biodegradable biocompatible crosslinked will degrade or be absorbed in a desired period of time. Preferably, biodegradable linkages are selected that degrade under physiological conditions into non-toxic products. The biodegradable linkage may be chemically or enzymatically hydrolyzable or absorbable. Illustrative chemically hydrolyzable biodegradable linkages are ester or amide bonds that undergo cleavage under physiological conditions such as, by way of example, and not limitation, found in human body (pH 7.2). Preferred linkages include, but are not limited to, polymers, copolymers and oligomers of glycolide, dl-lactide, 1-lactide, caprolactone, dioxanone, and trimethylene carbonate. Illustrative enzymatically hydrolyzable biodegradable linkages include peptidic linkages cleavable by metalloproteinases and collagenase enzymes. For example, collagen contains peptide sequences susceptible to degradation by collagenease. Crosslinker containing reactive groups and such linkages may be synthesized and used. Additional illustrative biodegradable linkages include polymers and copolymers of poly (hydroxy acid)s, poly(orthocarbonate)s, poly(anhydride)s, poly(lactone)s, poly(aminoacid)s, poly(carbonate)s, and poly(phosphonate)s. Biodegradable linkage may also be non-polymeric; these include, but are not limited to, ester linkages such as, by way of example, and not limitation, succinate, glutarate, itaconate, and the like.

The biodegradable crosslinker preferably contains at least two F moieties and one B moiety per molecule. The number of F groups can be greater than two per molecule and number of B groups can be greater than one per molecule.

Preferred biodegradable crosslinkers include, but are not limited to, activated acid esters such as, by way of example, and not limitation, n-hydroxysuccinimide esters (NHS esters). Some of the preferred protein crosslinkers that can synthesized and used as described according to patent WO 9812274, which is cited here for reference only as one suitable technique. The polyether NHS esters, more preferably polyethylene glycol glutarate, or succinate esters are most preferred.

The cross-linking agents described can be made using any suitable synthetic methodologies including, but not limited to, those known to skilled individuals in the art. One preferred approach involves the use of water soluble polyethylene glycol based activated acid ester is used. In one exemplary embodiment (see Example 19 described below), 10 pieces of 1 cm by 1 cm bovine pericardium tissue are transferred to 50 ml polypropylene centrifuge tube containing 10 ml PBS. 1.0 g 4 arm-n-hydroxysuccinimide ester of polyethylene glycol carboxymethylene-butyric acid, average molecular weight 10000 Daltons (obtained from Shearwater Polymers, 4 arm, product CM-HBA-NS-10K) is added to the tube and the mixture is vortexed for 5 minutes. The tissue is isolated from the tube, washed with distilled water and lyophilized until further use. The glutarate ester bond in CM-HBA-NS-10K undergoes hydrolysis when exposed to physiological conditions such as, by way of example, and not limitation, PBS pH 7.2. After hydrolysis of the crosslinker, the tissue degrades by normal enzymatic pathways. Tissue crosslinked with the 4 arm-n-hydroxysuccinimide ester of polyethylene glycol carboxymethylene-proprionic acid, average molecular weight 10000 Daltons has a shorter degradation time as compared to glutarate ester. Thus, by changing the type of ester linkage, degradation of the tissue can be controlled.

In another illustrative embodiment (see Example 18 described below), a non-polymeric biodegradable crosslinker that is synthesized from hydroxylamine is used. Briefly, the hydroxy amine is first reacted with succinic anhydride. The acid groups formed are then activated by forming n-hydroxysuccinimide ester (NHS ester). The NHS ester is then used to crosslink the tissue. The hydrolysis of succinate ester makes the tissue degradable.

The biological tissue of interest is treated with one or more of the crosslinking agents under conditions effective to cause the desired degree of tissue cross-linking. The skilled individual will recognize, in light of the teachings of the present invention, that the time of treatment is not critical as long as the tissue and cross-linking agent remains in contact for a time sufficient to allow the cross-linking to occur. The time of treatment may vary depending on the type of tissue being treated and/or the particular cross-linking agent used. Typically, the length of the reaction will be from about one minute to one day or more. However, the time of treatment should not be so long as to adversely affect the cross-linked tissue. Thus, cross-linking times greater than about one or two days are generally avoided, though such lengthy times may be appropriate in certain applications. Preferably, the tissue is treated for a period from about one minute to about six hours, more preferably for about one hour to four hours. The degree of cross-linking can to some extent be varied by manipulating the time of the reaction. A reaction temperature is selected to be effective in permitting the desired cross-linking reaction to occur while also being one that does not adversely compromise the integrity of the tissue being treated. The identification of an optimal temperature for a particular agent and/or application can be readily determined by the skilled individual in light of the teachings of the present invention. The cross-linking reaction can generally be successfully carried out at an ambient temperature (20-40° C.), or any other convenient temperature provided it does not exceed the tissue denaturation temperature of about 60 to about 65° C. Thus, a suitable reaction temperature for use in this invention may be from about 0° C. to about 55° C., preferably from about 20° C. to about 50° C., more preferably from about 30° C. to about 40° C. This temperature range is generally applicable to all the tissues treatments described. The tissue is treated under pH conditions that are tissue-stabilizing (i.e., which are not deleterious to the tissue being treated) and which do not adversely effect the tissue cross-linking reaction. This will typically be in a range from about pH 6 to about pH 9. More preferably, the pH will be from about 7.0 and about 8.0. Most preferably, it will be from about 7.0 to about 7.4. The optimal pH may depend to some extent on the cross-linking agent employed, the type of crosslinker being employed, and/or on the tissue being treated, but can be readily determined, in light of the teachings of the present invention, without undue experimentation by the skilled individual in this art. The process of cross-linking biological tissues can be carried out in any suitable solvent. The choice of solvent is generally not critical; however, preferred solvents will typically be aqueous medium with buffering agent. Water-miscible organic solvents that have minimal toxicity to the tissue and/or the recipient, will be non-denaturing and will be compatible with the tissue/protein cross-linking reaction. Some such solvents include, but are not limited to, linear or branched lower alcohols (i.e., having from about one to four carbons); aprotic high polarity organic solvents such as, by way of example, and not limitation, n-methylpyrrolidinone, dimethylsulfoxide, dimethylformamide, dimethylacetamide etc.; lower ketones (i.e., having from about 3 to 6 carbons) such as, by way of example, and not limitation, methyl ethyl ketone or cyclohexanone;

and polyhydroxy compounds such as, by way of example, and not limitation, glycerol, ethylene glycol, or polyethylene glycols having molecular weights less than about 1000.

Figure 9:
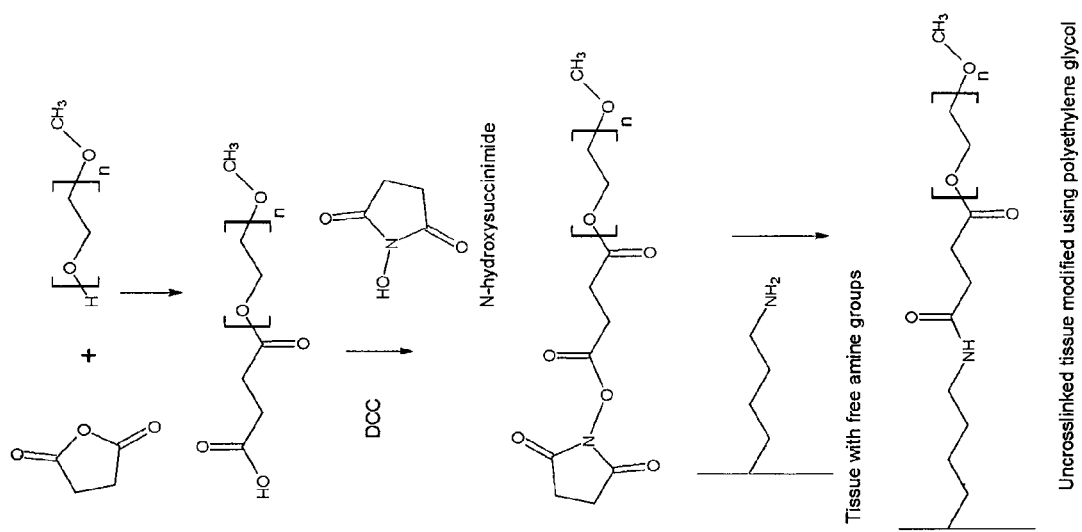
FIG. 9 is a schematic representation of an exemplary biodegradable uncrosslinked tissue modified using polyethylene glycol, in accordance with an embodiment of the present invention.

One embodiment of the present invention provides for a biodegradable absorbable non-crosslinked tissue based implant material including covalently bonding at least a portion of the tissue functional groups with a compound having the formula F—X, wherein F is a functional group reactive with collagen or protein or components in the tissue; preferably free primary amine groups in the tissue and X is an organic molecule covalently linking F and X. X may include Carbon-Carbon, Carbon-Hydrogen, Carbon-Nitrogen, Carbon-Oxygen, Carbon-sulfur, Nitrogen-Hydrogen and Oxygen-Hydrogen covalent bonds. X may polymeric or non-polymeric. For example, and not by way of limitation, the compound F—X may be selected from polyethylene glycol with tissue reactive groups; n-hydroxysuccinimide ester of acetic acid, n-hydroxysuccinimide ester of acrylic acid, polyethylene glycol monomethoxy alcohols modified with acid group, n-hydroxysuccinimide ester of methacrylic acid; acrylic anhydride; acetic anhydride; n-hydroxysuccinimide ester of triiodobenzoic acid; succinic anhydride, glutaric anhydride, acetyl chloride; acrolein, methacrolein, lactide, glycolide, methyl isocyanate, phenyl isocyanate, glycidyl methacrylate, and glycidyl acrylate. FIG. 9 is a schematic representation of an exemplary biodegradable uncrosslinked tissue modified using polyethylene glycol, in accordance with an embodiment of the present invention. The method shown is suitable for obtaining a biodegradable uncrosslinked tissue modified with polyethylene glycol.

Animal Tissue and Synthetic Biodegradable Polymer Composites

The present invention provides for novel methods and compositions for materials that combine the properties of animal tissue and synthetic or semisynthetic biodegradable polymers, copolymer and oligomers. In one embodiment, the present invention provides for a method for forming an animal tissue and synthetic biodegradable polymer composite implant including the steps of providing a tissue suitable for human implantation; exposing the tissue to a fluid including a biodegradable polymer dissolved in the solvent; and evaporating the solvent. In an alternate embodiment, the tissue is exposed to a fluid including biodegradable polymer dissolved in the solvent and a therapeutic or bioactive substance dispersed in the solvent. In another alternate embodiment, the present invention provides for a method for forming an animal tissue and synthetic biodegradable polymer composite including the steps of providing a tissue suitable for human implantation; exposing the tissue to a fluid including biodegradable crosslinkable polymer dispersed in the solvent; evaporating the solvent; and crosslinking the biodegradable polymer. In these various embodiments, the tissue may be dehydrated. Additionally, the biodegradable polymer may be hydrophilic or hydrophobic.

Animal tissue such as, by way of example, and not limitation, bovine pericardium has unique mechanical properties such as, by way of example, and not limitation, excellent fatigue resistance and durability. However, animal tissues have found little utility in delivering bioactive compounds, especially water soluble compounds, in a controlled manner. A composite material including synthetic biodegradable polymer and animal tissue is discussed herein. Methods of such composite preparation as well as their medical applications are discussed herein. Compositions and methods that physically or chemically bound synthetic biodegradable polymers to the tissue are also discussed herein.

In one illustrative and preferred embodiment (see Example 22 described below), the animal tissue is dehydrated by exposing it to a series of aqueous ethanol solutions. The dried tissue is then added to a solution of synthetic biodegradable polymer in an organic solvent incubated for sufficient amount of time until the polymer solution penetrates the tissue matrix. The polymer solution may include biologically active compound. The tissue is removed from the solution and the polymer solvent is evaporated or removed by extraction with other solvents. The tissue-biodegradable polymer composite may, for example, and without limitation, be used in variety of medical and surgical applications. The tissue may be mechanically or chemically treated to improve adhesion of biodegradable polymer to the tissue. Mechanical modification may involve, for example, creating perforations, microporosity to mechanically interlock the biodegradable polymer in the tissue matrix. The molecular weight of biodegradable polymer may vary form 1000 to 1 million g/mole, most preferably from 2000 to 500000 g/mole and even more preferably from 5000 to 150000 g/mole. The amount of polymer incorporated in the tissue may range from 1% to 70%, more preferably 5% to 30%.

The animal tissue used may be biostable or biodegradable. The animal tissue used may be crosslinked or non-crosslinked. The animal tissue used may be crosslinked using conventional crosslinking technique such as, by way of example, and not limitation, EDC crosslinking or glutaraldehyde crosslinking methods known in the heart valve biosprosthesis art. The animal tissue may be non-crosslinked or chemically modified without crosslinking. This includes tissue like porcine sub-mucosa tissue or non-crosslinked but chemically treated tissue. Membrane-like biodegradable tissue is most preferred for controlled drug delivery applications. In many medical device applications where biodegradable tissue is needed, a non crosslinked tissue, EDC crosslinked tissue or tissue crosslinked using biodegradable crosslinker as discussed previously may, for example, be used. Applications were biostable tissue is needed, then glutaraldehyde or di or polyepoxide crosslinked tissue may, for example, be used.

The bioabsorbable or biodegradable polymers used in this invention include any polymer that degrades into non-toxic products upon degradation and may include, but are not limited to, polymers, oligomers or copolymers generally known as polylactones or polyhydroxy acids; polylactones such as, by way of example, and not limitation, polylactide poly-L-lactide (PLLA), poly-D-lactide (PDLA), poly-DL-Lactide (PLA), polyglycolide (PGA), polylactide-polyglycolide copolymers; polydioxanone, polycaprolactone (PCL), Polyhydroxyalkanoates are polyesters produced by microorganisms such as poly(3-hydroxybutyrate), 3-hydroxyvalerate, 4-hydroxybutarate, 3-hydroxyhexanoate, 3-hydroxyoctanoate can also be used. Polycaprolactone-polyglycolide copolymers, polylactone-polyethylene oxide copolymers are preferred. Modified cellulose, polylactones collagen, poly (hydroxybutyrate), polyanhydride, polyphosphoester, poly (amino acids), poly(alpha-hydroxy acid) or related copolymers materials, each of which have a characteristic degradation rate in the body, may also be used. For example, polyglycolide and polydioxanone copolymers degrade in weeks to months. PLA degrades in months to few years and polycaprolactone degrades in few years. Their copolymers have intermediate degradation times depending on the composition of the copolymer. The biodegradable polymer may be linear, branched, star type. The biodegradable polymer may be block or random copolymer or may be blend of two are more polymers. The block copolymers include, but are not limited to, ABA type, BAB type or AB type block copolymers. Bioabsorbable polymers such as, by way of example, and not limitation, PLLA, PDLA, PGA and others are commercially available from several sources including PURAC America, Inc.; Aldrich, Polysciences, and Birmingham Polymers. The biodegradable polymer may be in a variety of forms, for example, liquid, solid, semi solid, wax type or gel type when incorporated in the tissue.

Figure 10:
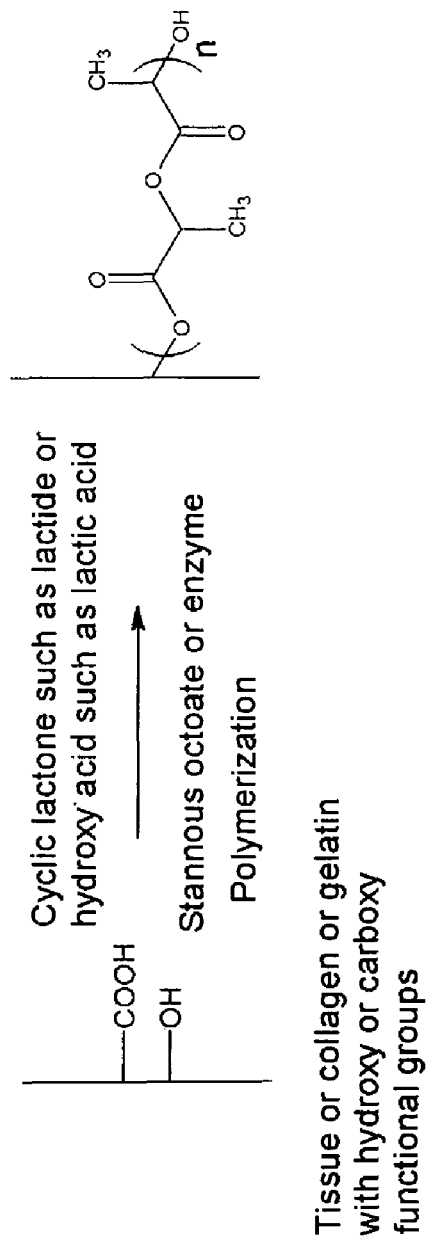
FIG. 10 is an exemplary reaction scheme for tissue or collagen modification with polyhydroxyacid or polylactones, in accordance with an embodiment of the present invention.

The biodegradable polymer may be covalently linked to the tissue. Many methods of covalently bonding the polymers may, for example, and without limitation, be used. One preferred and illustrative reaction scheme is shown in FIG. 10. In one preferred and exemplary embodiment (see Example 39 or 40 described below), the hydroxy groups of proteins in the tissue or collagen matrix may, for example, and without limitation, be used to initiate polymerization of cyclic lactones or carbonates. The cyclic lactones that may, for example, and without limitation, be used include, but are not limited to, lactide, glycolide, caprolactone, dioxanone, trimethylene carbonate, and the like. Two or more lactones may be copolymerized to obtain a desirable degradation profile of the composite material. The polymerization is usually, though not necessarily, catalyzed by metal organic catalysts such as, by way of example, and not limitation, stannous octoate. The concentration of catalyst added may depend on the catalyst used. Enzymatic catalysts or biological enzymes that promote esterification may also be used. Preferred catalyst stannous octoate is generally added in the range of about 100 ppm to 10000 ppm relative to cyclic lactone concentration. The polymerization reaction may be carried out in a suitable solvent or under melt conditions to obtain a desired molecular weight of the polylactone. Many commonly used organic solvents can be used, but solvents that do not denature the proteins in the tissue are preferred. Preferred commonly used organic solvent solvents include, but are not limited to, acetone, tetrahydrofuran, benzene, toluene, xylene, chloroform, methylene chloride, dimethyl sulfoxide, dimethylacetamide, and the like. The preferred temperature is chosen that promotes rapid polymerization over a period of about 7 days, more typically in about 2 days even more typically in about a few hours. If using a tissue, polymerization temperature below shrink temperature is most preferred. The shrink temperature of uncrosslinked tissue is generally around about 60° C. and crosslinked tissue is around about 70-100° C. Polymerization conditions using temperatures below about 60° C. are most preferred. Lower temperature usage generally requires longer polymerization times. The molar ratio of hydroxy groups in the tissue to lactone may, for example, and without limitation, be used to control the degree of polymerization of cyclic lactones. For high molecular weight polymers, a higher ratio of cyclic lactone to hydroxy groups in tissue may, for example, and without limitation, be used. The molar ratios (cyclic lactone/hydroxy groups) may vary from about 1 to about 500 depending on the final molecular weight desired. A molar ratio of about 1 to 50 is generally preferred. In one embodiment, lactide polymerization was initiated by tissue or solid collagen sponge using THF as a solvent and stannous octoate as a catalyst. The tissue-polylactide composite has a different degradation profile than this tissue. The pepsin digestion data for dl-lactide modified tissue is given in Table 4.

TABLE 4

Pepsin digestion data on dl-lactide modified tissue

| Tissue treatment | Pepsin digestion | Visual Observations |
|---|---|---|
| Bovine pericardium untreated control | Completely degraded in 6 hours. | Complete dissolution |
| Bovine pericardium, treated with dl-lactide in presence of stannous octoate | 45% reduction in 51 hours | Partial digestion after 51 hours |
| Bovine pericardium crosslinked with glutaraldehyde, treated with dl-lactide in presence of stannous octoate | No degradation | No change in tissue appearance. |

The data in Table 4 indicates that the uncrosslinked tissue treated with dl-lactide showed substantial stability towards enzymatic degradation as compared to untreated tissue which degraded in 6 hours. However dl-lactide treated tissue lost 45% weight in 51 hours indicating its susceptibility to enzymatic degradation. Thus, it is expected that the dl-lactide tissue can resist degradation much longer than the untreated tissue and thus stay much longer than untreated tissue once implanted in the body. As expected, glutaraldehyde treated tissue shows higher stability towards enzymatic degradation. Collagen based films, fiber mats, sponge, porous scaffolds may also be modified using cyclic lactones.

In another embodiment, dl-lactide polymerization was initiated by gelatin or collagen to produce a gelatin-polylactide graft copolymer. The composite degrades by hydrolysis and an enzymatic degradation mechanism. The degradation of synthetic polymer will depend on cyclic lactone used. In general, polyglycolide degrades in about a few months, polydl-lactide in about 6 to 18 months, and polycaprolactone in about a few years. Their copolymers may, for example, and without limitation, be used to achieve intermediate degradation times. The synthetic polymer may, for example, and without limitation, be used to entrap a bioactive compound inside the biodegradable polymers. Techniques such as, by way of example, and not limitation, solvent diffusion may, for example, and without limitation, be used to diffuse or entrap drugs in the degradable polymer matrix in the composite material.

The biodegradable polymers may be hydrophobic or hydrophilic. The biodegradable polymers may be crosslinked or non-crosslinked. The hydrophobic polymers include, but are not limited to, polymers, copolymers or oligomers of glycolide, dl-lactide, d-lactide, l-lactide, caprolactone, dioxanone and trimethylene carbonate; polyhydroxyacids, polylactic acid, polyglycolic acid, polyanhydrides, and polylactones. Hydrophobic polymers also include polyhydroxyalkanoates which are polyesters produced by microorganisms such as poly(3-hydroxybutyrate), 3-hydroxyvalerate, 4-hydroxybutarate, 3-hydroxyhexanoate, 3-hydroxyoctanoate. Preferred hydrophilic polymers include, but are not limited to, polyethylene glycol-polyhydroxy acid or polyethylene glycol-polylactone copolymers (PEG-PL copolymers), polyvinyl alcohol co-polylactone copolymers, and derivatives of cellulose, hyaluronic acid and dextran. The PEG-PL copolymers are most preferred. PEG-PL copolymers such polyethylene glycol-polylactone copolymers can have a range of properties from hydrophobic to hydrophilic depending on the amount of PEG incorporation in the copolymer and molecular weight of PEG and polylactone. PEG incorporation that gives up to about 5-70 percent water absorption is preferred. The PEG-PL copolymers with PEG molecular weight about 400 to about 30000 Daltons are preferred. In one exemplary embodiment (see Example 21 described below), a PEG molecular weight 8000 (Carbowax 8000) is used in the polymerization of dl-lactide using stannous octoate as a catalyst. The polymerization reaction is carried out for 16 h at 160° C. The polymer is isolated and incorporated in the tissue (PEG8K50). Briefly, a membrane-like tissue such as, by way of example, and not limitation, pericardial tissue is incubated for 30 minutes each in 20 percent ethanol, 40 percent ethanol, 80 percent ethanol, and finally in 100 percent ethanol to dehydrate the tissue. The tissue may also be dehydrated by lyophilization. The dehydrated tissue is then transferred into polyethylene glycol-lactate copolymer (PEG8K50) and rifampin solution in chloroform and incubated for 2 hours. The tissue is removed from the solution and the solvent is evaporated by air drying. The reddish yellow rifampin-PEG-lactate polymer is clearly visible to the naked eye. The dry tissue is sterilized using ethylene oxide and used as a biodegradable drug delivery patch. The polyethylene glycol-lactate polymer in the tissue acts as a hydrophilic biodegradable polymeric drug delivery matrix for Rifampin.

The biodegradable polymer incorporated into the tissue may be crosslinked in nature. The crosslinked polymer may be hydrophilic or hydrophobic. It is preferred that the crosslinking reaction is carried out after infusion of precursor polymers in the tissue. This permits better distribution of polymer in the tissue matrix. In one exemplary embodiment (see Example 15 described below), a hydrophobic free radically polymerizable liquid precursor is made by initiating the polymerization of lactide using trimethylol propane triol and then endcapping the terminal hydroxyl groups with acrylate end groups. This polymerizable precursor is then infused in the tissue along with photoinitiator and vinyl pyrrolidinone as comonomer using chloroform as a solvent. After the solvent removal, the lactide precursor is photopolymerized exposing the tissue to long wavelength light. In another variation (see Example 20 described below), a water-soluble precursor based on polyethylene glycol is incorporated into the tissue first and then crosslinked. If a bioactive compound such as, but not limited to, heparin, rifampin, or growth factor is mixed prior to crosslinking, then the compound remains entrapped in the crosslinked polymer and is then released slowly upon degradation of biodegradable crosslinked polymer.

Radio-opaque implantable tissue Animal tissue such as, by way of example, and not limitation, porcine pericardium or bovine pericardium is poorly visible when viewed using standard medical x-ray imaging techniques. This is probably due to poor absorption of x-rays by the components of the tissue. In many medical device applications, especially in surgical procedures which are done using x-ray fluoroscopic techniques; it is desirable to have an implantable tissue that can be differentiated from surrounding tissue when implanted and viewed under standard medical x-ray imaging technique. A radio-opaque tissue can be easily seen when viewed using standard medical x-ray imaging technique. This invention provides compositions and methods for making radio-opaque implantable tissue. Some of the preferred methods for making implantable radio-opaque tissue are given below.

Implantable animal tissue may be chemically modified using a reagent including at least one functional group capable of reacting with tissue (F) and at least one radio-opaque chromophore capable of absorbing x-rays (M). The chemical modification agents used in accordance with an embodiment of the present invention include an organic functional molecule with at least one functional group capable of reacting with tissue and at least one radio-opaque chromophore. Thus, the compounds suitable for use with this invention can be generally represented by the following structural formula:

F—X-M wherein F is a functional group reactive with collagen or protein or components in the tissue; preferably free primary amine groups in the tissue; X is an organic molecule/radical covalently linking F and X. X may include Carbon-Carbon, Carbon-Hydrogen, Carbon-Nitrogen, Carbon-Oxygen, Carbon-Sulfur, Nitrogen-Hydrogen and Oxygen-Hydrogen covalent bonds. X may polymeric or non-polymeric.

M is a chromophore that can absorb x-rays. The preferred chromophores include, but are not limited to, phenyl ring compounds such as, by way of example, and not limitation, 2,3,5-triiodobenzoic acid, 3,4,5-triiodophenol, erythrosine, rose bengal, 3,5-Bis(acetylamino)-2,4,6-triiodobenzoic acid, 3,5-Diacetamido-2,4,6-triiodobenzoic acid, heavy metal ion complexes, and the like. The iodine in these compound may be radioactive if desired. A radioactive ($I^{125}$ or $I^{131}$) could be potentially used for local radiation therapy.

F is a functional group that is sufficiently reactive with the collagen molecules present in the biological tissue to be treated such that the desired chemical bond is formed. For example, functional groups reactive with collagen and suitable for use may include, but are not limited to, anhydride, isocyanate, n-hydroxysuccinimide, n-hydroxysulfosuccinimide, epoxy, aldehyde or other collagen reactive functionalities known in the art. It is desirable to have only one F moiety per molecule to avoid crosslinking of proteins in the tissue. If crosslinking is desired, more than 1 F moiety may, for example, and without limitation, be used.

Preferred molecules which are capable of modifying the tissue include, but are not limited to, activated monofunctional triiodobenzene derivatives such as, by way of example, and not limitation, n-hydroxysuccinimide esters or n-hydroxysulfosuccinimide esters of triiodobenzoic acid or erythrosin.

The tissue modification using reagents, which are taught by way of example in the present detailed description, can be made using any suitable synthetic methodologies, including but not limited to, those known to skilled individuals in the art. In one embodiment of the present invention a method of modifying the issue is achieved by steps that include, without limitation, treating the tissue under effective modification conditions with a monofunctional tissue reactive iodinated organic compound. In one exemplary embodiment (see Example 36 described below), bovine pericardium tissue is modified with triiodobenzoic acid succinimide ester (TIBA-NHS). The modification method includes exposing the tissue to a fluid including reactive iodinated compound that can react with amino groups in the tissue under mild conditions. As used herein, the term "activated" as applied to an acid moiety-containing compound containing an additional moiety such that the activated acid can react with amino groups under mild conditions. Preferred activating moieties include, but are not limited to, disuccinimidyl moieties, n-hydroxy disuccinimidyl moieties, sulfo-disuccinimidyl moieties, and mixtures thereof. Briefly, bovine pericardium pieces, cut from a freshly obtained bovine pericardial sac, are treated with TIBA-NHS dissolved in dimethyl sulfoxide or PBS buffer. The reaction is carried out in aqueous medium buffered with PBS (pH 7.2). The modification reaction is carried out for 6 hours at ambient temperature (25° C.) and then for 12 hours at 4° C. with gentle shaking. Some NHS esters such as, by way of example, and not limitation, acetic acid NHS esters are sparingly soluble in water therefore a solubility enhancing compound such as, by way of example, and not limitation, dimethyl sulfoxide may, for example, and without limitation, be used to facilitate the reaction between activated acid groups and primary amine groups on the tissue. The reaction occurs in mild conditions, in water (PBS and at pH 7.2) and is usually complete in about 24 hours, more preferably within about six hours. It can also be substantially completed in about 10 minutes and therefore may permit the use of this method in the operating room during a surgical procedure to modify an autologous tissue. In another variation of this method, the modification reaction may be carried out under mild acidic conditions (MES buffer, pH 6.5). In this case, the NHS ester is added every 1.5 hours to replace the hydrolyzed NHS ester. (NHS ester is deactivated by reaction with water). The NHS groups react with primary amines groups of the tissue forming stable amide bonds. The NHS ester reacts with primary amines groups on the tissue. Reaction variables such as, by way of example, and not limitation, time, temperature, concentration, pressure may be controlled in such a way that about 1 to about 100 percent primary amine groups on the tissue are modified. More preferably, about 10 to about 95 percent amine groups are modified, even more preferably about 40 to about 95 percent amine groups are modified.

In another approach, triiodobenzoic acid is reacted with tissue using 1-Ethyl-3-(3-dimethylaminopropyl) carbodiimide hydrochloride (EDC) as a catalyst. EDC promotes the reaction between carboxylic acid of triiodobenzoic acid and OH and primary amine groups present in the tissue. EDC treatment also results into crosslinked non-cytotoxic tissue. Aqueous medium, more specifically buffered medium, with pH about 5.5 to about 7.5 may, for example, and without limitation, be used for such reactions. A co-catalyst such as, by way of example, and not limitation, n-hydroxysuccinimide or n-hydroxysulfosuccinimide may also be used to accelerate the coupling reaction. Using a similar approach, other biocompatible hydrogels such as, by way of example, and not limitation, hyaluronic acid, chitosan and alginate may also be made radio-opaque and are considered part of the present invention.

In another approach, a radio-opaque polymerizable monomer may, for example, and without limitation, be used in polymerization and crosslinking as discussed above. For example, a polymerizable radio-opaque monomer may be obtained by esterification of triiodobenzoic acid and 2-hydroxyethyl methacrylate. The radio-opaque ester may be copolymerized and crosslinked with unsaturated group modified tissue.

In another approach, heavy metal biocompatible salts such as, by way of example, and not limitation, silver salts may be deposited in the tissue to make it radio-opaque. Many methods for silver salt incorporation can be used. In one exemplary embodiment, a tissue is first exposed to silver nitrate solution by dipping the tissue and removing the tissue and then exposing to sodium acetate or sodium iodide or sodium chloride solution. The exposure to acetate or chloride ions form insoluble salts inside the extracellular matrix of the tissue and leach out over a period of time. The silver salts provide visibility in x-ray based medical imaging equipment.

Tissue used in modification may be crosslinked or non-crosslinked. A non-crosslinked tissue generally yields biodegradable implantable tissue. A glutaraldehyde crosslinked tissue gives biostable tissue.

The tissue also may be coated with polymeric compositions including radio-opaque compounds. For example, biodegradable polymers such as, by way of example, and not limitation, poly(lactic acid) and x-ray contrast agent such as, by way of example, and not limitation, iohexyl are dissolved in common organic solvent such as, by way of example, and not limitation, dimethyl sulfoxide or tetrahydrofuran and the solution may be spray-coated on the tissue. Upon solvent removal, iohexyl remains entrapped in the polymeric coating which makes the tissue radio-opaque.

The radio-opaque tissue may, for example, and without limitation, be used to fabricate many and varied medical devices. The medical devices may be existing medical devices such as, by way of example, and not limitation, a heart valve or a vascular graft or devices that are yet to be developed. More specifically, radio-opaque tissue may, for example, and without limitation, be used to fabricate tissue covered coronary or vascular stents or stent grafts. The visibility of radio-opaque tissue permits localized drug or device therapy using standard techniques used in MIS surgery. This radio-opaque tissue may be subjected to additional treatments such as, by way of example, and not limitation, anti-calcification treatments known in the prior art.

In some applications, modified non-crosslinked radio-opaque tissue is expected to undergo degradation after in vivo implantation. The modification compounds and their degradation products/components must be able to be eliminated from the host body. The modification compounds may be chosen such that the resulting biodegradable biocompatible crosslinked tissue will degrade or be absorbed in a desired period of time. Preferably, modification reagents are selected in a manner that it will degrade under physiological conditions into non-toxic products.

In applications where biodegradable tissue is desired, the tissue may be heat-treated to make it denatured. Such denaturing is done to accelerate the degradation of the tissue. The denaturing may be done by heating a membrane-like tissue such as, by way of example, and not limitation, porcine pericardium in saline solution and holding it in the temperature range of about 70 to about 100° C. (above shrink temperature) for about 1 minute to about 24 hours, more preferably from about 1 minute to about 30 minutes.

Coated Bioprosthetic Tissue Compositions and Methods

Properties of biological tissue surface can be changed by applying different types coatings. For example, the glutaraldehyde fixed tissue surface is cytotoxic and does not support cell growth. A surface coating that eliminates the surface toxicity is highly desirable. Non-crosslinked tissues such as, by way of example, and not limitation, pericardial tissue supports cell growth and degrade by enzymatic process when implanted in the human or animal body. In some applications, such as, by way of example, and not limitation, prevention of post operative adhesions or hernia repair application, a barrier surface that is hydrophilic, biocompatible but does not support cell growth is desirable. A polyethylene glycol based hydrogel on tissue surface may provide such non-cell adhesive surface.

Figure 11:
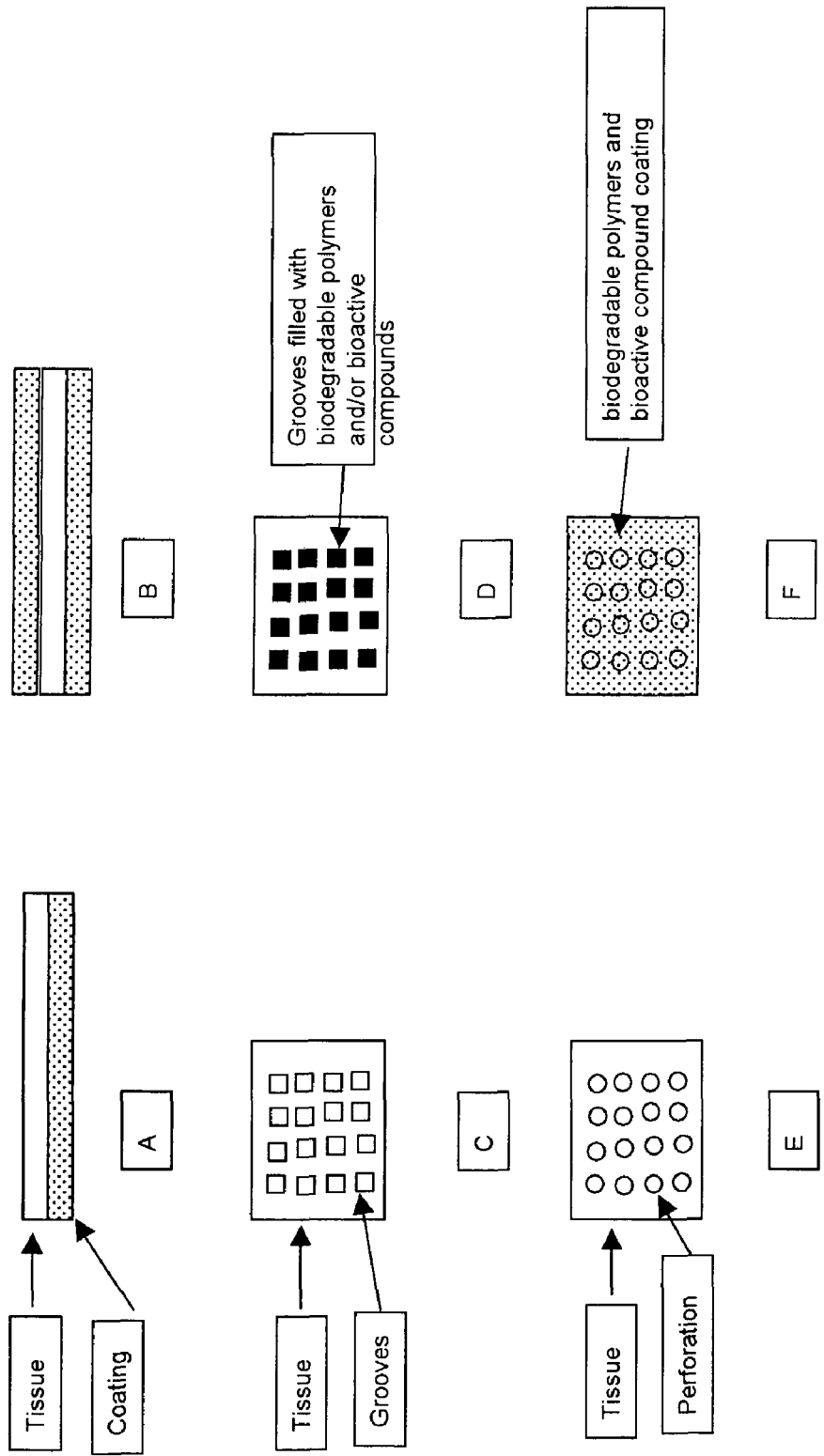
FIG. 11 is a schematic representation of an exemplary membrane-like tissue modifications (A-F), in accordance with an embodiment of the present invention.

In one aspect of the present invention, various coating compositions that can be applied on the implantable tissue surface are provided. The coating may cover all surface areas of the tissue or may be applied on some parts of the tissue. FIG. 11 is a schematic representation of an exemplary membrane-like tissue modifications (A-F), in accordance with an embodiment of the present invention. Illustrated in the Figure are various modifications of membrane-like implantable tissue. FIGS. 11A and B illustrate the coating of a membrane-like tissue such as, by way of example, and not limitation, bovine pericardium from one and both sides. The coating may include, for example, cells and/or bioactive compounds. The coating may also be a biodegradable biocompatible hydrogel. Multiple layers may also be utilized. Methods for forming such coated tissue surfaces and their biomedical applications such as, by way of example, and not limitation, barrier for post operative adhesion prevention and controlled drug delivery are also described.

In some embodiments, the tissue is coated using a biodegradable polymer. The coated tissue structure is schematically shown by way of example in FIG. 11. The coating thickness may be about 0.1 microns to about 5 mm thick. More preferably the coating may be about 5 micron to about 2 mm thick. The biodegradable coating may degrade in approximately days to years. The degradation time will depend on the type of biodegradable polymer used in the coating. For example, a coating based on polyglycolide polymers and copolymers may degrade in weeks to months, PLA or PLA-PGA coating will degrade in months to years, and polycaprolactone based coating will degrade in years. An elastomeric coating formed from biodegradable polyurethanes may also be used. The coating may have biologically active compounds encapsulated in the polymer. The coatings also may have cells such as, by way of example, and not limitation, stem cells incorporated in the coating. The hydrophilic coatings include biodegradable hydrogel coatings formed by crosslinking and polymerization of polyethylene glycol based water soluble macromonomers. In one such illustrative embodiment (see Example 23 described below), a polyethylene glycol based macromer is first synthesized. An aqueous solution of macromer is then polymerized on the tissue to form a thin hydrogel coating.

In another embodiment of the present invention, a synthetic biodegradable hydrogel is coating is formed by condensation polymerization (see Example 24 described below). Briefly, the hydrogel is formed by mixing reactive precursor species including nucleophilic functional groups and reactive precursor species including electrophilic functional groups. In one exemplary embodiment, solutions of polyethylene glycol NHS derivatives and dilysine are sprayed and polymerized on the 10 cm×5 cm bovine pericardial sac. The solutions of polyethylene glycol NHS derivatives and dilysine are commercially sold under the trade name of DuraSeal™ by Confluent Surgical, Waltham, Mass. DuraSeal™ sealant can also be used to make a coated tissue. The DuraSeal™ coating may be applied just prior to implantation. Alternatively tissue such pericardial patch tissue and DuraSeal™ product and spray systems may be supplied as a kit to make a coated tissue product in the surgical suit. The tissue used may be non-crosslinked (biodegradable) or crosslinked (biostable). For example, AlloDerm® a processed human skin tissue marketed by LifeCell corporation may be coated using DuraSeal™ and used. In another embodiment of the present invention, a tissue is first dehydrated by lyophilization or using other techniques known in the art. The precursors may be applied as a dry powder without crosslinking. Upon application on the surgical site, the precursor powder coated tissue undergoes hydration and crosslinking.

In another embodiment of the present invention, a tissue is first dehydrated by lyophilization or using other techniques known in the art. A biodegradable polymer dissolved in organic solvent is sprayed on the tissue surface. Alternatively the polymer may be coated using a dip coating method. The solvent is removed and the polymer coated tissue is recovered and stored appropriately. The coating may be applied on one side or on both sides.

A non-crosslinked tissue such as, by way of example, and not limitation, bovine pericardial tissue typically degrades in 4 months when implanted subcutaneously in the rat body. Control over tissue degradation time is highly desirable. A polymeric biodegradable coating on the tissue may temporarily restrict the access of degradative enzymes when implanted in the body. After the coating is resorbed due to biodegradation processes in the body, the access of enzymatic degradative sites in the tissue is restored and the tissue is degraded. Thus, coatings may help to lengthen the degradation time of the non-crosslinked biodegradable tissue. By choosing a biodegradable polymer that degrades from months to years, biodegradation of the tissue may be varied from months to years. The polymer coating may be loaded with drug for a local or systemic therapeutic effect.

The coating in the degradable polymer-coated tissue, which are taught by way of example in the present detailed description, may be supplemented with collagenease, pepsin or other protease enzymes which can accelerate tissue degradation. The enzyme is released from the coating in a controlled manner which then degrades the tissue. This approach may, for example, and without limitation, be used to accelerate the tissue degradation.

The tissue-synthetic biodegradable polymer composite material or coated product produced according to the present invention can be modified further, if necessary or desired, by the addition of any pharmaceutically acceptable compound or agent such as, but not limited to, antioxidant, plasticizer, coloring agent, x-ray or MRI imaging agent, filler such as, by way of example, and not limitation, calcium phosphate salts and the like.

Another aspect of the present invention is that the tissue based materials described can be used to deliver biologically active compounds. The composite/coated material will deliver a therapeutically effective amount of bioactive substance in a controlled manner. In one embodiment, rifampin, a commonly used antibiotic is incorporated in the tissue-biodegradable polymer composite material. Small organic and inorganic molecules as well as large molecules such as, by way of example, and not limitation, proteins, carbohydrates, organic molecules, synthetic peptides, genes, antibodies, enzymes, etc. can be used. Some examples of bioactive compounds that can be released inside the human or animal body include, but are not limited to, antiviral agents; antiinfectives such as, by way of example, and not limitation, antibiotics; antipruritics; antipsychotics; cholesterol or lipid reducing agents, cell cycle inhibitors, anticancer agents, antiparkinsonism drugs, HMG-CoA inhibitors, antirestenosis agents, antiinflammatory agents; antiasthmatic agents; antihelmintics; immunosuppressives; muscle relaxants; antidiuretic agents; vasodilators such as, by way of example, and not limitation, nitric oxide or nitric oxide adducts; beta-blockers; hormones; antidepressants; decongestants; calcium channel blockers; growth factors such as, by way of example, and not limitation, bone growth factors, bone marrow proteins, vascular endothelial growth factor, platelet derived growth factor, acidic growth factors, basic growth factors, wound healing agents, analgesics and analgesic combinations; local anesthetics agents, antihistamines; sedatives; angiogenesis promoting agents; angiogenesis inhibiting agents; tranquilizers, and the like. In many instances, the duration of the drug release is affected by the hydrophobicity of the drug and polymer, drug loading and polymer composition and polymer degradation characteristics. The amount of bioactive compound incorporated in the tissue composite materials is in the range of about 0.1 percent to about 90 percent, more preferably in the range of about 5 to about 70 percent, and even more preferably in the range of about 10 to about 50 percent. In some cases, two or more bioactive compounds may, for example, and without limitation, be used to achieve a desirable therapeutic effect.

In a biodegradable drug delivery patch application, membrane-like tissues such as, by way of example, and not limitation, porcine pericardial tissue, processed human skin tissue (AlloDerm®), bovine pericardial tissue or porcine sub-mucosa tissue are preferred. The animal tissue may be crosslinked or non-crosslinked. A non-crosslinked tissue may, for example, and without limitation, be used if an absorbable patch material is desired. A drug delivery patch could be formulated to incorporate a bioactive compound. The patch will deliver a therapeutically effective amount of bioactive substance in a controlled manner. The patch may be coated with biodegradable hydrogels encapsulated with cells or bioactive growth factors. The patch can be utilized to deliver a drug or bioactive compound systemically or locally. In one embodiment, the present invention provides for a method for localized drug delivery including the steps of providing a sterile tissue suitable for human implantation; providing a sterile biodegradable polymer; providing a sterile solvent for biodegradable polymer; dissolving the biodegradable in the solvent and optionally adding bioactive compound; exposing the tissue to a polymer solution; forming a coating of polymer on the tissue; and implanting the tissue.

This invention also anticipates the use of non-polymeric liquid/solids as coating materials for the tissue and as controlled drug delivery matrices incorporated into the tissue. The non-polymeric materials used to coat the tissue or to form a composite material include biocompatible non-polymeric liquids and solids which can be implanted in the human body. These non-polymeric materials include those that have a history of human use. These include, but are not limited to, wax materials such as, by way of example, and not limitation, bone wax, fatty acids and their derivatives such as, by way of example, and not limitation, stearic acid and oleic acid, sugar derivative such as, by way of example, and not limitation, sucrose acetate, mineral oil, peanut oil, cotton seed oil, tocopherol, polyethylene glycol, and the like. PEG-Polylactone based copolymers with melting below 60° C. are most preferred in this application.

Animal tissue, preferentially a biodegradable tissue, can be used as carrier for biologically active substances such as, by way of example, and not limitation, sparingly water-soluble drugs without the use of carrier. Some examples of such drugs include, but are not limited to, chlorhexidene acetate, chlorhexidene gluconate, lovastatin, simvastatin, paclitaxel, silver iodide, silver acetate, silver lactate, and the like. In one embodiment, chlorhexidene acetate or chlorhexidene gluconate is incorporated in the tissue using a solvent method. Briefly dehydrated tissue is exposed to an organic solvent or semi aqueous solvent such as water alcohol mixture in which the drug is dissolved. The solvent is removed and crystals of drug are formed inside the tissue matrix. These crystals serve as reservoir for the drug to be released. The drug is released due to slow dissolution of drug crystals. In another embodiment, poorly water soluble silver salts such as, by way of example, and not limitation, silver chloride, silver iodide, silver acetate, silver lactate and the like are precipitated inside the tissue or extracellular matrix by a reaction of two solutions. After precipitation, sparingly soluble silver salts release silver ions from the tissue matrix providing antimicrobial activity to the tissue. Depending on the solubility, different silver salts such as, by way of example, and not limitation, silver iodide, silver acetate, silver lactate and the like may be chosen to have different silver ion release profiles. Silver salts can be deposited using many methods such direct salt deposition, ion beam implantation and the like. In a preferred embodiment, silver salts are formed in situ inside the tissue. In one preferred embodiment, tissue is first exposed to silver nitrate solution by incubation in silver nitrate solution followed by incubation in a solution of sodium acetate. The silver nitrate in the tissue is converted into silver acetate in situ which precipitates in the tissue matrix. The concentration of silver nitrate and silver acetate solution will very depending on the amount of silver salt is needed in the tissue. In the preferred embodiment, silver ion leaching of 10-100 microgram of silver per cm square of tissue surface is preferred. The deposited silver crystals may also improve radio-opacity of the tissue.

In many applications, tissue prepared according to an embodiment of the present invention may be cut into several geometric shapes. These shapes are then used to construct unique medical devices such as, by way of example, and not limitation, heart valve bioprosthesis, vascular grafts, tissue covered stents, and stent grafts. For example, a bovine pericardial tissue may be cut and sewn to form a heart valve bioprosthesis. In some applications, a perforated tissue may, for example, and without limitation, be used to form a composite material. Also in some applications, the tissue surface may be textured using different shapes, holes, grooves to promote healing or to improve adhesion of biodegradable polymer in the tissue or to deposit controlled drug delivery compositions. In some applications, multiple coating layers of tissue may, for example, and without limitation, be used. For example, a first coating layer may consist of drug and polymer and a second coating layer on top of first layer may consist of only polymer without a drug. Such a coating may act as a diffusion barrier to control the release rate of the drug.

Embodiments of the present invention also include the use of grooves or other geometric shapes created on the tissue surface and their use to fill the biodegradable controlled drug delivery compositions. FIG. 11 illustrates this concept by way of example, in particular FIGS. 8C and 8D. Grooves may be of any shape and pattern. The groove depth and size may depend on the tissue thickness and intended use. Generally groove depth may range from 1 to 2000 micron most preferably from 20 to 1000 micron. Many groove shapes may be used these include but not limited to wedged shape, rectangular shape, cylindrical shape and the like. In a membrane-like tissue such as, by way of example, and not limitation, porcine pericardium or bovine pericardium, 10 micron to 2 mm diameter holes (i.e., cylindrical grooves) are created using any known method in the art such as, by way of example, and not limitation, laser drilling, mechanical drilling and the like. The holes or grooves are then filled with the liquid or solid drug delivery compositions, e.g., controlled release polymer compositions containing bioactive compounds. For example, the holes are filled with bioerodable or biodegradable polymer with bioactive compound such as, by way of example, and not limitation, Lovastatin or Atrovastatin (HMG-CoA inhibitor). The bioactive compound is then released from the polymeric matrix. FIGS. 8E and 8F illustrate, by way of example, and not limitation, the use of perforated tissue. This tissue may be coated with biodegradable polymer with bioactive compound. The membrane tissue used may be biostable (crosslinked) or biodegradable (non-crosslinked).

A composite tissue-biodegradable composite material or coated tissue material according to an embodiment of the present invention can be formulated so that they can be delivered using minimally invasive surgical (MIS) techniques such as, by way of example, and not limitation, laparoscopy, thoroscopy and the like and thus are useful for localized drug delivery inside a living body. One embodiment of the present invention provides for a method for the treatment of a medical condition at a localized site, including the steps providing a implantable membrane like animal tissue including a bioactive compound; compacting the tissue to a size suitable for implantation using minimally invasive technique; transporting the compacted tissue to a localized treatment site; uncompacting the tissue to its original size; and immobilizing the tissue on the treatment site wherein the implantable tissue and a bioactive compound assists in the treatment of the medical condition. In one exemplary approach, the pericardial tissue-polymer composite patch loaded with rifampin is rolled into tube or other compacted shape so that it can be transported to a localized surgical site using a minimally invasive surgical (MIS) technique. The drug delivery patch material is then unrolled to form a flat membrane at the surgical site. The patch is then applied on the tissue surface and conformed to the localized tissue or organ geometry. The patch is secured in place by suturing or stapling to the surrounding tissue. The suture or staple may be biodegradable or biostable. The patch is then used to releases the drug in the localized surgical environment In some embodiments, a composite of fixed tissue such as, by way of example, and not limitation, discussed in this invention or glutaraldehyde fixed tissue is used to incorporate high molecular weight biocompatible biostable polymers such as, by way of example, and not limitation, Teflon® (polytetrafluoroethylene) or polyethylene vinyl acetate copolymers or their derivatives or polysulfones may be incorporated using a solvent technique. In one example, amorphous Teflon® is dissolved in a proprietary halogenated solvent obtained from 3M Corporation. A dehydrated glutaraldehyde fixed bovine pericardial patch tissue is then exposed to the Teflon® solution. The solvent is then evaporated. The Teflon® polymer-fixed tissue composite is used as a biostable composite patch for variety of surgical applications. Alternatively expanded, partially expanded or unexpanded polytetrafluoroethylene (PTFE) membrane may be used to make a tissue based composite patch. The PTFE membrane may be sewn to the using PTFE based sutures. The composite patch may be useful as hernia surgery application.

Use of Tissue Engineered Material for Making Bioprosthesis

This invention also teaches of compositions and methods wherein the tissue used in making bioprosthesis is obtained from non-animal source like cell culturing or tissue engineering technologies. The use of animal tissue in bioprosthesis manufacture is known for quite some time. However, animal tissue use has certain limitations such as size of the maximum single piece that can be derived from the animal. Also chemical/protein composition of the animal skin tissue used in conventional animal cannot be changed and is dependent on the species and type of tissue used. The tissue derived from animal tissue may also contain pathogenic viruses and proteins such as Bovine Spongiform Encephalopathy (BSE). The use of membrane like tissue, made using tissue engineering technologies, overcomes these limitations. In this invention, membrane like tissue that may be useful to make bioprostheses, is derived from modern tissue engineering technologies which are known in the tissue engineering art or yet to be developed. In one exemplary embodiment, a sterile porous scaffold is seeded with smooth muscle cells along with tissue culture medium that supports the growth of such cells. The scaffold, cells and cell culture media are incubated at 37° C. in an atmosphere that supports mammalian cell growth (controlled carbon dioxide, humidity etc). Care is taken to minimize bacterial or fungal contamination of the scaffold or culturing cells. The incubation of cells is continued until cells attach, grow and create their own extracellular matrix tissue. Additional cell seeding, cell culture media exchanges may be done to achieve a desired tissue thickness is reached. The preferred thickness of engineered tissue may range form 1 micron to 3000 micron, most preferably 50 microns to 1500 microns. The preferred size of engineered tissue is >1 square inch, more preferably 1 to 1000 square inch, even preferably 1 to 150 square inch.

The biodegradable scaffold materials that can be used to make the engineered tissue include but not limited to are: degradable polyesters such as polyhydroxy acid, polylactones, polyhydroxyalkanoates which are the polyesters produced by microorganisms such as poly(3-hydroxybutyrate), 3-hydroxyvalerate, 4-hydroxybutarate, 3-hydroxyhexanoate, 3-hydroxyoctanoate. Other degradable polymers include but not limited to are: polyamides, collagen, gelatin, polyanhydrides, polyglycolate, polyglycolic acid, polycaprolactone, polycarbonates such as polytrimethylene carbonate, degradable polyurathanes, fibrinogen, and the like. Copolymers or blends of such materials may also be used. The biodegradable scaffold materials may be the form a fiber such as polyester fiber, collagen fiber, silk fibers, polyamide or nylon fibers which may be woven to produce a suitable scaffold. The scaffold used manufacturing of engineered tissue may be porous or non-porous. Many methods of introducing porosity are known in the art. These methods include but not limited to: leaching of soluble salts from the polymer matrix, lyophilization of hydrogel materials, sublimation of solvents or porosity generating compounds from the polymers and the like. The porosity is chosen to promote rapid cell attachment and growth. The porosity of scaffold may range from 1 microns to 1000 microns, most preferably 10 microns to 500 microns to promote cell infiltration and growth. The scaffold surface may be chemically or physically modified using bioactive compounds or peptides that promote cell attachments. Such compounds include but not limited to peptides such as RGD, RGDS, IGD and the like. The size, shape and geometry of scaffold may vary depending on the intended use. A membrane like scaffold with size ranging from 1 square inch to 1000 square inch may be used for large scale manufacturing of membrane like tissue. The preferred size be may be similar to textiles used cloth manufacturing. A continuous or batch processing methods may be used. The thickness of membrane like scaffold may vary from 1 microns to 3000 microns, more preferably from 1 microns to 2 mm. The scaffold could also be circular, rectangular, triangular, hexagonal or any other 2-dimensional shape. Square or rectangular shape is preferred due to its simplicity in large scale manufacturing. Several membrane like scaffolds may be stacked in a biotechnology tissue engineering reactor and seeded with mammalian cells to generate large quantity of engineered tissues suitable for large scale bioprosthesis manufacturing. The scaffold could also have simple or complex 3 dimensional shapes or geometries. These geometries may include but not limited are: hollow cylindrical tube, cylinder, sphere or complex shapes. Membrane shaped tissue engineered tissue may also be created by using a hollow cylindrical tube like scaffold and then cutting the tube shaped engineered tissue to make a sheet or membrane like tissue.

Chemical compositions of tissue engineered tissue may be changed by choosing appropriate cell line or combination of cells in building a desired engineered tissue. The cells could be obtained from many animals. Cells from mammalian source are most preferred. The cells may be obtained form animals source which include animals but not limited to: human, cow, pig, sheep, deer, ostrich, crocodile, rabbit, rat, snake and the like. Human, pig, sheep or bovine cells are most preferred. Many types of cells could be used to produce a tissue engineered material. The preferred cells chosen which produce large amount of extracellular matrix proteins such as collagen, elastin and keratin and the like. The cell types that can be used but not limited to include: fibroblasts cells, endothelial cells, smooth muscle cells, muscle cells, cells found in heart tissue or pericardial membrane, cells found in human or animal skins, sub-mucosa cells, epidermal cells, epithelial cells, and the like. The cell may be may be purchased from commercial sources such as ATCC along with their cell culture media or may be obtained from animals using surgical biopsy technique, separated and cultured using known tissue culture techniques. For example, if a collagen rich tissue is desired, mammalian cells that produce pericardial type tissue may be used. For skin tissue, cells that generate a combination of collagen and elastin may be used. Stem cells which can be converted into any organ may also be used. Two or more cell types may also be used to create a desired tissue. For example animal cells such as bovine or porcine cells may be used to create a structural part of the tissue and the outer layer may be derived from human cells to give feel, texture and biological properties of a human tissue. Genetically modified cells may also be used to influence the properties of the engineered tissue.

Cell culture medium that is used to grow cells may include several chemical substances that support the growth of mammalian cells. Cell culture medium may be obtained from commercial sources such as Sigma-Aldrich. These substances include chemicals that have been developed or yet to be developed but not limited to are: water, pH controlling buffers such as phosphate buffer, HEPES buffer; amino acids; sugars; antibiotics; pH indicator dyes; proteins such as albumin; growth factors such as fibroblast growth factors; blood products such as serum and the like Cell lines used to grow the tissue will dictate the choice of cell culture medium and incubation period. Cell culture medium that does not have serum components (serum free medium) is most preferred for large scale manufacturing operations. The cell culture medium composition may be used to influence the texture and other properties of the engineered tissue. For example, non-natural aminoacid may be used to influence the chemical composition of the extracellular matrix produced or cells may be genetically modified to produce a given tissue type. The engineered tissue may be decellularized prior to medical device use. This step is particularly useful if non-human derived cells are used to make the engineered tissue.

The tissue generated by tissue engineering methods described above may be decellularized to generate the extracellular matrix suitable for implantation. Many methods of decellularization are known in the art and could be used without limitation. The preferred methods of tissue decellularization are described in the experimental section. Tissue may also be crosslinked or chemically modified to improve tissue properties. Some preferred crosslinking methods are described in this invention. Other conventional crosslinking methods such as glutaraldehyde crosslinking, EDC crosslinking, dye mediated photooxidation, hexamethylene diisocyanate crosslinking, crosslinking and the like may also be used. The tissue generated by tissue engineering methods may be rendered biostable or biodegradable my many methods known in the art or methods described in this invention. For example, tissue treated with glutaraldehyde, hexamethylene diisocyanate, photooxidation may render the tissue substantially biostable. In applications where biodegradable tissue is needed, uncrosslinked tissue or crosslinking catalyzed by -ethyl-3-(3-dimethylaminopropyl carbodiimide) hydrochloride (EDC) is most preferred The EDC crosslinking is generally known as "zero length cross-linking" in the protein modification chemistry art. EDC is a class of compounds generally known as carbodiimides. Carbodiimides generally promote reaction between carboxylic acid-amine and carboxylic acid-hydroxyl groups to form amide or ester bond respectively. Water soluble carbodiimides are most preferred crosslinkers. Water soluble carbodimide such as EDC is most preferred. Other carbodiimides that can be used include but not limited to: 1-(3-dimethylaminopropyl)-3-ethylcarbodiimide methiodide; 1-(3-dimethylaminopropyl)-3-ethylcarbodiimide; 1-cyclohexyl-3-(2-morpholinoethyl) carbodiimide metho-p-toluenesulfonate; 1-(3-dimethylaminopropyl)-3-ethylcarbodiimide and the like. EDC can catalyze a reaction in water over a wide pH range. The pH range may vary from 1 to 9. Most preferred pH range is 5 to 7. The desired pH may be achieved by using a biocompatible buffering agents. The preferred buffers that can be used include, but not limited to, phosphate buffered saline (PBS) (pH 7 to 7.5), morpholino ethanesulfonic acid (MES) (pH 5.5 to 6.5) and triethanol amine buffer (pH 7 to 7.5), sodium acetate buffer and the like. A buffer concentration in the range of 10 mM to 100 mM is preferred. Among the buffers, PBS or MES buffers are most preferred. A co-catalyst that may accelerate the crosslinking reaction is added. Examples of such co-catalyst include, but not limited to, n-hydroxysuccinimide or n-hydroxysulfosuccinimide. The molar concentration of co-catalyst is in the same range as that of EDC. The cross-linking reaction is generally completed with in 1 to 600 minutes, more preferably between 1 to 30 minutes. The preferred reaction temperature is below the shrink temperature of tissue, typically 0 to 45° C. Crosslinking reaction at 4 to 37° C. temperature range is even more preferred.

The crosslinked tissue is then used to manufacture bioprostheses such as heart valve, stent grafts, vascular grafts, hernia surgical repair, rotating cuff repair and the like. If desired, smaller engineered tissue sizes may be stitched together to make a larger size tissue or thinner tissue may be combined or stacked and glued to make a thicker tissue for a particular medical device application. The engineered tissue may be crosslinked using several methods known in the bioprosthesis processing art or methods yet to be developed. If desired, smaller engineered tissue sizes may be stitched together to make a larger size tissue or thinner tissue may be combined or stacked and glued to make a thicker tissue for a particular medical device application. The engineered tissue may be crosslinked using several methods known in the bioprosthesis processing art or methods yet to be developed Medical Applications of Tissue Materials Tissue prepared according to an embodiment of the present invention may, for example, and without limitation, be used for variety of medical and surgical applications, e.g., implantable tissue or for manufacture of bioprosthesis as defined earlier. These applications include, but are not limited to, applications which are already known such as, by way of example, and not limitation, vascular patch, heart valve, venous valve bioprosthesis, vascular grafts, surgical patch, or applications which are yet to be developed. Complex medical devices such as, by way of example, and not limitation, heart valve, stent grafts and sewing cuffs are also included. Many variations of valve designs may, for example, and without limitation, be used. The tissue used may be subjected to additional anticalcification treatments such as, by way of example, and not limitation, treatment with ethanol solutions (>50% buffered ethanol solution) or surfactants or chemical modifications with long alkyl chains. Medical devices such as, by way of example, and not limitation, coronary stents or peripheral stents may be partially or fully covered with the tissue such as, by way of example, and not limitation, bovine pericardial or porcine pericardial tissue or porcine sub-mucosa tissue and used. In one embodiment, the present invention provides for a method for making a tissue/stent graft including the steps of providing an expandable metal or polymeric stent capable of supporting mammalian cell growth on its surface; exposing the stent to a mammalian cell culture medium including live mammalian cells capable of attaching and growing on the stent; growing the cells on the stent surface until the stent surface is partially or completely covered by the cells and extra cellular matrix; and exposing the stent to a tissue fixative solution. Coated tissue may also be used make stent grafts used in the vascular surgery. The present invention also encompasses an expandable stent wherein the stent is fully or partially wrapped or covered with a non-cytotoxic membrane-like tissue. Bovine ureter, bovine thoracic artery or other arterial tissue may, for example, and without limitation, be used as small or medium bore vascular grafts. The tissue used may be loaded with biological active compounds by methods known in the art or methods described herein. Hybrid devices such as, by way of example, and not limitation, graft tissue coated with polymeric elastomers may, for example, and without limitation, be used to make improved vascular grafts. In one embodiment, a polymeric vascular graft made from polyurethane elastomer may be completely wrapped in a membrane like tissue. Such wrapping provides animal tissue as blood contacting surface for the graft. The polyurethane provides a self sealing property to the graft. In another embodiment, crosslinked bovine thoracic artery is dehydrated using a series of alcohol solutions and finally using dimethyl acetamide (DMAC) as a solvent. A 10% solution of Biomer® polyurethane in DMAC is sprayed on the outer surface of the graft. The solvent is removed by air drying and finally by vacuum drying. The polyurethane-tissue composite graft may offer improved mechanical properties.

The animal tissue, especially a membrane-like tissue such as, by way of example, and not limitation, porcine pericardial tissue, bovine pericardial tissue or porcine intestinal tissue may, for example, and without limitation, be used in wound management applications. The wound management applications include, but are not limited to, venous ulcers, drainage wounds, diabetic ulcers, chronic vascular ulcers, pressure ulcers, trauma wounds, surgical wounds, burn wounds, partial and full thickness wounds and the like. Membrane-type tissue coated with biodegradable polymer capable of releasing bioactive substances is preferred. The preferred bioactive substances for wound management include, but are not limited to, growth factors derived from blood such as, by way of example, and not limitation, PGDF, anti-infective compounds like rifampin, and chlorhexidene acetate.

The tissue-based patch may also be used in various surgical applications. Depending on the application, a biostable or biodegradable tissue may, for example, and without limitation, be used. In one embodiment, the present invention provides for a method sealing a leaking tissue during a surgical procedure including the steps of providing a membrane like animal tissue suitable for human implantation; providing a surgical adhesive capable of adhering with the tissue; and curing a surgical adhesive between a leaking site and membrane like tissue. The applications include, but are not limited to providing pubourethral support for the treatment of urinary incontinence; abdominal wall repair; vascular surgery applications like intracardiac defect repair, septal defect repair, great vessel repair and anulus repair; suture-line buttressing; hernia repair; perforated tissue repair; general tissue repair such as, by way of example, and not limitation, prolapsed tissue repair, thoracic wall repair, carotid patch, pelvic floor repair, bladder repair; dural substitute for closure of dura during neurosurgery;

Membrane-like tissue (biostable or biodegradable) such as, by way of example, and not limitation, bovine pericardium, porcine pericardium, porcine submucosa may be cut into strips, strands or fibers. Many known methods to cut the tissue into small fiber-like strands may, for example, and without limitation, be used. The methods reported in the prior art may, for example, and without limitation, be used. These methods include, but are not limited to, methods such as, by way of example, and not limitation, mechanical shredders, ultraviolet, visible and infrared laser cutting-based methods, water jet cutting methods, ultrasonic wave-based cutting methods and the like. The shredded tissue or fiber may be braided or woven to generate cloth like structures or rope like structures. These braided or woven structures may, for example, and without limitation, be used to fabricate many devices such as, by way of example, and not limitation, vascular patch, vascular grafts, stent grafts etc. Synthetic fibers such as, by way of example, and not limitation, polyester fiber, Teflon® fiber, polyethylene fiber, poly propylene fiber, silk fiber, poly(hydroxy acid) or polylactide or carbon fiber may be braided or woven along with braided tissue to form composite structures. Such composite may provide additional properties to the woven or braided structures. Such braided structures may, for example, and without limitation, be used as substitutes for ligaments. The synthetic fibers used may be biodegradable.

Tubular tissue such as, by way of example, and not limitation, arterial tissues may, for example, and without limitation, be used to make catheters. For example, catheters that require a longer implantation time may be made using crosslinked animal tissue. The outer layer of nerve tissue may, for example, and without limitation, be used to make nerve guide repair devices.

Transparent tissues such as, by way of example, and not limitation, porcine cornea may, for example, and without limitation, be used to obtain a transparent material If unsaturated monomers are used in such tissue fixation, then monomers which give transparent hydrogel may, for example, and without limitation, be used. For example, tissue may be fixed with 2-hydroxyethyl methacrylate, vinyl pyrrolidinone monomers which give optically transparent hydrogels. In general, monomers which are used in commercial contact lens manufacturing are preferred. Such transparent materials may, for example, and without limitation, be used in various ophthalmic applications such as, by way of example, and not limitation, corneal transplants, implantable contact lens or intraocular lens, etc. Tissue fixed with a degradable crosslinkers may, for example, and without limitation, be used as a scaffold for tissue engineering.

In many medical applications, implantable tissue may be subjected to additional crosslinking or anticalcification treatments which are known in the art. Such alternations, combinations or modifications are encompassed by the present invention even if specific examples or embodiments are not provided in this manuscript.

The membrane-like tissue is especially useful as a barrier for prevention of postoperative adhesions. Membrane tissue coated with non-cell adhesive hydrogels or polymars such as, by way of example, and not limitation, polyethylene glycol based hydrogel or PTFE based membranes is especially useful. A localized release of cell cycle inhibitor such as, by way of example, and not limitation, Rapamycin, paclitaxel, Actinomycin, Lovastatin through coated or composite tissue may also assist in reducing postoperative adhesions.

Hernia repair is among the most common general surgery procedures. Complications cited in the medical literature include intestinal fistulas and surgical adhesions, which may cause intestinal obstruction. The coated tissue compositions or tissue-PTFE composite membrane like materials described in this invention are especially useful for hernia repair applications. A membrane like tissue (biodegradable or biostable) described in this invention or commercially available tissue patch such as AlloDerm® marketed by LifeCell Corporation is coated with polyethylene glycol coating on one side is especially useful for Hernia repair application. The PEG coating acts as a non-cell adhesive layer which reduces postoperative adhesions. The other non-coated side promotes cell adhesion and integrates into the native tissue. The PEG based coating operation may be carried out prior to implantation. For example, AlloDerm® patch may be coated with DuraSeal™ sealant from Confluent Surgical Inc., Waltham, Mass. just prior to implantation and may be used for hernia repair applications. The PEG coating may be replaced by non-cell adhesive membrane like PTFE membrane such as Gore-Tex surgical patch which is also known to reduce postoperative adhesions. The ePTFE membrane-tissue or AlloDerm® composite may be prepared by suturing the two membranes using ePTFE based sutures.

Membrane-like tissue such as, by way of example, and not limitation, bovine pericardium or porcine pericardium may, for example, and without limitation, be used as structural backing material for tissue adhesives. Many types of surgical adhesives could be used including those that are commercially available or yet to be developed. In one approach, structural adhesive material or their precursors may be coated on one side of pericardial tissue. The tissue provides the mechanical support for the adhesive material. Upon application, adhesive materials develop strong adhesive bond between surgical site and tissue backing material used. The surgical adhesive and pericardial tissue could be biodegradable or biostable. In one exemplary approach, a 2 cm by 5 cm non-crosslinked pericardial tissue or sub-mucosa tissue is coated with a liquid surgical adhesive such as, by way of example, and not limitation, a photopolymerizable liquid diacrylate along with a visible light photoinitiator (see Example 35 described below) and cured between a lung tissue and pericardial tissue to seal air leaks. In another approach, cynaocaylic acid ester is used as a adhesive. Many cynoacrylate adhesives could be used these include ester already known in the art or ester yet to be develop for medical device applications. The preferred cynoacrylate esters include but not limited to: methyl, ethyl, butyl or octyl ester and is cured between a lung tissue and uncrosslinked pericardial tissue. Butyl cynoacrylate may also be substituted with FocalSeal® surgical adhesive available from Genzyme Biosurgery. Because uncrosslinked pericardial tissue and polybutyl cynoacrylate are degradable, the patch and adhesive combination serves as a degradable adhesive patch system. In another exemplary approach, polyethylene glycol n-hydroxysuccinimide based crosslinker (PEGNHS) and amine based crosslinking agent are mixed and coated on the tissue in dry state. Upon hydration, the PEHNHS and amine crosslinker react to form a crosslinked polymer and form a strong adhesive bond. Other surgical adhesives or glues such as, by way of example, and not limitation, albumin glue may also be used to make an adhesive patch.

Porcine/bovine meniscus tissue modified according to an embodiment of the present invention may also be used in meniscus repair procedures.

Catheters or catheters parts may be made from implantable animal tissue. Catheters designed to stay with in the body for 3 days or more may be made using compositions according to an embodiment of the present invention.

Membrane-like tissue (biodegradable or biostable) may, for example, and without limitation, be used to fabricate medical devices such as, by way of example, and not limitation, tissue coated stents or stent-grafts. The tissue covering on the stent may be done from outside, inside or form both sides. The stent may be a vascular stent such as, by way of example, and not limitation, coronary stent or peripheral stent or non-vascular stent. Stent used may be biodegradable (made form biodegradable polymers such as, by way of example, and not limitation, cyclic polylactones and their copolymers) or biostable such as, by way of example, and not limitation, metallic stent (made from stainless steel or Nitinol). The tissue used on the stent may be loaded with drugs such as, by way of example, and not limitation, cell cycle inhibitors which are known to inhibit restenosis.

In minimally invasive surgical applications thin but strong membrane tissue is desired. Membrane-like tissue such as, by way of example, and not limitation, bovine pericardium may be too thick in MIS surgical applications. In stent graft application, a strong membrane-like tissue which is about 10 to about 1000 micron thick is highly desirable. Such thin tissue reduces the profile for a stent graft delivery system therefore permits its use in making small diameter (low profile) devices. The thickness of the tissue can be reduced by many methods known in the art such as, by way of example, and not limitation, cutting, polishing and the like. The most preferred method for controlling the thickness is laser-based ablation technique used in vision correction surgery such as, by way of example, and not limitation, photorefractive keratectomy or IntraLase® surgical technique. Laser-based reshaping of tissue is routinely used in Lasik surgery, short for laser-assisted-in-situ keratomileusis, normally used in vision correction surgery. The membrane-type tissue such as, by way of example, and not limitation, porcine submucosa or porcine pericardium or bovine pericardium tissue can be treated using Lasik-like surgery to reduce the desired tissue thickness. Lasik-like technique may, for example, and without limitation, be used to reduce the tissue thickness to about 5 to about 500 microns, most preferably about 50 to about 500 micron thick tissue without significantly compromising other properties of the tissue.

The coated tissue described in this invention may be useful to form strip-like structures that can be used in bone repair. For example, biodegradable tissue like porcine or bovine pericardium may be loaded with bone growth factors such as, by way of example, and not limitation, BMP-2 or BMP-7. The BMP loaded tissue may, for example, and without limitation, be used to heal bone surface defects. Multiple layers of such structures may, for example, and without limitation, be used in bone fracture repair. The membrane-like porcine pericardium tissue may be coated with dematerialized bone matrix. The membrane tissue provides structural strength while demineralized bone matrix provides growth factors and matrix that promotes bone growth. Such composite materials may, for example, and without limitation, be used as a "bonewrap" in bone fracture repair. In another approach, the pericardial tissue may be coated with demineralized bone matrix particles and the composite may, for example, and without limitation, be used as a bone wrap.

Tissue hydroxyapatite composite matrix may be used in bone repair applications. The hydroxyapatite or other bone promoting calcium salts is added to the tissue matrix using many methods known in the orthopaedic biomaterials art. In one exemplary embodiment, hydroxy apatite is synthesized inside the tissue matrix by combining calcium ion and phosphate ion solution in presence of tissue. The calcium nitrate [$Ca(NO_3)_2$, $4H_2O$, Aldrich], may be used as calcium source and ammonium hydrogen phosphate [$(NH_3)_2HPO_4$, Aldrich] may be used as phosphorus source. In presence of tissue, the calcium nitrate solution is added to ammonium hydrogen phosphate solution at 40° C. while maintaining the pH using ammonium hydroxide to 10 and 10.6 to form hydroxyapatite crystals. The reaction mixture is stirred for 24 hours to stabilize the crystals. The ratio of The Ca ion and P ion precursors is maintained 1.6 to make hydroxyapatite crystals. This reaction is carried in presence of tissue such as pericardial tissue so that hydroxyapatite is generated in side the tissue. It is contemplated that the tissue-hydroxyapatite can potentially be used as a matrix for bone formation. If needed bone promoting bioactive compounds such as bone morphogenic proteins (BMP) may be added in the composite matrix to accelerate the bone formation.

In a biodegradable drug delivery patch application, membranes like tissue such as, by way of example, and not limitation, porcine pericardial tissue, bovine pericardial tissue or porcine sub-mucosa, porcine bladder tissue are preferred. The animal tissue used in the patch application may be crosslinked or non-crosslinked. A non-crosslinked tissue is used if an absorbable patch material desired. Drug delivery patch could be formulated to incorporate bioactive compounds. The patch will deliver a therapeutically effective amount of bioactive substance in a controlled manner. The patch may be coated with biodegradable hydrogels encapsulated with cells or bioactive growth factors.

In one potential application, an animal tissue-based patch is used to induce angiogenesis in the heart. Briefly, an animal tissue-based patch is formulated to deliver vascular endothelial growth factor (VEGF) in a controlled manner. The patch is then transported to a surgical site in the body such as, by way of example, and not limitation, the surface of a beating heart and immobilized on the heart surface. The localized release of VGEF induces angiogenesis in the heart. In another application, a patch is formulated to release cell cycle inhibitor such as, by way of example, and not limitation, Rapamycin, Paclitaxel, Actinomycin, Lovastatin, and the like. The patch is then transported to the site where vascular stent or graft is implanted to a site that is susceptible for restenosis. The patch is wrapped around the vessel where restenosis is likely to occur and cell cycle inhibitor is released locally. The local release of cell cycle inhibitor reduces or eliminates restenosis. In some applications, a patch may be coated with hydrogel coatings containing living species such as, by way of example, and not limitation, mammalian cells, stem cells, and endothelial cells. After implantation, the cells may perform a therapeutic function. Cell encapsulation methods such as, by way of example, and not limitation, those described in U.S. Pat. No. 5,529,914, which cited here for reference only as one suitable technique, may be preferentially used in cell encapsulation.

Some of the tissue modifications or crosslinking methods may be performed on autologous tissue obtained during a surgical procedure. Chemicals and instrumentation, and tools required for such procedures may be provided as a kit in the operating room. Autologous or single tissue may, for example, and without limitation, be used as a carrier for biologically active compounds. The drug-tissue based combination may be prepared in the operating room during a surgical procedure. A kit including biodegradable polymer such as, by way of example, and not limitation, polylactic acid/polyglycolic acid copolymer, a non-toxic biocompatible preferably water soluble solvent capable of dissolving biodegradable polymer is provided according to an embodiment of the present invention. The preferred solvents that can be used include, but are not limited to, n-methylpyrrolidinone, dimethyl sulfoxide, acetone, polyethylene glycol, and the like. The biodegradable polymers include, but are not limited to, polymers, copolymers or oligomers of glycolide, dl-lactide, d-lactide, l-lactide, caprolactone, dioxanone and trimethylene carbonate; polyhydroxyacids, polylactic acid, polyglycolic acid, polyanhydrides, polylactones, polyhydroxyalkanoates which are polyesters produced by microorganisms such as poly(3-hydroxybutyrate), 3-hydroxyvalerate, 4-hydroxybutarate, 3-hydroxyhexanoate, 3-hydroxyoctanoate. Preferred hydrophilic polymers include, but are not limited to, polyethylene glycol-polyhydroxy acid or polyethylene glycol-polylactone copolymers (PEG-PL copolymers), polyvinyl alcohol co-polylactone copolymers, and derivatives of cellulose, hyaluronic acid and dextran. The PEG-PL copolymers are most preferred. PEG-PL copolymers such polyethylene glycol-polylactate copolymers can have a range of properties from hydrophobic to hydrophilic depending on the amount of PEG incorporation in the copolymer and molecular weight of PEG and polylactone. The biodegradable polymer solution may be made in the operating room from the sterile components. The biologically active compound is dissolved, suspended or dispersed in the polymer solution. An autologous tissue piece is cut using a surgical incision and then incubated in the polymer solution. The tissue is then removed from the solution and washed with saline and implanted. The polymeric coating holds and releases the bioactive compounds in a controlled manner. For example, rifampin, an antibiotic may be released locally to control infection. The autologous tissue serves as a matrix that can be sutured to immobilize it at a localized disease site. The low toxicity of solvents and biodegradable nature of polymer used in this system provide a simple method for preparing a tissue-based controlled drug delivery device.

The present invention also provides for a method for localized cell therapy including the steps of providing or obtaining a sterile tissue suitable for human implantation; providing a sterile crosslinkable polymer; providing a sterile aqueous based solvent for the crosslinkable polymer; providing or obtaining mammalian cells for therapeutic use; dissolving the polymer in the solvent and dispersing cells in the polymer solution; forming a coating of polymer on the tissue and crosslinking the polymer without damaging the cells; and implanting the tissue.

It is contemplated that the shape memory capable tissue may be used to make many novel medical devices. For example, tissue based vascular grafts may be compressed and the compressed shape may be preserved to improve kink resistance of the graft. The compressed graft become longitudinally compliant as a result of compression and may have better patency rates. A heart valve leaflet shape may be preserved to reduce stresses during heart valve device use. A tissue based breast implant with appropriate shape may be preserved using methods described in this invention.

The selective modification of tissue to create biodegradable and biostable regions may be used to create new medical devices.

In many medical device applications, bioprostheses prepared may be sterilized by many methods known in the art. These methods include but not limited are: gamma radiation sterilization, ethylene oxide or propylene oxide based sterilization methods, electron beam sterilization, iodine-based sterilization methods, and the like. The preferred method is ethylene oxide gas sterilization or gamma radiation sterilization. The sterilization process parameters will depend on the tissue based medical device to be sterilized.

In some applications proteins such as, by way of example, and not limitation, collagen or albumin are treated with silver salt solution to form silver salts/complexes of amino acids present in the proteins. For example, aspartic acid which produces free carboxyl acid groups in the proteins may be treated with silver to form a silver salt. The resultant silver salt then releases silver ions upon implantation producing an antimicrobial effect due to silver ions.

The tissue-based medical devices described herein may be packaged using variety of packaging methods including packaging in a liquid solution such as, by way of example, and not limitation, glutaraldehyde solution. In preferred packing method, the tissue is packaged in sealed plastic bag. If desired, the tissue may be packaged and stored under inert gas atmosphere such as, by way of example, and not limitation, nitrogen, carbon dioxide or argon gas. The gas used may be kept under pressure.

The following non-limiting examples are intended to illustrate the inventive concepts disclosed in this document. Those skilled in the art will appreciate that, in light of the teachings of the present invention, modifications can be made to these examples, drawings, illustrations and claims which are contemplated to fall within the scope the present invention.

Materials and Methods

Tissue-like bovine pericardium, porcine pericardium, porcine sub-mucosa, porcine aortic root, porcine meniscus tissue and bovine thoracic arterial tissue are acquired from local abbotair or slaughter house. The animals from abbotair or the tissue obtained form abbotair may be screened or tested for infectious viruses, bacteria or proteins such as, by way of example, and not limitation, BSE which cause disease such as, by way of example, and not limitation, Bovine Spongiform Encephalopathy. Tissue infected with harmful virus or proteins may be discarded. Preferably, the tissues are collected from slaughter house with in 30 minutes after the kill. Within 36 hours, the tissue collected is cleaned to remove excess fat, connective tissue, blood and other cellular components and rinsed with cold phosphate buffered saline and stored in hyperosmotic storage solution (ESWHS solution) until fixation or other modifications. In many instances, the tissue may be treated with detergents, organic solvents such as, by way of example, and not limitation, aqueous ethanol or long chain alcohols such as, by way of example, and not limitation, octanol or 1,2-octane diol other tissue cleaning solutions that remove cells/cell debris from the tissue and leaves behind only extracellular matrix. The acellular extracellular matrix is preferred in many medical device applications. Acrylic acid n-hydroxysuccinimide ester, acetic acid n-hydroxysuccinimide, polyethylene glycol n-hydroxysuccinimide esters, acrolein are purchased from Sigma-Aldrich or Pierce or Sherewater. Polyethylene glycol can be purchased form various sources such as, by way of example, and not limitation, Nektar Therapeutics (formerly Shearwater Polymers), Dow Chemicals (Union Carbide), Fluka and Polysciences. Multifunctional hydroxyl and amine terminated polyethylene glycol are purchased from Nektar Therapeutics, Dow Chemicals and Texaco. Amine-terminated polyethylene glycols also can be synthesized using methods known in the prior art. Other specialized polyethylene glycol derivatives may also be purchased or custom synthesized from Nektar Therapeutics. DL-lactide, glycolide, caprolactone and trimethylene carbonate can be obtained from commercial sources like Purac, DuPont, Polysciences, Aldrich, Fluka, Medisorb, Wako and Boehringer Ingelheim. N-hydroxysulfosuccinimide can be purchased from Pierce. All other reagents, solvents are of reagent grade and can be purchased from commercial sources such as, by way of example, and not limitation, Polysciences, Fluka, ICN, Aldrich and Sigma. Most of the reagents/solvents are purified/dried using standard laboratory procedures such as, by way of example, and not limitation, described by Perrin et al. Monomers may be purified to remove inhibitors just prior to use. For example, liquid monomers such as, by way of example, and not limitation, 2-hydroxyethyl methacrylate may be vacuum-distilled to remove the inhibitor. Most commercially available monomers are purchased from Polysciences, Fluka, ICN, Aldrich and Sigma. Photoinitiator 2-Hydroxy-1-[4-(2-hydroxyethoxy)phenyl]-2-methyl-1-propanone (Irgacure 2959) and 2,2-dimethoxy-2-phenylacetophenon(Irgacure 651) are purchased from Ciba Specialty Chemicals or Sigma-Aldrich. Small laboratory equipment and medical supplies can be purchased from Fisher or Cole-Parmer. Cell culture experiments are performed using a standard mammalian tissue culture laboratory or microbiology laboratory capable of handling and growing mammalian and human cell cultures.

Removal of Cellular Components from the Tissue (Tissue Decellularization)

Tissue suitable for implantation may be treated to remove cells and cellular components or fragments, DNA fragments and the like. The removal of cellular components is believed to reduce immunogenicity of the implanted tissue. Upon removal of cellular components, only extracellular matrix components such as, by way of example, and not limitation, collagen, elastin, laminin, keratin, glycosaminoglycans are retained in the tissue. The extracellular matrix is believed to be non-immunogenic. Many protocols for removal of cellular components are reported in the prior art, one of the preferred protocols is provided below. Ten 1 cm by 1 cm bovine pericardium pieces, cut from a freshly obtained bovine pericardial sac, are transferred to 50 ml conical flask containing 10 ml phosphate buffered saline (PBS, pH 7.2). The tissue is then incubated in 100 ml distilled water at 4° C. for 48 h, followed by incubation in 30% sodium chloride and/or saturated sodium chloride solution for 48 hours followed by washing with 100 ml PBS solution three times. The tissue is then treated with 40 ml of 0.25% trypsin-EDTA, for 30 minutes at 37° C.; followed by washing with warm (37° C.) 100 ml PBS solution three times. It is then treated with 40 ml of micrococcal nuclease, 1 unit/ml, for 20 minutes at 37° C.; followed by washing with warm (37° C.) 100 ml PBS solution three times. It is then further treated with 40 ml of Triton X-100, 10%, for 10 minutes at 37° C.; followed by washing with warm (37° C.) 100 ml PBS solution three times. It is then treated with 40 ml of 0.1 M sodium hydroxide at 37° C. for 30 minutes; followed by washing with warm (37° C.) 100 ml distilled water five times. It is then treated with 40 ml of 0.1M hydrochloric acid at 37° C. for 30 minutes; followed by washing with warm (37° C.) 100 ml distilled water five times. Finally the tissue is washed with 70% isopropanol three times and stored in 70% isopropanol at −20° C. until further use.

In a simplified cell removal protocol (tissue decellularization protocol)), tissue is first treated with a 0.25% trypsin-EDTA solution in PBS for 30 minutes at 37° C. followed by a treatment with 10% surfactant solution (Triton X-100) for 2 hours to remove cellular debris or soluble proteins.

Shrink Temperature by Differential Scanning Calorimetry

Shrink temperature is evaluated by differential scanning calorimetry. Briefly, 3-10 mg of tissue sample is heated in a sealed aluminum sample pan and heated at 10° C. per minute up to 200° C. under nitrogen atmosphere. The endotherm around 55° C. to 110° C. is attributed as shrink temperature.

Shrink Temperature by Visual Method

A 3 cm×1 cm tissue strip is cut and the rectangular shape of the tissue is traced on a paper to record its size. In a 500 ml beaker, 300 ml saline solution is transferred. The tissue is then suspended in the saline solution using a cotton or metal thread and is completely immersed in the saline solution. The solution is slowly heated on a hot plate until boiling. The tissue is visually observed until signs for shrinkage. The temperature at which tissue significantly shrinks is recorded. The tissue is removed from the solution, washed with water. The size of the tissue again traced on a paper and compared with the original size. The shrunken tissue shows significant reduction in size (typically >20% shrinkage). Untreated tissue and treated tissue are usually compared in the same experiment.

Viability and Spreading of Bovine Endothelial Cells on Crosslinked Bovine Pericardial Tissue Tissue samples fixed using crosslinking agents such as, by way of example, and not limitation, photopolymerization, are used in this experiment. Untreated bovine pericardium tissue is used as control. 1 cm×1 cm size tissue samples are soaked in 70% ethanol (overnight), washed with sterile PBS (15 minutes, 3 times) and soaked in Minimum Essential Medium (MEM) supplemented with aminoacids, antibiotics and 30% fetal bovine serum (FBS) for 1.5 h. The tissue samples are then transferred to a 24 well sterile tissue culture plate. Bovine aortic endothelial cells passaged in MEM/10% FBS are resuspended in MEM/10% FBS and approximately 200000 cells are carefully placed on the tissue samples. The cells are allowed to adhere for 30 minutes before adding 0.75 ml of the same medium to each sample. After 24 hours of incubation in a 5% carbon dioxide atmosphere at 98% humidity and 37° C., the samples are transferred to new wells and fresh medium is added to these wells. The samples are incubated for a further period of 24 to 72 hours. At the end of this incubation period, the tissue samples/cells are washed with PBS (3 times, 5 minutes per dish at room temperature) and fixed using 4% formaldehyde for 10 minutes. After rinsing the samples in PBS as described above, they are treated with 0.1% Triton X100 in PBS for 3 minutes. The cells are then stained with phalloidin/rhodamine (diluted 1:40 in PBS) in dark for 45 minutes, rinsed 3 times in PBS and viewed immediately under a fluorescence microscope. The morphology and coverage of endothelial cells on tissue samples are recorded. Some representative snapshots are photographed for each sample. Glutaraldehyde-treated tissue is used a negative control and untreated tissue is a positive control. The untreated and photopolymerization treated tissue (vinyl pyrrolidinone treated) showed substantially higher cell growth and attachment as compared to glutaraldehyde fixed tissue. It is generally known that glutaraldehyde fixed tissue does not support tissue growth.

Subcutaneous Implantation of Tissues 1 cm2 rectangular tissue pieces are implanted using a standard surgical protocol. Prior to implantation, the tissues are rinsed for 3 minutes in each of three basins containing 500 ml of sterile PBS, accompanied by gentle shaking. Specimens are implanted subcutaneously 1 cm lateral from the abdominal midline in 3 week old Sprague-Dawley rats and retrieved after 60 days. Unimplanted samples (two per crosslinking treatment) are used as unimplanted control. Untreated tissue is used as positive control. Glutaraldehyde-fixed tissue is used as a negative control. Tissue modified with unsaturated group and infused with monomer and photoinitiator but not exposed to light is treated as dark control.

X-Ray Imaging and Histology

The subcutaneously implanted samples are recovered after 30, 60 or 90 days. The explanted samples are subjected to standard medical x-ray imaging for calcification/mineralization as a result of implantation. The unimplanted samples and samples fixed with glutaraldehyde are also imaged and used as controls. The calcified deposits can be seen in samples treated with glutaraldehyde. An untreated unimplanted sample does not show calcific deposits when viewed using medical x-ray imaging technique or when stained using Van Kossa stain. After visual analysis, the parts of the samples are sectioned, stained with H&E, Masson's trichromeand and Van Kossa stain and then evaluated histologically for inflammation, vascularization, calcification and collagen organization. Inflammation consists of aggregates of lymphocytes and plasma cells, and the presence of mast cells in the implants and is graded from 0=None, to 5=Severe (most of the section with large lymphoid aggregates). Calcification is also graded from 0 to 5 based on Van Kossa stain.

Calcium Assay

The calcium content of the subcutaneously implanted samples is determined by the wet-washing technique. Briefly, up to 0.5 g of explanted tissues are dried and weighed and by heated up to 250° C. with 4 ml of concentrated sulfuric acid followed by heating up to 300° C. with addition of concentrated nitric acid. The resulting digested sample is brought to 40 ml with addition of high purity water. Calcium concentration in the solution is determined by standard ICP methodology.

Pepsin Digestion Assay-Analysis of Tissue Fragments by Gel Electrophoresis

Pepsin digestion is done to evaluate the ability of tissue to resist enzymatic degradation. Briefly, the fixed and control tissue samples are exposed to a pepsin solution and size and weight of the tissue is monitored. Untreated and uncrosslinked tissue sample is used as a control. In another method, tissue samples are clipped into small fragments and digested for 4 h at 37° C. in 10 mM HCl solution containing 4 mg/ml pepsin. Sham digestions are also prepared in HCl without the enzyme. Following the incubation, the samples are centrifuged at 4° C. for 1 hour at 14,000 rpm. The supernatants are analyzed by gel electrophoresis using 10-20% acrylamide:bisacrylamide (37.5:1) gradient gel. Control samples with the same quantity of enzyme are also treated as above, but in the absence of tissue. The fixed tissue shows significantly lower proteins on gel as compared to unfixed tissue. The fixed tissue also shows lower weight loss when compared to unfixed tissue indicating stability of the tissue.

Pepsin Digestion Assay-Gravimetric Analysis

The tissue to be treated is washed with distilled water and incubated in distilled water for 10 minutes. The same is then dried in air and then kept in vacuum oven for drying until constant weight is observed. The dried tissue is then incubated in 10 mM HCl containing 40 mg of pepsin for 12 hours. The tissue is removed, washed with distilled water and again dried till constant weight. The difference in the tissue weights before and after the test is noted. The loss in weight shows the amount of protein digested by pepsin. The unfixed or uncrosslinked tissue generally shows substantial loss as compared to fixed or crosslinked tissue.

Collagenase Digestion Assay

The resistance to enzymatic digestion also can be found by exposing the tissue to collagenase solution. Briefly, a tissue is exposed to a 0.01 mg/ml collagenase enzyme solution in 10 mM TES buffer (N-tris[hydroxymethyl]methyl-2 aminoethane sulfonic acid) and 25 mM calcium chloride solution at 37° C. for 24 to 96 hours and the weight loss of the tissue is monitored and compared with the control untreated tissue.

Free Amine Content of Tissue

The free amine content of the treated tissue is determined by the ninhydrin assay. Briefly, tissue is exposed to ninhydrin solution and the absorbance of ninhydrin solution is measured at 570 nm and is compared with control tissue (untreated uncrosslinked tissue). The absorbance is normalized by dividing by weight of tissue before comparison.

Biodegradation and Biocompatibility of Tissue and Tissue-Biodegradable Polymer Composites In vitro degradation of the polymers is followed gravimetrically at 37° C., in aqueous buffered medium such as, by way of example, and not limitation, phosphate buffered saline (pH 7.2). In vivo biocompatibility and degradation life times are assessed after subcutaneous implantation of tissue samples. The implant is surgically implanted in the animal body. The degradation of the implant over time is monitored gravimetrically or by chemical analysis. The biocompatibility of the implant is assessed by standard histological techniques.

General Analysis

Chemical analysis such as, by way of example, and not limitation, structural determination is done using nuclear magnetic resonance (proton and carbon-13) and infrared spectroscopy. High pressure liquid chromatography or UV-visible spectrophotometry is used to determine drug elution profiles. Gel permeation chromatography is used for molecular weight determination. Thermal characterization such as, by way of example, and not limitation, melting point and glass transition temperature is done by differential scanning calorimetric analysis. The aqueous solution properties such as, by way of example, and not limitation, self assembly, micelle formation, and gel formation are determined by fluorescence spectroscopy, UV-visible spectroscopy and laser light scattering instruments.

Example 1

Modification of Tissue Using Unsaturated Succinimide Ester (Acrylic Acid Succinimide Ester)

Modification of Bovine Pericardium Tissue.

Ten 1 cm by 1 cm bovine pericardium pieces, cut from a freshly obtained bovine pericardial sac, are transferred to 50 ml conical flask containing 10 ml phosphate buffered saline (PBS, pH 7.2). 250 mg acrylic acid succinimide ester (ANHS) (Sigma-Aldrich Product Number: A8060) dissolved in 0.5 ml dimethyl sulfoxide is added to the conical flask and the solution is vortexed for 15 minutes. 0.1 g of ANHS in 0.1 ml DMSO is added to the fixation solution every 2 hours up to six hours. The modification reaction is carried for 6 hours at ambient temperature (25° C.) and then for 12 hours at 4° C. with gentle shaking. The reaction is terminated by washing the tissue with 20 ml PBS 3 times. Finally, the tissue is stored in 30 ml 38% isopropanol and 2% benzyl alcohol solution at 4° C. until further use.

In another variation of this method, porcine pericardial sac is obtained from a local abbotair and is cleaned to remove blood and fatty tissue contaminants from the tissue surface. Ten 1 cm by 1 cm pieces are cut from the cleaned pericardial sac and transferred to 10 ml 0.20 M 2-(N-morpholino)ethanesulfonic acid (MES) buffered solution (pH 6.5). 0.5 g acrylic acid n-hydroxy succinimide ester (ANHS) is added to the buffered solution and the reaction is vortexed for 15 minutes and continued for 6 hours at ambient temperature. An additional 0.1 g ANHS ester is added to the mixture at every 1.5 hours. After the reaction, the tissue is isolated and washed several times with PBS and finally stored in 40% isopropanol solution.

Modification of Arterial and Porcine Heart Valve Tissue.

One 1.5 cm piece of bovine thoracic artery and one third section of porcine aortic root containing one valve cusp and one attachment zone and wall is transferred to 50 ml polypropylene centrifuge tube containing 10 ml PBS. 250 mg of acrylic acid succinimide ester dissolved in 0.5 ml dimethyl sulfoxide is added to the tube and the solution is vortexed for 15 minutes. The modification reaction is carried for 6 hours at ambient temperature (25° C.) and then for 12 hours at 4° C. with gentle shaking. The reaction is terminated by washing the tissue with 20 ml PBS 3 times. Finally, the tissue is stored in 30 ml 40% HEPES buffered isopropanol solution.

Modification of Ligament and Meniscus Tissue.

Using a similar procedure described above 1 cm ligament tissue and 1 cm by 1 cm porcine meniscus tissue is modified by 250 mg of acrylic acid succinimide ester dissolved in 0.5 ml dimethyl sulfoxide.

Modification of Corneal Tissue.

Porcine cornea is obtained from a local abbotair and is washed with PBS (pH 7.2) to remove blood and other biological contaminants. The cornea is placed in 100 ml beaker containing 50 ml PBS solution. To this solution, 0.2 g acrylic acid succinimide ester dissolved in 2.0 ml dimethyl sulfoxide is added. The reaction continued for 12 h at ambient temperature. The tissue is removed, washed several times with PBS and stored until use. The reaction conditions are chosen to maintain the transparency of corneal tissue (minimum change in refractive index).

Example 2

Modification of Tissue Using Glycidyl Methacrylate 10 pieces of 1 cm by 1 cm bovine pericardium tissue are transferred to 100 ml conical flask containing ten ml PBS and a magnetic stir bar. To this solution, 2 ml glycidyl methacrylate, 2 ml triethyl amine and 0.5 g tetrabutylamine hydrobromide are added. The reaction is carried for 16 hours at ambient temperature (25° C.) and then 50° C. for 4 hours with gentle stirring. The solution is cooled and the tissue is isolated from the reaction mixture. The isolated tissue is washed with PBS and 40% ethanol to remove traces of glycidyl methacrylate and other catalysts.

Example 3

Modification Tissue Using Acrolein

Ten 1 cm by 1 cm bovine pericardium pieces are transferred to 50 ml conical flask containing 10 ml PBS and 0.60 ml acrolein. The tissue is incubated for 6 hours at ambient temperature (25° C.). An additional 0.1 g acrolein is added to the mixture at every 1.5 hours up to six hours. Finally, the reaction is continued for 4° C. for 48-120 hours with gentle stirring. The tissue is isolated from the reaction mixture and is washed with PBS and 40% ethanol to remove unreacted acrolein.

Example 4

Modification Tissue Using Methacrylic Anhydride or Methacryloyl Chloride

Treatment in Aqueous Medium

Ten 1 cm by 1 cm bovine pericardium pieces are transferred to 100 ml round bottom flask containing 10 ml 100 mM sodium borate buffer, pH 9.5 and a magnetic stir bar. To this solution, 2 ml methacrylic anhydride and 2 ml triethylamine are added. The reaction is carried out for 6 hours at ambient temperature (25° C.) and then at 0° C. for 72 hours with gentle stirring. The solution is cooled and the tissue is isolated from the reaction mixture. The isolated tissue is washed with PBS and 40% ethanol to remove unreacted methacrylic anhydride.

Treatment in Organic Solvent (Dimethyl Sulfoxide)

Ten 1 cm by 1 cm bovine pericardium pieces are transferred to 100 ml round bottom flask containing 10 ml dimethyl sulfoxide and a magnetic stir bar. To this solution, 0.1 ml triethylamine and 0.02 ml methacrylic anhydride are added. The reaction is carried for 24-48 hours at ambient temperature (30° C.) and then the tissue is isolated from the reaction mixture. The isolated tissue is washed with PBS and 40% ethanol to remove unreacted methacrylic anhydride and stored at 4° C. in refrigerator until further use. In some cases the tissue is used immediately and without ethanol treatment in polymerization and crosslinking step.

Example 5

Crosslinking of Unsaturated Group Modified Tissue Using Free Radical Photopolymerization Two 1 cm by 1 cm pieces of unsaturated group modified bovine pericardium tissue prepared per Examples 1-4 are incubated for 30 minutes each in 20% ethanol, 50% ethanol and 70% ethanol. 50 mg of Irgacure 2959 (free radical photoinitiator) is dissolved in 1 ml n-vinyl pyrrolidinone to prepare a monomer solution. The 70% ethanol incubated tissue is transferred to Irgacure solution and incubated for 4 h at 25° C. and then for 12 h at 0° C. The tissue is removed from solution is placed on a glass plate and exposed to a Black-Ray UV lamp (360 nm light, 10000 mW/cm2 intensity) for 5 minutes for each side. The crosslinked tissue is removed and washed with 10 ml PBS to remove unreacted monomer, initiator fragments and water soluble non-crosslinked polymer. The crosslinked tissue shows higher shrink temperature as compared to uncrosslinked tissue indicating crosslinking of the tissue. Presence of polyvinyl pyrrolidinone in the tissue is conformed by IR spectrophotometer. The crosslinked tissue also showed a different texture as compared to uncrosslinked tissue when touched and felt by a human hand. The crosslinked tissue also shows resistance to pepsin digestion.

In some embodiments, the tissue is infused with monomer without dehydrating using alcohol solutions and the subsequent photopolymerization treatment showed higher shrink temperature indicating crosslinking.

Example 6

Crosslinking of Unsaturated Group Modified Tissue Using Thermally Induced Radical Polymerization Two 1 cm by 1 cm pieces of unsaturated group modified bovine pericardium tissue prepared per Examples 1-4 are incubated for 30 minutes each in 20% ethanol, 50% ethanol and 70% ethanol. 10 mg of azobisisobutyronitrile (thermal free radical photoinitiator) is dissolved in 1 ml vinyl pyrrolidinone. The 70% ethanol incubated tissue is transferred to the vinyl pyrrolidinone solution and incubated for 4 h at 25° C. and then for 12 h at 0° C. The tissue is removed, placed between two glass slides. The tissue is then heated in an oven maintained at 55° C. (below the shrink temperature of uncrosslinked tissue) for 4 hours. The tissue is washed with 20 ml acetone and 20 ml PBS to remove water/acetone soluble unwanted products.

Example 7

Crosslinking of Unsaturated Group Modified Tissue Using Radiation or Electron Beam Induced Polymerization Two 1 cm by 1 cm pieces of unsaturated group modified bovine pericardium tissue prepared per Example 1-4 are incubated for 30 minutes each in 20% ethanol, 50% ethanol, 70% ethanol and finally in n-vinyl pyrrolidinone. The tissue is removed from vinyl pyrrolidinone and exposed to gamma radiation (total dose 3 Mrad). The exposed tissue is washed with PBS and examined for crosslinking. No photoinitiator is used to initiate the polymerization and crosslinking of tissues.

Example 8

Crosslinking of Unsaturated Group Modified Tissue Using Mixture of Hydrophilic and Hydrophobic Monomers Two 1 cm by 1 cm pieces of unsaturated group modified bovine pericardium tissue prepared per example 1 are incubated for 30 minutes each in 20% ethanol, 50% ethanol and 70% ethanol. 50 mg of Irgacure 2959 (free radical photoinitiator) is dissolved in 0.8 ml vinyl pyrrolidinone (hydrophilic monomer) and 0.2 ml octyl methacrylate (hydrophobic monomer). The 70% ethanol incubated tissue is transferred to Irgacure solution and incubated for 4 h at 25° C. and then for 12 h at 0° C. The tissue is removed from solution and then is placed on a glass plate and exposed to Black-Ray UV lamp (360 nm light, 10000 mW/cm2 intensity). The crosslinked tissue is washed with large amount of water and 100 percent ethanol to remove organic and water soluble impurities. The ratio of hydrophilic to hydrophobic monomer may be changed to control the water content of the crosslinked tissue. Many monomers known in the free radical polymerization chemistry art that provide hydrophobic and hydrophilic polymers can be used to crosslink the tissue.

Example 9

Crosslinking of Unsaturated Group Modified Tissue Using Functional Monomer

Two 1 cm by 1 cm pieces of unsaturated group modified bovine pericardium tissue prepared per example 1 are incubated for 30 minutes each in 20% ethanol, 50% ethanol and 70% ethanol. 50 mg of 2,2-demethoxy-2-phenyl acetophenone (free radical photoinitiator) is dissolved in 0.5 ml glycidyl methacrylate (monomer containing epoxy group) and 0.5 ml n-vinyl pyrrolidone. The 70% ethanol incubated tissue is transferred to glycidyl methacrylate solution and incubated for 4 h at 25° C. and then for 12 h at 0° C. The tissue is removed from solution is placed on a glass plate and exposed to Black-Ray UV lamp (360 nm light, 10000 mW/cm2 intensity) for 15 minutes each side. The crosslinked tissue is washed with water and 100 percent methanol to remove water and organic soluble impurities. The epoxy functionality of glycidyl may be further used to introduce other chemical moieties such as, by way of example, and not limitation, bioactive compounds or it may, for example, and without limitation, be used to further crosslink the tissue using di- or polyfunctional amines such as, by way of example, and not limitation, hexamethylene diamine.

Example 10

Crosslinking of Unsaturated Group Modified Tissue Using Monomers that Produce Elastomeric Polymers Crosslinking Using poly(dimethyl siloxane) Based Monomer 50 mg of 2,2-demethoxy-2-phenyl acetophenone (free radical photoinitiator) is dissolved in 0.2 Poly(dimethylsiloxane), vinyl terminated (Sigma-Aldrich Product Number: 43, 301-2) and 0.8 ml n-vinyl pyrrolidone. Two 1 cm by 1 cm pieces of unsaturated group modified bovine pericardium tissue prepared per example 1 are incubated for 30 minutes each in 20% ethanol, 50% ethanol and 70% ethanol and finally in Poly(dimethylsiloxane) solution prepared as indicated earlier. The tissue is removed from solution and is placed on a glass plate and exposed to Black-Ray UV lamp (360 nm light, 10000 mW/cm2 intensity) from both sides. The crosslinked tissue is washed with water and 100 percent methanol to remove water and organic soluble impurities. Incorporation of synthetic silicone based rubber can assist to improve mechanical properties of the tissue and improve oxygen permeability.

Example 11

Tissue Modified with Thermosensitive Polymer

Crosslinking of Acrylic Modified Tissue Using Monomer that Produces Thermosensitive Polymer/Hydrogel 50 mg of 2,2-demethoxy-2-phenyl acetophenone (free radical photoinitiator) is dissolved in 0.4 ml n-vinyl pyrrolidone and 0.6 g n-isopropylacrylamide. Two 1 cm by 1 cm pieces of acrylic acid succinimide ester modified or glycidyl methacrylate modified bovine pericardium tissue prepared per example 1 or 37 is incubated for 30 minutes each in 20% ethanol, 50% ethanol and 70% ethanol and finally n-vinyl pyrrolidinone solution. The tissue is then transferred to n-isopropylacrylamide solution in n-vinyl pyrrolidinone (40%) containing 1000 ppm Irgacure 2959 and incubated for 4 h. The tissue is removed from solution is placed on a glass plate and exposed to Black-Ray UV lamp (360 nm light, 10000 mW/cm2 intensity) for 5 minutes each side. The exposed tissue is washed with 100% alcohol to remove unreacted monomers and initiator fragments and then incubated in cold PBS solution (4° C.) for 24 hours. The polymerized n-isopropylacrylamide absorbs water at low temperature (4° C.) and also permits collagen chains to re-hydrate. The fully absorbed tissue is incubated in PBS maintained at 37° C. At 37° C., n-isopropylacrylamide turns hydrophobic but collagen chains remain hydrated. Alternatively, a 20-50 percent n-isopropylacrylamide solution in water may also be used in place of ml n-vinyl pyrrolidone and n-isopropylacrylamide mixture for polymerization and crosslinking reaction using 500 ppm Irgacure 2959 as photoinitiator.

Example 12

Bioprosthetic Tissue and Polyvinyl Alcohol Composite

Crosslinking of Unsaturated Group Modified Tissue Using Vinyl Acetate which is Converted into Polyvinyl Alcohol Vinyl acetate is vacuum distilled prior to use to remove polymerization inhibitor. 50 mg of 2,2-demethoxy-2-phenyl acetophenone (free radical photoinitiator) is dissolved in 1 ml inhibitor free vinyl acetate. Two 1 cm by 1 cm pieces of acrylic acid succinimide ester modified bovine pericardium tissue prepared per example 1 are incubated for 30 minutes each in 20% ethanol, 50% ethanol and 70% ethanol and n-methylpyrrolidinone. The tissue is then transferred to vinyl acetate solution and incubated for 4 h. The tissue is removed from solution and then placed on a glass plate and exposed to Black-Ray UV lamp (360 nm light, 10000 mW/cm2 intensity) for 15 minutes each side. The exposed tissue is washed with 100% alcohol to remove unreacted monomers and initiator fragments. The tissue is then incubated in 1% p-toluene sulfonic acid solution in water to hydrolyze polyvinyl acetate. Briefly, the treated tissue is incubated in 10 ml distilled water containing 100 mg p-toluene sulfonic acid at 50° C. for 3 days.

Using a similar procedure, acrylonitrile monomer can be can be used in place of vinyl acetate in tissue crosslinking. The nitrile groups in polymerized polyacrylonitrile can be partially or completely hydrolyzed under mild acidic/basic conditions to produce a mechanically strong polyacrylonitrile-co-polyacrylic acid hydrogel in the tissue matrix.

Example 13

Crosslinked Tissue Complexed with Biologically Active Compounds or Synthetic Polymers Iodine solution is prepared by dissolving elemental iodine (0.1%) and potassium iodide (0.4%) in 10% ethanol. Vinyl pyrrolidinone crosslinked tissue (prepared per Example 5 or 37) is incubated with iodine solution for 3 hours at 25° C. temperature and is then removed from the solution and washed with PBS solution. The iodine complexes with polyvinylpyrrolidinone in the treated tissue. The brown color of iodine-PVP complex is noticeable on the tissue surface. The iodine complexed tissue may be applied on a wound and the iodine released in the wound area is used to control infection or bacterial growth. Other compounds that form complex with polyvinyl pyrrolidinone such as, by way of example, and not limitation, antibiotics may also be used.

Example 14

Tissue and Biodegradable Polymer Composite

Tissue and Biodegradable Polymer Composite wherein the Biodegradable Polymer is Crosslinked Crosslinking of Acrylic Modified Tissue Using Biodegradable Multifunctional Macromonomer (Water-Soluble)

Part 1: Synthesis of Polyethylene Glycol Lactate Copolymer (10KL5)

30.0 g of PEG 10000, 4.3 g of dl-lactide and 30 mg of stannous octoate are charged into 100 ml Pyrex pressure sealing tube. The tube is then connected to an argon gas line and sealed under argon. The tube is then immersed in oil bath maintained at 140° C. The reaction is carried out for 16 h at 140° C. The polymer from the tube is recovered by breaking the Pyrex tube. The polymer is then dissolved in 70 ml toluene and precipitated in 2000 ml cold hexane. The precipitated polymer is recovered by filtration and dried under vacuum for 1 day at 60° C. It is then immediately used in the next reaction.

Part 2: End-Capping of 10KL5 with Polymerizable or Crosslinkable Group (10KL5A2)

30 g of 10KL5 is dissolved in 450 ml dry toluene. About 50 ml of toluene is distilled out to remove traces of water from the reaction mixture. The warm solution is cooled to 65° C. To this warm solution, 1.6 g of triethyl amine and 1.5 g acryloyl chloride are added. The reaction mixture is then stirred for 30 minutes at 50-60° C. and filtered. The reactive precursor is precipitated by adding the filtrate to 2000 ml cold hexane. The precipitated polymer is recovered by filtration. It is then dried under vacuum for 12 h at 50° C.

Part 3: Crosslinking of Acrylic Modified Tissue Using 10KL5A2

50 mg of 2,2-demethoxy-2-phenyl acetophenone (free radical photoinitiator) is dissolved in 0.9 ml n-vinyl pyrrolidone (NVP) and 0.1 g 10KL5A2. Two 1 cm by 1 cm pieces of acrylic acid succinimide ester modified bovine pericardium tissue prepared per examples 1 to 4 is incubated for 30 minutes each in 20% ethanol, 50% ethanol and 70% ethanol and n-vinyl pyrrolidinone. The tissue is then transferred to 10KL5A2 solution and incubated for 4 h. The tissue is removed from solution is placed on a glass plate and exposed to Black-Ray UV lamp (360 nm light, 10000 mW/cm2 intensity) for 15 minutes each side. The exposed tissue is washed with 100% alcohol to remove unreacted monomers and initiator fragments and then incubated in cold PBS solution (4° C.) for 24 hours. The lactate ester bonds in the polymerized 10KL5A2 hydrolyze in presence of water and make the tissue susceptible for enzymatic degradation. The ratio of NVP to 10KL5A2 could be changed to control biodegradation, swelling and other properties of the tissue/polymer composite matrix.

In another variation of this procedure, a bioactive compound such as, by way of example, and not limitation, heparin may be added in the monomer mixture prior to photopolymerization. The bioactive compound is released as 10KL5A2 undergoes hydrolysis. In another variation of this method, 5 ml of 20% solution of 10KL5A2 in PBS containing 400 ppm Irgacure 2959 is used to suspend 1 million human fibroblast cells. The unsaturated group modified tissue is incubated for 30 minutes in the polymer solution. The solution is taken out and about 0.2 ml solution is sprayed on the tissue surface. The solution on the surface and tissue are exposed to 2 minutes with Black-Ray UV lamp (360 nm light, 10000 mW/cm2 intensity). The polymerized 10KL5A2 with encapsulated cells is clearly seen on the tissue surface. Most of the cells remained viable and tolerate the encapsulation process.

Example 15

Tissue and Biodegradable Polymer Composite

Tissue and Biodegradable Polymer Composite wherein the Biodegradable Polymer is Hydrophobic Crosslinking of Acrylic Modified Tissue Using Biodegradable Multifunctional Macromonomer (Water-Insoluble or Substantially Water Insoluble)

Part 1: Preparation of Trifunctional Lactate Liquid Copolymer (TMPTL).

Trimethylol propane triol (TMPT) is dried under vacuum at 60° C. for 16 hours. 2 g of dry TMPT, 17.5 g of dl-lactide, and 20 mg of stannous octoate are charged into a 3 necked flask equipped with Teflon coated magnetic stirring needle and nitrogen inlet. The flask is then immersed in a silicone oil bath maintained at 160° C. The reaction is carried out for 5 h under nitrogen atmosphere. The reaction mixture is then cooled to room temperature. The mixture is then dissolved in 10 ml toluene. The hydroxyl-terminated liquid lactate polymer is isolated by pouring the toluene solution in large excess cold hexane. It is further purified by repeated dissolution-precipitation process from toluene-hexane solvent-nonsolvent system and dried under vacuum at 60° C. It is then immediately used for acrylate end capping reaction described below.

Part 2: End Capping of Trifunctional Polylactide Polymer with Acrylate Group (TMPTLA).

10 g of TMPT initiated lactate synthesized previously is dissolved in 150 ml dry benzene. From this solution 20 ml benzene is distilled out to remove unwanted moisture from the reaction mixture. The solution is cooled to 0° C. in ice bath. 2.7 ml of triethyl amine and 1.8 ml acryloyl chloride are added dropwise to the cold lactate solution. The mixture is refluxed under nitrogen atmosphere for 3 h. The solution is filtered to remove triethylamine hydrochloride. The acrylate ester is then isolated by pouring the filtered solution in large excess cold hexane. It is further purified by repeated (3 times) precipitation from toluene-cold hexane system. The liquid polymer is dried under vacuum at 40° C. It is stored in an amber-colored bottle under nitrogen atmosphere.

Part 3: Crosslinking of Acrylic Modified Tissue Using TMPTLA.

50 mg of 2,2-demethoxy-2-phenyl acetophenone (free radical photoinitiator) is dissolved in 0.9 ml n-vinyl pyrrolidone and 0.1 g TMPTLA. Two 1 cm by 1 cm pieces of acrylic acid succinimide ester modified bovine pericardium tissue prepared per example 1 are incubated for 30 minutes each in 20% ethanol, 50% ethanol and 70% ethanol and n-vinyl pyrrolidinone. The tissue is then transferred to TMPTALA solution and incubated for 4 h. The tissue is removed from the solution is placed on a glass plate and exposed to Black-Ray UV lamp (360 nm light, 110000 mW/cm2 intensity) for 5 minutes each side. The exposed tissue is washed with 100% alcohol to remove unreacted monomers and initiator fragments and then incubated in cold PBS solution (4° C.) for 24 hours. The lactate ester bonds in the polymerized TMPTALA hydrolyze in presence of water and make the tissue susceptible for enzymatic degradation.

Example 16

Tissue-Synthetic Biodegradable Crosslinkable Polymer Composite

Five 1 cm by 1 cm pieces of acrylic acid succinimide ester modified bovine pericardium tissue are cryogenically ground (at liquid nitrogen temperature) to make a tissue powder. 50 mg of 2,2-demethoxy-2-phenyl acetophenone (free radical photoinitiator) is dissolved 0.1 ml n-vinyl pyrrolidone and 0.9 g TMPTLA. 1 g of tissue powder is mixed with 200 mg TMPTLA monomer and 1 g sodium chloride (to induce porosity) and the mixture poured into a mold cavity. The shape of the cavity is similar to shape of human meniscus tissue. The mixture in the cavity is exposed to Black-Ray UV lamp (360 nm light, 10000 mW/cm2 intensity) for 15 minutes to cure the TMPTLA polymer. The cured product is washed with 100% ethanol to remove unreacted monomer and then with water to remove sodium chloride (to induce porosity). The cured tissue/synthetic polymer can be used as a biodegradable meniscus implant or a scaffold for tissue engineering.

Collagen protein powder modified with unsaturated groups per Examples 1-4 may also be used in place of tissue powder.

Example 17

Crosslinking of Unsaturated Group Modified Tissue Using Di or Polyfunctional Mercapto Compounds In this crosslinking method, mercapto group from the crosslinker react with unsaturated group in the modified tissue (Examples 1-4) and produce a crosslinked tissue.

In a 50 ml polypropylene tube, 7.5 ml 50 mM sodium bicarbonate buffer (pH 9-12) and 2.5 ml acetonitrile are mixed. Five 1 cm by 1 cm pieces of acrylic acid succinimide ester modified bovine pericardium tissue (Examples 1-3) are suspended in the acetonitrile solution. 0.2 ml trimethylolpropane tris(3-mercaptopropionate) (Sigma-Aldrich Product Number: 38, 148-9) is added to the tube and the mixture is vortexed for 60 minutes. The reaction is continued for 6 h at room temperature and 12 hours at 4° C. The tissue is separated from the mixture, washed with PBS and 100% ethanol and then finally stored in 100% ethanol until use.

Example 18

Crosslinking of Tissue with Biodegradable Crosslinker

Crosslinking of Tissue Using Non-Polymeric Degradable Crosslinker

Synthesis of a Biodegradable Crosslinker; Hydroxylamine Succinate NHS Ester

Part 1: Hydroxylamine Succinate

To a solution of 2 g hydroxy amine in 100 ml dry benzene and 100 ml pyridine, 9.4 g succinic anhydride are added and the reaction mixture stirred at room temperature for 2 h and then refluxed for 2 h. The solvent is evaporated under vacuum and the residue is purified by flash chromatography using silica gel.

Part 2: Hydroxylamine Succinate NHS Ester.

Part 2: To a cold (4° C.) solution of 5 g Hydroxylamine Succinate and 5.1 g n-hydroxysuccinimide in 120 DMF, 11.8 g 1,3-dicyclohexyl carbodiimide in 30 ml of DMF and is added under nitrogen atmosphere. The reaction is continued at room temperature for 8 h and urea precipitate is filtered. The filtrate is evaporated and the crude compound is recovered. The compound is further purified by flash chromatography.

Part 3: Crosslinking of Pericardial Tissue with Hydroxylamine Succinate NHS Ester.

10 pieces of 1 cm by 1 cm bovine pericardium pierces are transferred to 50 ml polypropylene centrifuge tube containing 10 ml PBS. 250 mg Hydroxylamine Succinate NHS ester in 0.5 ml dimethyl sulfoxide is added to the tube and the solution is vortexed for 15 minutes. The modification reaction is carried for 6 hours at ambient temperature (25° C.) and then for 12 hours at 4° C. with gentle shaking. The reaction is terminated by washing the tissue with 20 ml distilled water 3 times. Finally, the tissue is lyophilized and stored at −20° C. until use.

The ester linkage hydroxylamine succinate in the crosslinker is hydrolyzed when exposed to physiological conditions such PBS, pH 7.2. The hydrolyzed tissue degrades by normal enzymatic degradation.

Example 19

Crosslinking Using Polymeric Degradable Crosslinker 10 pieces of 1 cm by 1 cm bovine pericardium tissue are transferred to 50 ml polypropylene centrifuge tube containing 10 ml PBS. 1.0 g 4 arm-n-hydroxysuccinimide ester of polyethylene glycol carboxymethylene-butyric acid, average molecular weight 10000 Daltons (obtained from Shearwater Polymers, 4 arm, product CM-HBA-NS-10K) is added to the tube and the mixture is vortexed for 5 minutes. The tissue is isolated from the tube, washed with distilled water and used as a biodegradable matrix for various medical and tissue engineering applications. Upon implantation, the glutarate ester bond in CM-HBA-NS-10K undergoes hydrolysis. After hydrolysis of the crosslinker, tissue degrades by a normal enzymatic pathway. Additional crosslinking agents such as crosslinking with EDC may also be used to control tissue properties or degradation time.

Example 20

Bioprosthetic Tissue Incorporated with Crosslinked Biodegradable Hydrogel

Part 1: Synthesis of Polyethylene Glycol Lactate Copolymer (PEG20KL5).

50 g PEG molecular weight 20000 is dried at 120° C. under vacuum for 10 hours. 10.0 g dry PEG molecular weight 20000, 2.2 g of dl-lactide and 100 mg of stannous octoate are charged into 100 ml flame dried round bottom flask. The flask is then connected to an argon gas line and then immersed in an oil bath maintained at 160° C. The polymerization reaction is carried out for 16 h at 160° C. The polymer is then dissolved in 100 ml toluene and precipitated in 2000 ml cold hexane. The precipitated polymer is recovered by filtration and dried under vacuum for 1 day at 60° C. It then immediately used in next step.

Part 2: End-Capping of PEG20KL5 with Polymerizable or Crosslinkable Group (PEG20KL5A).

30 g of PEG20KL5 is dissolved in 450 ml dry toluene. About 50 ml of toluene is distilled out to remove traces of water from the reaction mixture. The solution is cooled to 65° C. To this warm solution, 0.6 g of triethyl amine and 0.5 g acryloyl chloride are added. The reaction mixture is then stirred for 30 minutes at 50-60° C. and filtered. The reactive crosslinkable precursor is precipitated by adding the filtrate to 2000 ml cold hexane. The precipitated polymer is recovered by filtration. It is then dried under vacuum for 12 h at 50° C.

Part 3: Incorporation of Hydrophilic Crosslinkable Biodegradable Polymer in the Pericardial Tissue.

A 3 cm×3 cm piece is cut from a cleaned uncrosslinked bovine pericardial sac. The tissue is then incubated for 30 minutes each in 20% ethanol, 40% ethanol, 80% ethanol and finally in 100% ethanol. In a 500 ml beaker, 10 g PEG20KL5A, 0.5 g Chlorhexidene Gluconate, 0.050 g Irgacure 2959 are dissolved in 90 g methanol. The 100% ethanol-treated tissue is transferred into Chlorhexidene Gluconate solution and is incubated for 2 hours. The tissue is removed from the solution and exposed to long UV light emitting at 360 nm for 5 minutes (Black-Ray light source, model 3-100A, Flood 365 nm, intensity 30 mW/cm2).

Example 21

Bioprosthetic Tissue-Hydrophilic Non-Crosslinked Biodegradable Polymer Composite Biodegradable Tissue Based Patch for Controlled Drug Delivery Part 1: Synthesis of Polyethylene Glycol Lactate Copolymer (PEG8K50)

50 g PEG molecular weight 8000 (Carbowax 8000) is dried at 120° C. under vacuum for 10 hours. 10.0 g dry PEG molecular weight 8000, 18.0 g of dl-lactide and 10 mg of stannous octoate are charged into 100 ml flame dried round bottom flask. The flask is then connected to an argon gas line and then immersed in an oil bath maintained at 160° C. The polymerization reaction is carried out for 16 h at 160° C. The polymer is then dissolved in 100 ml toluene and precipitated in 2000 ml cold hexane. The precipitated polymer is recovered by filtration and dried under vacuum for 1 day at 60° C.

Part 2: Incorporation of Hydrophilic Non-Crosslinked Biodegradable Polymer (PEG8K50) in the Pericardial Tissue.

A 3 cm×3 cm piece is cut from a cleaned uncrosslinked bovine pericardial sac. The tissue is incubated for 30 minutes each in 20% ethanol, 40% ethanol, 80% ethanol and finally in 100% ethanol. In a 500 ml beaker, 10 g polyethylene glycol-lactate copolymer (PEG8K50), and 1 g rifampin are dissolved in 90 g chloroform. The 100% ethanol-treated tissue is transferred into rifampin solution and is incubated for 2 hours. The tissue is removed from the solution and the solvent is evaporated by air drying. The reddish yellow rifampin-PEG-lactate coating is clearly visible to the naked eye. The dry tissue is sterilized using ethylene oxide and used as a biodegradable drug delivery patch. The polyethylene glycol-lactate polymer acts as a hydrophilic non-crosslinked biodegradable polymeric drug delivery matrix for Rifampin.

The tissue may be mechanically resurfaced or perforated to improve the adhesion of polymer to the tissue.

The same procedure may also be used to incorporate biodegradable polymer in glutaraldehyde crosslinked tissue or EDC crosslinked tissue.

Example 22

Incorporation of Hydrophobic Non-Crosslinked Synthetic Biodegradable Polymer in the Pericardial Tissue Biodegradable Tissue Based Patch for Controlled Drug Delivery Seven 1 cm×1 cm pieces are cut from a cleaned uncrosslinked bovine pericardial sac. The tissue is then incubated for 30 minutes each in 20% ethanol, 40% ethanol, 80% ethanol and finally in 100% ethanol and dried.

In a 50 ml beaker, 200 mg polylactide-co-polyglycolide (50:50), molecular weight 50000 (Sigma-Aldrich Catalog number 43,044-7) is dissolved in 3 ml chloroform. 20 mg rifampin is added to the polymer solution. The 100% ethanol treated tissue is transferred into rifampin solution and is incubated for 2 hours. The tissue is removed from the solution and the chloroform is evaporated by air drying. The reddish yellow rifampin-polymer coating is clearly visible to the naked eye. If necessary, vacuum drying may, for example, and without limitation, be used to completely remove the chloroform. Finally the tissue is sterilized using ethylene oxide.

Two pieces of rifampin-treated tissue are incubated in 2 ml PBS at 37° C. and the release of rifampin is monitored over a period of 72 hours. The PBS is exchanged at 10 minutes, 6 hours, 24 hours, 48 hours and 72 hours time intervals. All incubated solutions had light yellow color visible to the naked eye indicating the presence of rifampin in the solution. The concentration of rifampin in the eluted solution is analyzed by UV-VIS spectrophotometry.

Using a similar method, a high molecular weight polydl-lactide, molecular weight 100000 (Sigma-Aldrich Catalog Number 53, 116-2) is used in place of polylactide-co-polyglycolide (50:50) to form a tissue-biodegradable polymer composite. This polymer takes a much longer time to degrade and shows a different rifampin release profile.

The biodegradable polymer used could be liquid or low melting solid. Using similar methods to those described above, a non-polymeric drug carrier such as, by way of example, and not limitation, sucrose acetate or vitamin E or vitamin E acetate may be also used as a carrier and incorporated in the tissue. If a biostable tissue is matrix is desired, then a crosslinked tissue such as, by way of example, and not limitation, glutaraldehyde crosslinked tissue may, for example, and without limitation, be used in place of non-crosslinked tissue.

Example 23

Porcine Pericardial Patch Coated with Biodegradable Polymer (Synthetic Biodegradable Hydrogel)

From a freshly obtained piece of porcine pericardial sac, A 3 cm×3 cm piece of tissue is cut. This tissue is incubated in 1% Eosin Y solution in PBS for 10 minutes. The tissue is rinsed with fresh PBS to remove excess of eosin solution from the tissue and used in the coating process.

20 g 10KL5A2 (Example 14), 80 g saline solution buffered with 1000 mM triethanol amine buffer (pH 7.4) and 1 ml vinyl pyrrolidinone are mixed in 1000 ml beaker. Eosin stained pericardial tissue is placed inside the solution. Care is taken to completely cover the tissue surface with 10 KL5A2 solution. The tissue is then exposed to 514 nm light either from argon laser (American Argon ion laser, Model 905 emitting at 532 nm, 100 mW/cm2) or xenon lamp (intensity 0.5 W/cm2). The eosin-triethanolamine-10KL5A2-light initiates a photopolymerization reaction at the tissue interface forming a thin hydrogel film on the tissue surface. The thickness of the film is dependent on the exposure time, monomer concentration, eosin concentration and light intensity. A 5 to 2000 micron coating is obtained. The biodegradable hydrogel coated tissue can be used as a coated tissue patch. If necessary, multiple eosine and monomer solution treatments may be performed to achieve a desirable thickness.

Using a similar approach to that described above, an albumin modified with polymerizable groups may, for example, and without limitation, be used to coat tissue surface. The albumin may be bovine albumin or human albumin. The human albumin may be obtained by recombinant technology.

A crosslinked tissue such as, by way of example, and not limitation, glutaraldehyde crosslinked tissue may, for example, and without limitation, be used in place of uncrosslinked tissue if a biostable material is desired.

Example 24

Porcine Pericardial Patch Coated with Synthetic Biodegradable Polymer Hydrogel Formed by Condensation Polymerization An ethylene oxide sterilized air assisted sprayer is used in conjunction with aqueous solutions of polymerizable monomers. Solution consisted of a 14.4% solution of 4 arm-n-hydroxysuccinimide ester of polyethylene glycol carboxymethylene-butyric acid, average molecular weight 10000 Daltons (Shearwater 4 arm CM-HBA-NS-10K) is dissolved in 0.01M phosphate buffer at pH 4.0 and is sterile-filtered (Pall Gelman syringe filter, p/n 4905) and drawn up in a sterile 5 cc syringe. Solution 2 consisted of a 1.2% solution of a dilysine (purchased from Sigma Chemicals) dissolved in 0.1M borate buffer at pH 11 with 0.5 mg/mL methylene blue for visualization and is also sterile-filtered and drawn up in a sterile 5 cc syringe. These solutions, when combined 1:1 on a volumetric basis, result in a 1:1 ratio of NHS ester to amine end group. The final % solids after combination is 7.5%. The two syringes are individually loaded in the two separate receptacles through a luer-lok type of linkage. Airflow from a regulated source of compressed air (an air compressor such as, by way of example, and not limitation, those commercially available for airbrushes) is connected to the device using a piece of Tygon tube. On compressing the syringe plungers a steady spray of the two liquid components is observed. A 10 cm×5 cm piece is cut from a cleaned uncrosslinked bovine pericardial sac or AlloDerm® tissue marketed by LifeCell Corporation, NJ. The spray from the syringe is directed to the piece of pericardial tissue, and a hydrogel coating is formed on the surface of the tissue. Alternatively, the coating compositions and spray system can be purchased as DuraSeal from Confluent Surgical Inc., MA and used. Within a short period of time (less than a minute) an area of 10 cm×5 cm could be coated with ease. The coating can be applied on both the sides of the tissue. The polyethylene glycol coating makes the tissue surface non-cell adhesive. The hydrogel coating is rinsed with saline (the hydrogel coating is resistant to rinsing) and is observed to be well adherent to the tissue surface. The hydrogel coating can be used to modify biological properties of the tissue. If the coating is applied on one side only, then one surface (coated surface) becomes non-cell adhesive while the uncoated surface remains as a cell adhesive surface. The coating can also be used to deliver drugs in a controlled manner. This is achieved by adding drug or drug encapsulated microspheres in a coating formulation before coating the tissue or by incubating the coated patch in drug solution in organic solvent or water and then removing the solvent. The coated tissue can be used as a barrier for reducing surgical adhesions. Such a non-cell adhesive tissue patch can be used to reduce post-operative adhesions. The coated tissue loaded with BMP proteins could be used to generate a bone tissue.

A crosslinked tissue such as, by way of example, and not limitation, glutaraldehyde crosslinked tissue may, for example, and without limitation, be used on place of uncrosslinked tissue if a biostable material is desired.

Example 25

Prevention of Post-Operative Adhesions Using Coated Tissue Patch or Composite Tissue Patch Rat Cecum Model Fourteen Sprague Dawley rats with average weight around 260 g are divided into 2 groups, 7 animals in each group. After following the standard procedures for administrating anesthesia, a midline incision is made on the abdomen and a cecum is located in the abdominal cavity. Using a standard surgical cotton gauze pad, an injury is made to the Cecum surface by abrading the surface of cecum. The approximate area of injury is maintained around 1-2 sq. cm. The injury elicits some bleeding from the injured surface. A porcine pericardial tissue-coated with PEG based hydrogel or DuraSeal based hydrogel is wrapped around the injured surface (Examples 20-24, preferably example 24). Composite patch made using polytetrafluoroethylene (PTFE) membrane and membrane tissue wherein PTFE membrane serves as non-cell adhesive layer and tissue serve as cell adhesive layer may also be used. The coated tissue is wrapped around the injured area such that non-adhesive surface is facing to the injured surface and immobilized by suturing it either to itself or by suturing it to abdominal wall. Care is taken to ensure that a hydrogel surface or PTFE in place of a composite is completely covering the injured cecum surface. 7 animals are treated with coated tissue and 7 animals are used as controls which did not receive any tissue composite. The animals are closed after the treatment using sutures and staples, topical antibiotic is applied and the animals are subjected to standard diet and care as recommended by National Institute of Health. After 14 days the rats are subjected to CO2 asphyxiation.

The incisions are reopened and the cecum is observed for the adhesions in the area of injury. The adhesions are scored as the percent injured area involved in adhesion formation with the surrounding organs and peritoneal wall. The results of treated and control animals are analyzed using standard statistical methods (t-test).

Coated or composite tissue patch prepared as above may be used in hernia surgery to reduce complications due to surgical adhesions.

Example 26

Chemical Modification of Tissue without Crosslinking

Modification of Uncrosslinked Tissue Using Monomethoxy Polyethylene Glycol Derivatives Part 1: Synthesis of Monomethoxy Polyethylene Glycol Succinic Ester. Conversion of PEG Hydroxyl Groups into Carboxylic Groups.

10 g monomethoxy polyethylene glycol, molecular weight 400 (PEG-400M) is dried at 60° C. overnight under vacuum prior to use. 10 g PEG-400M is dissolved in 35 ml dry pyridine and 35 ml benzene. 3.5 g succinic anhydride or 4.0 g of glutaric anhydride is added to it and the solution is refluxed for 2 h under nitrogen atmosphere. Most of the pyridine is distilled out and the polymer is isolated by pouring the cold concentrated pyridine solution to cold 4000 ml hexane and dried under vacuum at 60° C. and used immediately in a subsequent carboxyl group activation reaction.

Part 2: Activation of Acid Group Using n-Hydroxysuccinimide (PEG-400MNHS).

To a solution of 10 g of PEG-400M succinate or glutarate in 100 ml dry methylene chloride are added 2.5 g n-hydroxysuccinimide and 5.9 g 1,3-dicyclohexyl carbodiimide. The reaction mixture is cooled to 0° C. using ice bath and stirred overnight under nitrogen atmosphere. Dicyclohexylurea is removed by filtration. The filtrate is evaporated and the residue obtained is redissolved in 10 ml toluene. The toluene solution is precipitated in 2000 ml cold hexane.

Alternatively, monomethoxy PEG NHS derivates may be purchased from Sigma-Aldrich or Sherewater Inc.

Part 3: Modification of Tissue Using Monomethoxy Polyethylene Glycol Succinic Ester (PEG-400MNHS)

Porcine pericardial sac is obtained from a local abbotair and is cleaned to remove blood and fatty tissue from the surface. Ten 1 cm by 1 cm pieces are cut from the cleaned pericardial sac and transferred to 10 ml 20 mM phosphate buffer solution (PBS, pH 7.2).

200 mg monomethoxy polyethylene glycol succinic ester or glutaric ester (PEG-400MNHS, part 2) is added to the tissue/PBS mixture. The solution is vortexed for 5 minutes and tissue is incubated at room temperature for 5 minutes to 12 hours, preferably 6 hours. The tissue is separated from the crosslinker mixture and washed with 20 ml PBS solution 3 times to remove unreacted chemicals. The PEG-modified tissue shows does not show significant increase in shrink temperature and the modified tissue degrades when exposed to collagenase or pepsin solution for prolonged periods of time indicating its susceptibility to enzymatic degradation.

The tissue treatment can be done just prior to surgical implantation if the PEG derivative, tissue and PBS is provided as a kit.

Example 27

Chemical Modification of Tissue Without Crosslinking

Modification of Uncrosslinked Tissue Using Anhydrides

Porcine pericardial sac is obtained from a local abbotair and is cleaned to remove blood and fatty tissue from the surface. Ten 1 cm by 1 cm pieces are cut from the cleaned pericardial sac and transferred to 10 ml 20 mM sodium borate buffer (pH 9.5). 0.5 g succinic anhydride is added to the tube. The solution is vortexed for 5 minutes and tissue is incubated at room temperature for 12 hours. The tissue is separated, washed and stored until use.

Using a similar reaction scheme, the tissue is modified using 0.5 g acetic anhydride or 0.5 g glutaric anhydride. Briefly, two 1 cm by 1 cm pieces of bovine pericardium tissue are incubated for 30 minutes each in 20% ethanol, 50% ethanol and 70% ethanol and n-methyl pyrrolidinone. The tissue is then transferred to a 50 ml flask containing 5 ml n-methyl pyrrolidinone, 0.5 g acetic anhydride and 0.5 g triethyl amine. The tissue is incubated for 6 h at 40° C. and then removed. It is washed with 20 ml 100% ethanol and 20 ml PBS.

Example 28

Chemical Modification of Tissue Without Crosslinking

Modification of Uncrosslinked Porcine Pericardial Tissue Using Activated Acid (Acetic Acid n-Hydroxy Succinimide Ester)

Porcine pericardial sac is obtained from a local abbotair and is cleaned to remove blood and fatty tissue contaminants from the tissue surface. Ten 1 cm by 1 cm pieces are cut from the cleaned pericardial sac and transferred to 10 ml 0.20 M 2-(N-morpholino)ethanesulfonic acid (MES) buffered solution (pH 6.5). 0.5 g Acetic acid n-hydroxy succinimide ester) AANHS is added to the buffered solution and the reaction is vortexed for 15 minutes and continued for 6 hours at ambient temperature. An additional 0.1 g AANHS ester is added to the mixture at every 1.5 hours. After the reaction, the tissue is isolated and washed several times with PBS and finally stored in 50% ethanol solution. The treated tissue is sterilized using ethylene oxide.

The modified tissue is degradable upon implantation. The tissue becomes less inflammatory due to chemical modification.

The tissue treatment can be done just prior to surgical implantation if the acetic acid n-hydroxy succinimide ester, tissue and PBS is provided as a kit.

Example 29

Shape Preserving Tissue Fixation Methods and Devices a) Preparation of Helical Coil Shaped Tissue (Tissue Stent)

Untreated long bovine pericardium (BP) tissue strips (approximately 10 to 20 cm long and 2-4 mm wide) are transferred to a 500 ml flask containing 100 ml PBS, 12.5 ml triethylamine (TEA) and 12.5 ml glycidyl methacrylate (GM). The solution was heated to 50° C. with constant stirring using magnetic stir bar and held there for 8 hours. The tissue strips are removed from the solution and washed with PBS, distilled water, & incubated in 70% isopropanol solution in water for 30 minutes. Finally, strips are then transferred to a tetraethyleneglycol dimethacrylate (TEGDM) monomer containing 500 ppm 2,2-dimethoxy 2-phenyl acetophenone (photoinitiator) and incubated at room temperature (30° C.) for one hour. One TEGDM infused strip is helically or spirally wound on a 6 mm diameter glass rod. Both ends of the strip are tied with a thread to prevent unwinding. The helically wrapped monomer infused tissue strip was then exposed to 360 nm light (Black-Ray UV lamp, 360 nm flood light, 10000 mW/cm2 intensity at a distance of 10 cm) for 10 minutes while gently rotating to expose the tissue from all sides. The coiled tissue was removed from the glass rod and was washed with PBS and 70% isopropanol to remove unreacted monomer and initiator fragments. The tissue preserved the helical shape after removal of glass rod mandrel support.

b) Preparation of Compressible or Wrinkled Tube from Membrane Like Tissue.

Preparation of Compressible Vascular Graft from Flat Tissue Such as, by Way of Example, and not Limitation, Pericardial Tissue or Submucosa Tissue Untreated long bovine pericardium (BP) tissue strips (approximately 18 to 20 cm long and 15-18 mm wide) are transferred to a 500 ml flask containing 250 ml PBS, 32 ml triethylamine (TEA) and 32 ml glycidyl methacrylate (GM). The solution was heated to 50° C. with constant stirring using magnetic stir bar and held there for 8 hours. The tissue strips are removed from the solution and washed with PBS, distilled water, & incubated in 70% isopropanol solution in water for 30 minutes. Finally, strips are then transferred to a 50% n-vinyl pyrrolidinone (NVP) solution in water containing 500 ppm 2,2-dimethoxy 2-phenyl acetophenone (photoinitiator) and incubated at room temperature (30° C.) for 1 hour. The NVP infused tissue strip is wrapped on a 6 mm diameter stainless steep screw having threads. The tissue was compressed in such a manner that it took shape of a threaded region of the screw. Both ends of the strip are tied with thread to prevent unwinding. The helically-wrapped monomer-infused tissue strip was then exposed to 360 nm light (Black-Ray UV lamp, 360 nm flood light, 10000 mW/cm2 intensity at a distance of 10 cm) for 10 minutes while gently rotating to expose the tissue from all sides. The tissue was removed from the rod and was washed with PBS and 70% isopropanol to remove unreacted monomer and initiator fragments. The tissue duplicated the shape of the threaded screw. This tissue was sewn to make 5 mm diameter tube. The tubular tissue was compressible similar to commercially available polyester based vascular grafts.

In another approach, a pericardial tissue patch modified with glycidyl methacrylate (see example 37 described below) and infused with tetraethyleneglycol dimethacrylate (TEGDM) monomer containing 500 ppm 2,2-dimethoxy 2-phenyl acetophenone (photoinitiator) was converted into a 6 mm diameter 10 cm long tube. The tube was mounted on a 6 mm diameter stainless steel mandrel/rod. The mounted tube was compressed along the axis of the tube to reduce the its length from 10 cm to 7 cm (30% compression). The tube has several wrinkles uniformly distributed along the axis of the tube. The compressed tube was then exposed to UV light (Black-Ray UV lamp, 360 nm flood light, 10000 mW/cm2 intensity at a distance of 10 cm) for 10 minutes while rotating the tube. The crosslinked tube was removed from the mandrel and washed with 70% ethanol and then PBS. The tube maintained its compressed shape indicating shape preservation. The compression also made the tissue more compliant along the axis of the tube. Such compliant pericardial graft made from flat tissue such as, by way of example, and not limitation, pericardial tissue may be useful as peripheral, coronary and AV vascular graft or may be used to make stent graft. The tissue surface is expected to offer superior hemocompatibility or patency.

Example 30

Bioprosthetic Tissue Coated with Polyethylene Glycol Crosslinked with Gamma Radiation A 3 cm×3 cm piece is cut from a cleaned uncrosslinked bovine pericardial sac. The tissue is fixed by incubating in 0.2% glutaraldehyde solution for 7 days. The tissue is washed with PBS and then incubated for 30 minutes each in 20% ethanol, 40% ethanol, 80% ethanol, and finally in 100% ethanol. In a 500 ml beaker, 1 g polyethylene oxide molecular weight 100000 Daltons is dissolved in 20 ml chloroform. The ethanol-treated tissue is transferred into polyethylene oxide solution and incubated for 4 hours. The chloroform is removed by air drying. The polyethylene oxide-tissue composite is exposed to gamma radiation (Dose 0.1 to 4 Mrad) to crosslink polyethylene oxide. The crosslinked polyethylene glycol-tissue composite is incubated in PBS to rehydrate the collagen and polyethylene oxide polymer. The crosslinked polyethylene oxide and tissue composite patch is used as a wound dressing.

Example 31

Membrane Like Tissue Loaded with Drugs and Used as a Patch for Local Delivery

Bioprosthetic Tissue Incorporated with Water Insoluble Drugs

Porcine pericardial sac is obtained from a local abbotair and is cleaned to remove blood and fatty tissue from the surface. Ten 1 cm by 1 cm pieces are cut from the cleaned pericardial sac and then incubated for 30 minutes each in 20% ethanol, 50% ethanol and 70% ethanol, and finally 100 percent ethanol. The ethanol-treated tissue is then transferred to chlorhexidene acetate solution (30 percent solution in methanol) and incubated for 5 hours. The methanol is evaporated and the drug crystals are formed throughout the tissue matrix. When such tissue is implanted in an animal, it releases the drug in a controlled manner, possibly as a result of slow dissolution of drug crystals. A Teflon®-based release liner is applied on the tissue surfaces to reduce loss of drug crystals during routine handling, transportation and storage. The release liner is removed just prior to implantation.

In another variation of this approach, the tissue is first exposed to silver nitrate solution followed by exposing to sodium acetate solution. The exposure of silver nitrate solution inside the tissue matrix to sodium acetate solution forms silver acetate 'in situ' inside the tissue matrix. The deposited silver salts release silver ions and provide antimicrobial properties to the tissue. The silver salt deposition may be carried out in the operating room prior to implantation if silver salt, implantable tissue and appropriate salt solution such as, by way of example, and not limitation, sodium acetate, sodium chloride, sodium lactate are provided in a sterile manner and as a kit. The tissue used may be crosslinked (biostable) or uncrosslinked (biodegradable). The same method also could be used to deposit silver salts in collagen based products such as, by way of example, and not limitation, would dressings, collagen sponge products used for implantation etc. In another example, hydroxyapatite may be deposited or formed in the tissue matrix to make a hydroxyapatite-tissue composite matrix. The hydroxyapatite is added to the tissue matrix using methods known in the orthopaedic biomaterials art. In one embodiment, hydroxy apatite is synthesized inside the tissue matrix by combing calcium ion and phosphate ion solution in presence of tissue. The calcium nitrate [Ca(NO3)2, 4H2O, Aldrich], may be used as calcium source and ammonium hydrogen phosphate [(NH3)2HPO4, Aldrich] may be used as phosphorus source. The calcium nitrate solution is added to ammonium hydrogen phosphate solution at 40° C. while maintaining the pH using ammonium hydroxide to 10 and 10.6 to form hydroxyapatite crystals. The molar ratio of The Ca and P precursors is maintained 1.6 to make hydroxyapatite crystals. This reaction is carried in presence of tissue such as pericardial tissue so that hydroxyapatite is generated in side the tissue. The tissue-hydroxyapatite can potentially be used as a matrix for bone formation. If needed bone promoting bioactive compounds such as BMPs may be added in the composite matrix to accelerate the bone formation.

Example 32

Crosslinking of Tissues Using Unsaturated Acids 32a-1) Synthesis of Activated Unsaturated-Acids (n-Hydroxysuccinimide Ester)

Synthesis of Fumaric Acid n-Hydroxysuccinimide Ester (FUNHS) Using Acid Chloride Route.

8.2 g N-hydroxy succinimide (NHS) is transferred to 250 ml flask fitted with magnetic stirrer and nitrogen inlet. 200 ml dry benzene is transferred to the flask and about 50 ml of benzene is distilled off. The solution is cooled to 10° C. using an ice bath. 7.3 g triethylamine and 5.0 g fumaryl chloride are added dropwise to the NHS solution. The mixture is refluxed for 6 h under nitrogen atmosphere. At the end of a 6 h period, the solution is cooled and filtered to remove triethylamine hydrochloride. The filtrate is concentrated by removing the solvent under vacuum and the crude product is recovered. The product is further purified by column chromatography or recrystallization. The final product is stored under nitrogen atmosphere at −20° C. until further use.

32a-2) Synthesis of fumaric acid n-hydroxysulfosuccinimide ester (FUSNHS) Using 1,3-dicyclohexyl carbodiimide (DCC).

5 g fumaric acid is dissolved in 100 ml dry DMF. The solution is cooled to 4° C. 25.2 g 1,3-dicyclohexyl carbodiimide and 20.6 g of N-hydroxysulfosuccinimide are added to the reaction mixture. The mixture is stirred at 4° C. for 6 h and overnight at room temperature under nitrogen atmosphere. Dicyclohexylurea is removed by filtration and the fumaric acid NHS derivative is isolated by removing the DMF under vacuum and further purified by recrystallization or column chromatography. The product is stored under nitrogen atmosphere at −20° C.

32b) Modification and Crosslinking of Tissue Using Fumaric Acid n-Hydroxyscccinimide Ester (FUNHS).

Ten 1 cm by 1 cm bovine pericardium pieces, cut from a freshly obtained bovine pericardial sac, are transferred to 50 ml polypropylene centrifuge tube containing 10 ml phosphate buffered saline (PBS, (pH 7.2). 300 mg of fumaric acid succinimide ester (FUNHS) dissolved in 0.5 ml dimethyl sulfoxide is added to the tube and the solution is vortexed for 15 minutes. The modification reaction is carried for 6 hours at ambient temperature (25° C.) and then for 12 hours at 4° C. with gentle shaking. The reaction is terminated by washing the tissue with 20 ml PBS 3 times. Finally, the tissue is stored in 30 ml 40% HEPES buffered isopropanol solution. The tissue shows elevated shrink temperature as compared to untreated tissue indicating crosslinking of the tissue, presumably due to crosslinking introduced by a reaction with a bifunctional crosslinking agent. The crosslinks has polymerizable unsaturated group. The tissue is further crosslinked using free radical polymerizable monomer as described below:

32c) Additional Crosslinking of Fumaric Acid Modified Tissue Using Photopolymerization.

Two 1 cm by 1 cm pieces of fumaric acid crosslinked modified bovine pericardium tissue are incubated for 30 minutes each in 20% ethanol, 50% ethanol and 70% ethanol. 50 mg of 2,2-dimethoxy-2-phenylacetophenone (Irgacure 651, free radical photoinitiator) is dissolved in 1 ml n-vinyl pyrrolidinone to prepare a monomer solution. The 70% ethanol-incubated tissue is transferred to photoinitiator solution and incubated for 4 h at 25° C. and then for 12 h at 0° C. The tissue is removed from solution is placed on a glass plate and exposed to Black-Ray UV lamp (360 nm light, 10000 mW/cm2 intensity) for 5 minutes from each side. The crosslinked tissue is removed and washed with 10 ml PBS to remove unreacted monomer, initiator fragments and water soluble non-crosslinked polymer.

Example 33

Implantable Tissue Surface Modification and/or Crosslinking Using Reagents Capable of Undergoing Hydrogen Abstraction Reaction or Capable of Initiating Free Radical Polymerization a) Synthesis of Benzophenone Modified Polyethylene Glycol (BPEG)

A 3 necked 250 ml flask equipped with magnetic stirrer and nitrogen inlet is charged with 5 g 2-carboxyl benzophenone, 22 g polyethylene glycol, molecular weight 1000 and 100 ml dichloromethane (DCM). The solution is cooled to 4° C. and 6.5 g 1,3-dicyclohexyl carbodiimide (DCC) are added under nitrogen atmosphere. The mixture is stirred at 4° C. for 6 h and overnight at room temperature under nitrogen atmosphere. Dicyclohexylurea is removed by filtration and the benzophenone-terminated PEG ester is isolated by removing the DCM under vacuum. The PEG-benzophenone ester is further purified dissolving in toluene and precipitating in cold diethyl ether hexane.

b) Crosslinking/Surface Modification of Tissue Using by Hydrogen Abstraction Mechanism Two 1 cm by 1 cm pieces of bovine pericardium tissue samples are incubated for 30 minutes each in 20% ethanol, 50% ethanol and 70% ethanol and finally in 100% methanol. 200 mg benzophenone modified polyethylene glycol (crosslinker) is dissolved in 1.8 ml methanol. The methanol-incubated tissue is transferred to the crosslinker solution and incubated for 4 h at 25° C. and then for 12 h at 0° C. The tissue is removed from solution and the placed on a quartz glass plate and exposed to high intensity UV lamp (360 nm) for 15 minutes on each side. The crosslinked/PEG surface modified tissue is removed and washed with 10 ml ethanol to remove unreacted reagent.

Example 34

Chemical Modification of Tissue Using Benzophenone (Hydrogen Abstraction Moiety) and then Crosslinking Using UV Light a) Preparation of Protein Reactive Benzophenone Derivative (bezophenone n-hydroxysulfosuccinimide ester)

A 3 necked 250 ml flask equipped with magnetic stirrer and nitrogen inlet is charged with 5 g 2-carboxyl benzophenone, 5.2 g n-hydroxysulfosuccinimide (SNHS) and 100 dry dimethylformamide (DMF) are added. The solution is cooled to 4° C. and 6.5 g 1,3-dicyclohexyl carbodiimide (DCC) is added under nitrogen atmosphere. The mixture is stirred at 4° C. for 6 h and overnight at room temperature under nitrogen atmosphere. Dicyclohexylurea is removed by filtration and bezophenone SNHS ester is by isolated by removing the DMF under vacuum. The bezophenone SNHS ester is further purified by flash chromatography.

b) Tissue Modification Using Benzophenone SNHS Derivative.

Porcine pericardial sac is obtained from a local abbotair and is cleaned to remove blood and fatty tissue contaminants from the tissue surface. Ten 1 cm by 1 cm pieces are cut from the cleaned pericardial sac and are transferred to 10 ml PBS solution (pH 7.2). 0.5 g bezophenone SNHS is added to the buffered solution and the reaction is vortexed for 15 minutes and continued for 6 hours at ambient temperature. An additional 0.1 g benzophenone SNHS ester is added to the mixture at every 1.5 hours. After the reaction, the tissue is isolated and washed several times with PBS and ethanol solution finally with 100% methanol. The modified tissue is then immediately used in tissue modification reaction.

c) Crosslinking of Benzophenone Modified Tissue.

Two 1 cm by 1 cm pieces of benzophenone modified porcine pericardium tissue samples are incubated for 30 minutes each in 20% ethanol, 50% ethanol, 70% ethanol, and finally in 100% methanol. The tissue is removed from solution is placed on a quartz glass plate and exposed to UV lamp for 5 minutes from each side. The crosslinked/PEG surface modified tissue is removed and washed with 10 ml ethanol to remove unreacted reagent.

Example 35

Bioprosthetic Tissue Based Adhesive Patch for Surgical Applications

Use of Membrane Like Implantable Tissue to Make a Surgical Adhesive Patch

Bovine pericardial sac is obtained from a local abbotair and is cleaned to remove blood and fatty tissue contaminants from the tissue surface. 2 cm by 5 cm size pieces are cut from the cleaned pericardial sac. Separately a photopolymerizable adhesive solution is prepared from polyethylene glycol 400 diacrylate (PEG400DA monomer). Photoinitiator (Eosin 0.02% and triethanol amine 0.5%) is dissolved in the PEG400DA monomer liquid and this solution is applied on the pericardial tissue strip. The monomer coated/incubated tissue serves as an adhesive patch. The adhesive coated patch is applied and conformed to the tissue geometry on a surgical site such as, by way of example, and not limitation, air-leaking lung tissue. The patch is applied in such a way that the liquid adhesive layer is between the pericardial tissue and lung tissue. The liquid adhesive is cured or photopolymerized by argon ion laser or xenon light emitting at 514 nm light. The green light passes through the pericardial tissue and initiates the polymerization of PEGDA. The polymerized PEGDA adheres to the lung and pericardial tissue. If needed, the patch may also be immobilized by suturing on the lung tissue. The cured layer of PEGDA prevents air leak from the air tissue. If an absorbable patch is desired, then degradable implantable tissue (for example uncrosslinked bovine pericardial tissue) may, for example, and without limitation, be used along with absorbable surgical adhesive such as, by way of example, and not limitation, FocalSeal® marketed by Genzyme Biosurgery or DuraSeal™ surgical adhesive marketed by Confluent Surgical Inc. Other surgical adhesives such as cynoacrylate based adhesives may also be used.

Example 36

Radio-Opaque Implantable Tissue

Tissue Modification Using Iodinated Compound
a) Synthesis of N-Hydroxysuccinimide Ester of Triiodobenzoic Acid (TIBA-NHS)
1.2 g n-hydroxy succinimide and 1.1 g of triethyl amine are dissolved in 100 ml benzene. The solution is cooled to 0° C. in ice bath. 1.2 g triiodobenzoyl chloride is added dropwise to the cold alcohol solution. The mixture is then refluxed under nitrogen atmosphere for 3 h. The solution is filtered to remove triethylamine hydrochloride. The ester is then isolated by removing the solvent. It is further purified by column chromatography.
b) Chemical Bonding of Triiodobenzoic Acid Derivative to the Tissue.
Modification of Bovine Pericardium Tissue.
Ten 1 cm by 1 cm bovine pericardium pieces, cut from a freshly obtained bovine pericardial sac, are transferred to 50 ml conical flask containing 10 ml phosphate buffered saline (PBS, (pH 7.2). 250 mg triiodobenzoic acid succinimide ester, TIBA-NHS ester dissolved in 0.5 ml dimethyl sulfoxide is added to the tube and the solution is vortexed for 15 minutes. 0.1 g of TIBA-NHS in 0.1 ml DMSO is added to the fixation solution every 2 hours up to six hours. The modification reaction is carried for 6 hours at ambient temperature (25° C.) and then for 12 hours at 4° C. with gentle shaking. The reaction is terminated by washing the tissue with 20 ml PBS 3 times. Finally, the tissue is stored in 30 ml 38% isopropanol and 2% benzyl alcohol solution at 4° C. until further use. The triiodobenzoic acid moieties incorporated in the tissue makes the tissue radio-opaque when viewed using medical x-ray imaging techniques.
Alternatively radio-opaque compounds such as, by way of example, and not limitation, iohexyl, metrizamide, iopamidol, iopentol, iopromide, and Ioversol are added in the tissue coating formulations mentioned above. For example, Metrizamide 0.2 g and polylactic acid (0.8 g, molecular weight 50000) are dissolved in 10 ml chloroform and the polymer solution is spray-coated or dip-coated on the tissue surface. The solvent is removed by vacuum drying. The Metrizamide trapped inside the tissue coating makes the tissue radio-opaque when viewed using medical x-ray imaging technique.
Radio-opaque tissue is also made by treating the tissue with commercially available x-ray contrast agents such as, by way of example, and not limitation, Iohexyl or Ioversol in presence of EDC as a catalyst and n-hydroxysuccinimide as a cocatalyst. The reaction is performed at pH 6.5 using PBS or other suitable buffers.
Tissue may also be crosslinked using a crosslinker containing radio-opaque groups such as, by way of example, and not limitation, triiodobenzene moieties.

Example 37

Crosslinking of Tissue Using Free Radical Polymerizable Monomers

Tissue Fixation Using Glycidyl Methacrylate and Subsequent Free Radical Photopolymerization Using Free Radical Polymerizable Monomers Step 1
Treatment of Bovine or Sheep Pericardial Tissue with Glycidyl Methacrylate.
Five pieces of unfixed tissue are attached to circular immobilization 28 mm diameter ring clamps. The clamped tissues are suspended in 500 ml beaker containing 200 ml PBS, 25 ml glycidyl methacrylate and 25 ml triethyl amine. The solution was stirred for 16 hours using magnetic needle stirrer. The beaker was transferred to a water bath maintained at 50° C. and kept there for 4 hours. The tissue was then removed from the clamps washed with PBS and used in next step for treatment with free radical polymerizable monomer and subsequent polymerization and crosslinking.
Step-2
Fixation of Glycidyl Methacrylate Treated Tissue Using Free Radical Polymerization.
Fixation Using Free Radical Photopolymerization.
One piece of glycidyl methacrylate treated tissue was incubated in 15 ml of 70% isopropyl alcohol solution for half an hour in a glass tube. The tissue was then transferred to 2 ml n-vinyl pyrrolidinone solution containing 40 mg 2-2 dimethoxy-2 phenyl acetophenone as a free radical long ultraviolet light photoinitiator and incubated for 1 hour at ambient temperature (25-30° C.). Care was taken to completely expose all surfaces of the tissue to monomer solution during incubation. The tissue was removed from the monomer solution and then placed on glass plate. The tissue was then exposed to long wavelength ultraviolet light (Black-Ray UV lamp, 360 nm flood light, 10000 mW/cm2 intensity) at a distance of 10 cm for 5 min from both sides. The fixed tissue was then washed with PBS and stored in alcohol solution until further use. Using a similar procedure to that described above, tissue was treated with acrylic acid monomer instead of vinyl pyrrolidinone monomer.

Example 38

Modification of Tissue or Collagen by Cyclic Lactone Polymerization

Preparation of Tissue-Hydroxyacid or Collagen-Polyhydroxyacid Copolymer
a) Modification of Tissue or Collagen Sponge by Cyclic Lactone (dl-lactide)
Three 2 cm×2 cm piece is cut from a cleaned uncrosslinked bovine pericardial sac. The tissue pieces are incubated for 30 minutes each in 100% acetone. The dried tissue is then transferred into 100 ml flask. The tissue is further dried at 50° C. under vacuum for 10 hours and weighed. 10 ml tetrahydrofuran (THF), 3.0 g of dl-lactide and 100 mg of stannous octoate are charged into the flask. The solution is refluxed for 24 hours to promote cyclic polymerization of lactide by hydroxyl groups of tissue proteins (hydroxy proline). At the end of the reaction, tissue is removed, washed with methylene chloride to remove lactide monomer and unbound polylactide polymer. The tissue is dried and weighed. The increase in weight is attributed to polylactide chemically bound to the tissue matrix. A similar reaction can be carried out on the lyophilized commercially available collagen sponge from Knesey Nash or glutaraldehyde fixed pericardial tissue. Other cyclic lactone monomers such L-lactide, caprolactone, glycolide, trimethylene carbonate, dioxanone may also be polymerized or copolymerized in place of lactide using a similar method mentioned above.

Example 39

Modification of Proteins Using Cyclic Lactones

A 100 ml round bottom flask is flame-dried under vacuum for 2 hours. 2 g of pharmaceutical grade gelatin is then transferred the flask. The gelatin is further dried at 50° C. under vacuum for 10 hours and weighed. 10.0 gram of dl-lactide and 100 mg of stannous octoate are charged into the flask. The flask is then heated in an oil bath at 120° C. for 24 hours. The flask is cooled and 20 ml chloroform is added to the flask. The product is incubated in chloroform for 3 hours to remove monomer and unbound dl-lactide from the product. The solvent is removed and the gelatin-lactide copolymer is dried under vacuum and weighed. Other proteins or glycosaminoglycans such as, by way of example, and not limitation, albumin, elastin, fibrinogen, collagen or hyaluronic acid may also be used in place of gelatin. Other cyclic lactone monomers such L-lactide, caprolactone, glycolide, trimethylene carbonate, dioxanone may also be polymerized or copolymerized in place of lactide using a similar method mentioned above.

Alternatively, gelatin may also be reacted with hydroxy acids such a lactic acid in water at 100° C. to form a copolymer.

Example 40

Preparation of Tissue with Biostable and Biodegradable Regions with Controlled Geometry Bovine pericardium (BP) tissue pieces (approximately 25 mm dia, 3 pieces) are cut from a fresh pericardium and transferred to a 100 ml flask containing 10 ml PBS, 1.25 ml triethylamine (TEA) and 1.25 ml glycidyl methacrylate (GM). The solution was heated to 50° C. with constant stirring using magnetic stir bar and held there for 8 hours. The tissue strips are removed from the solution and washed with PBS, distilled water, & incubated in 70% isopropanol solution in water for 30 minutes. Finally, strips are then transferred to 10 ml vinyl pyrrolidinone monomer solution containing 500 ppm 2,2-dimethoxy 2-phenyl acetophenone (photoinitiator) and incubated at room temperature (30° C.) for one hour. One vinyl pyrrolidinone-infused sample piece was transferred on a glass plate. An aluminum foil (8 mm diameter, 250 micron thick) was placed at the center of the monomer-infused tissue. The tissue was then exposed to 360 nm light (Black-Ray UV lamp, 360 nm flood light, 10000 mW/cm2 intensity at a distance of 10 cm) for 5 minutes to polymerize the vinyl pyrrolidinone monomer and crosslink the tissue. The same treatment was repeated using aluminum foil from the other side of the tissue. The exposed tissue was removed and washed with PBS and 70% isopropanol to remove unreacted monomer, uncrosslinked polymer and initiator fragments. The uncrosslinked regions where light could not penetrate due to aluminum foil and initiate photopolymerization was visually noticeable and had different "feel" to the human hand when compared to crosslinked or light exposed tissue. Using a similar method to that described above, another piece of the vinyl pyrrolidinone infused tissue was covered with aluminum foil (arrow shape, 8 mm long and 3 mm thick) and the exposed to polymerization and crosslinking using 360 nm light for 5 minutes. The tissue under aluminum foil can be considered as dark control tissue as discussed previously where no polymerization and crosslinking occurred. The arrow-imprinted tissue was subjected to pepsin digestion for 48 hours. After 48 hours of treatment with pepsin, the dark control tissue (in the shape of arrow) was completely digested by the enzyme while light exposed or crosslinked tissue remained completely intact or stayed biostable. This observation was confirmed in vivo by implanting the arrow-shaped imprinted tissue in a rat subcutaneous cavity for 60 days. After 60 days, the dark control area of the tissue was (unfixed tissue) substantially or completely digested by natural protease enzymes present in the animal body and an arrow-like digested area was clearly visible to the naked eye on explanted samples. It is understood that a variety of geometries and shapes may be created inside the tissue by using various masks to block the light similar to photolithography technique used in semiconductor processing art. Other techniques such as, by way of example, and not limitation, electron beam irradiation or scanning of 360 nm laser light on selected areas may also be used to create a pattern inside the tissue similar to principles used in electron beam lithography. In that case, a mask may not be necessary to create a pattern (i.e., the beam itself can create a pattern).

Example 41

Membrane Like Thin and/or Large Tissue Obtained Using Tissue Engineering Art for Bioprosthesis Applications a) Engineering a Tissue from as Scaffold 5 cm×5 cm size porous collagen tissue engineering scaffold obtained from Knesey Nash is soaked in 70% ethanol (overnight) to sterilize the scaffold, washed with sterile PBS (15 minutes, 3 times) and soaked in Minimum Essential Medium (MEM) supplemented with aminoacids, antibiotics and 30% fetal bovine serum (FBS) for 1.5 h. The scaffold is then transferred to a sterile tissue culture dish. Human smooth muscle cells or fibroblast cells passaged in MEM/10% FBS are resuspended in MEM/10% FBS and approximately 200000 cells per square inch are carefully placed on the scaffold. The cells are allowed to adhere for 30 minutes before adding 0.75 ml of the same medium to each sample. After 24 hours of incubation in a 5% carbon dioxide atmosphere at 98% humidity and 37° C., the samples are transferred to new wells and fresh medium and cells are added to the scaffold. The addition of cells and media and incubation is continued until a desired tissue thickness is achieved (1 to 2000 microns). For large size tissue, a large scaffold is used.

Porous tissue engineering scaffolds known in the tissue engineering art based on polyesters such as polylactide or polyglycolide or their copolymers. Natural scaffolds such as porcine sub-mucosa tissue may also be used in some cases to obtain a desired tissue engineered tissue.

The generated may be decellularized and used in bioprosthesis manufacturing. The tissue may be crosslinked or modified using glutaraldehyde, EDC and other methods known in the art or methods described in this invention prior to using it in bioprosthesis use.

In one embodiment of the present invention the composition of matter produced includes an uncrosslinked biological tissue, wherein the tissue is chemically modified with unsaturated polymerizable groups.

In another embodiment of the present invention the composition of matter produced includes a biological tissue modified with unsaturated groups, wherein the unsaturated groups are used in chemical crosslinking of the tissue.

In yet another embodiment of the present invention, the composition of matter produced includes biological tissue modified with unsaturated groups, wherein a cross-linked biological tissue is produced by treating the tissue under effective cross-linking condition comprising a free radical initiator or photoinitiator. In one embodiment, the crosslinking is done in presence of a mono- or polyunsaturated compound capable of copolymerizing with the unsaturated groups in the tissue.

In an alternate embodiment of the present invention, the composition of matter produced includes a biological tissue modified with unsaturated groups, wherein unsaturated groups are copolymerized with free radical polymerizable comonomers. The comonomers may include, but are not limited to, functional monomers with reactive functional groups such as, by way of example, and not limitation, epoxide or isocyanate; monomers with charged groups; monomers that undergo crosslinking and biodegradation; monomers that produce thermosensitive polymers; monomers with long alkyl chains; monomers that produce crystalline or semicrystalline polymers; monomers that produce functional polymers upon hydrolysis such as, by way of example, and not limitation, polyvinyl alcohol; monomers with radio-opaque moieties; monomers that produce elastomers, monomers that have phosphorylcholine groups, and fluorinated monomers In yet an alternate embodiment of the present invention, the composition of matter produced includes a biological tissue modified and crosslinked with unsaturated groups, wherein modified unsaturated groups and/or crosslinks with unsaturated groups are copolymerized with free radical polymerizable comonomers.

In another alternate embodiment of the present invention, the composition of matter produced includes a biological tissue modified with unsaturated groups, wherein unsaturated groups are copolymerized with free radical polymerizable comonomers having biodegradable or hydrolizable groups. The biodegradable monomers may be hydrophilic or hydrophobic.

In one embodiment of the present invention, a cross-linked biological tissue is produced by treating the tissue under effective cross-linking conditions with a biodegradable crosslinker. In some embodiments, the biodegradable crosslinker may be a solute in a fluid including a solvent.

In yet another alternate embodiment of the present invention, the composition of matter produced includes a biological tissue modified with unsaturated groups, wherein a cross-linked biological tissue is produced by treating the unsaturated group-modified tissue under effective cross-linking conditions with an organic di- or poly-mercapto compounds. In one embodiment, the di- or poly-mercapto organic compound may be a solute in a fluid comprising a solvent.

In an alternate embodiment of the present invention, the composition of matter produced includes a membrane-like biological tissue and a surgical adhesive. The membrane-like tissue and surgical adhesive are formulated to form a "surgical adhesive patch". Though not required, the surgical adhesive patch may be biodegradable in some applications.

In another embodiment of the present invention, the composition of matter produced includes a radio-opaque implantable animal tissue.

In an embodiment of the present invention, the biological tissue produced has shape memory properties In yet another embodiment of the present invention, certain parts or regions of the biological tissue are made biostable while the remaining parts of the tissue are made biodegradable. The biostable and biodegradable regions within the tissue can be of any geometry.

In another embodiment of the present invention, a non-crosslinked degradable biological tissue is produced by treating the tissue under effective treatment conditions with a monofunctional reagent capable of reacting with primary amine groups on the tissue. In one embodiment, the monofunctional reagent may be a polyether derivative or an activated acid derivative such as, by way of example, and not limitation, an n-hydroxysuccinimide derivative, a cyclic lactone such as, by way of example, and not limitation, glycolide or lactide, an isocyanate derivative, or an anhydride derivative.

In one embodiment of the present invention, a biostable or biodegradable tissue produced by treating the tissue under effective treatment conditions with a cyclic lactone to produce a tissue-polylactone graft copolymer.

In another embodiment of the present invention a biological tissue is produced in which the biological tissue/synthetic biodegradable polymer composite is produced by treating the tissue with a fluid comprising synthetic biodegradable polymer.

In another embodiment of the present invention a biological tissue is produced in which the biological tissue/synthetic biodegradable polymer composite comprises a synthetic biodegradable polymer, which is chemically bonded to the biological tissue.

In one embodiment of the present invention a degradable biological tissue/synthetic biodegradable polymer composite produced by treating a non-crosslinked tissue under effective treatment conditions with a synthetic biodegradable polymer. In one embodiment, the synthetic biodegradable polymer is polylactone or polyhydroxyacid derivative in a fluid comprising a solvent. The synthetic biodegradable polymer can also be a crosslinked polymer.

In an alternate embodiment of the present invention the biological tissue is produced by treating the tissue with a fluid comprising synthetic biodegradable polymer and a bioactive compound.

In an alternate embodiment of the present invention, a method for cross-linking a tissue, which method may be utilized for tissue fixation is achieved by steps that include, without limitation, linking at least a portion of the free radical polymerizable groups on the tissue with a covalent bond and crosslinking the free radical polymerizable groups using free radical mechanism or cyclic dimerization (e.g., treating the tissue under effective crosslinking conditions with a compound having a free radical polymerizable group). In another embodiment of the present invention, a method of modifying a protein or mixture of proteins in the solid state is achieved by steps that include, without limitation, covalently bonding at least a portion of the protein functional groups with a free radical polymerizable group in a solid state; and treating the protein under effective cross-linking conditions with a compound having a free radical polymerizable group.

In an yet another alternate embodiment of the present invention, a method for cross-linking a tissue, which method may be utilized for tissue fixation is achieved by steps that include, without limitation, covalently linking compounds containing at least one free radical polymerizable group on the tissue and crosslinking the free radical polymerizable group(s) using a di- or poly-mercapto organic compounds. In one embodiment, the method comprises covalently bonding at least a portion of the tissue functional groups with unsaturated groups and treating the tissue under effective cross-linking conditions with a di- or polymercapto compound.

In an alternate embodiment of the present invention, a method for cross-linking a tissue, which method may be utilized for tissue fixation, is achieved by steps that include, without limitation, covalently bonding at least a portion of the tissue functional groups with at least one free radical polymerizable group and treating the tissue under effective crosslinking conditions with a compound having a free radical group and a biodegradable link. In one embodiment, the method comprises crosslinking the tissue with compounds containing at least one free radical polymerizable group and further crosslinking the free radical polymerizable group using free radical chemistry such as, by way of example, and not limitation, free radical dimerization and polymerization, free radical crosslinking or free radical copolymerization with monomer.

In an alternate embodiment of the present invention, the method for making a biodegradable biological tissue includes the steps of, without limitation, treating the tissue under effective cross-linking conditions with a fluid comprising a biodegradable crosslinker.

In one embodiment of the present invention, the method for incorporating a biodegradable polymer in a biological tissue is achieved by steps that include, without limitation, dehydrating the biological tissue; treating the dehydrated tissue with a solution of biodegradable polymer in an organic solvent; and removing the solvent from the treated tissue.

In yet another embodiment of the present invention, the method for incorporating a biodegradable polymer and a bioactive compound in an implantable biological tissue is achieved by steps that include, without limitation, dehydrating the biological tissue; treating dehydrated tissue with a solution of biodegradable polymer and bioactive compound in an organic solvent; and removing the solvent from the treated tissue. In an alternate embodiment, the method comprises the steps of providing a tissue suitable for human implantation; exposing the tissue to a fluid comprising sparingly soluble drug dissolved in a solvent; and evaporating the solvent.

In an alternate embodiment of the present invention, the biological tissue based controlled drug delivery patch that releases at least one bioactive compound.

In an alternate embodiment of the present invention, the method for making an implantable degradable drug delivery patch from the membrane-like tissue is achieved by steps that include, without limitation, dehydrating the membrane-like biological tissue; treating dehydrated membrane-like tissue with a solution of biodegradable polymer and a bioactive compound in an organic solvent; removing the solvent from the treated tissue; releasing the compound from the biodegradable polymer. In an alternate embodiment, the method comprises providing a implantable membrane-like animal tissue; exposing the tissue to a fluid comprising controlled release carrier and a bioactive compound dispersed in the solvent; and evaporating the solvent. The bioactive compound may be a cell cycle inhibitor including, but not limited to, Lovastatin (HMG-CoA inhibitor or statin), paclitaxel, and Rapamycin. The biodegradable polymer may be hydrophobic or hydrophilic. The biodegradable polymer can be a crosslinked polymer, though not required.

In an alternate embodiment of the present invention, the method for coating the biological tissue with biodegradable polymer (e.g., forming a coated tissue or tissue implant) is achieved by steps that include, without limitation, providing a tissue suitable for human implantation; coating the tissue surface by spraying a solution comprising a solvent and a polymer dissolved in the solvent; and evaporating the solvent. In an alternate embodiment, the method further comprises the steps of providing a tissue suitable for human implantation; exposing the tissue to a fluid comprising biodegradable polymer dispersed in the solvent; and evaporating the solvent. In one embodiment, the method comprises the steps of providing a tissue suitable for human implantation; coating the tissue surface by spraying a solution comprising precursors capable of forming crosslinked polymers; and crosslinking the precursors. In another alternate embodiment, the method comprises the steps of providing a tissue suitable for human implantation; coating the tissue surface by spraying a macromonomer solution; and crosslinking the macromonomer in the solution. In one exemplary embodiment, the method comprises dehydrating the biological tissue; spraying a coating solution comprising biodegradable polymer in a solvent; and removing the solvent from the treated tissue. In an alternate embodiment, the method comprises dehydrating the biological tissue; dipping the dehydrated tissue in a coating solution comprising biodegradable polymer in a solvent; removing the solvent from the treated tissue.

In another embodiment of the present invention, a method for making a radio-opaque implantable tissue is achieved by steps that include, without limitation, treating a biological tissue with a radio-opaque compound under effective treatment conditions to covalently bond the radio-opaque compound to the tissue. In some embodiments, the radio-opaque compound is an iodinated organic compound.

In another embodiment of the present invention, a method for making a radio-opaque implantable tissue is achieved by steps that include, without limitation, treating a biological tissue with a radio-opaque compound and biodegradable polymer in a solvent and removing the solvent to produce a tissue coated with biodegradable compound and radio-opaque compound.

Another embodiment of the present invention provides for a method of treating a tissue under effective cross-linking conditions with a di- or poly-mercapto organic compound.

In one embodiment of the present invention, a method of coating a biological implantable tissue with a biodegradable hydrogel is achieved by steps that include, without limitation, treating a tissue with a precursor or biodegradable hydrogel components and crosslinking the precursors to produce a biodegradable hydrogel coating on the surface of the tissue.

In another embodiment of the present invention, a method of coating a biological implantable tissue with biodegradable hydrogel comprising cells/bioactive compound is achieved by steps that include, without limitation, treating a tissue with a precursor or biodegradable hydrogel components comprising cells and/or bioactive compounds and crosslinking the precursors to produce a biodegradable hydrogel coating with entrapped cells/drug in the coating on the surface of the tissue.

In yet another embodiment of the present invention, a method of coating a biological tissue with non-crosslinked biodegradable hydrogel is achieved by steps that include, without limitation, dehydrating the biological tissue; treating the dehydrated tissue with a solution of biodegradable polymer in an organic solvent; removing the solvent from the treated tissue; and exposing the tissue to a biological environment to hydrate the tissue and biodegradable polymer.

In another embodiment of the present invention, a method for incorporating a biodegradable polymer and bioactive substance in a biological tissue is achieved by steps that include, without limitation, forming grooves or holes on tissue surface; filling the grooves or holes with a biodegradable polymer and bioactive compound; and releasing the bioactive compound in a controlled manner.

In an alternate embodiment of the present invention a degradable animal tissue is coated with or incorporated with, Demineralized Bone Matrix (DBM) and/or purified bone morphogenic proteins (BMP). This mixture provides a matrix that allows the cellular components of the body to migrate into it and thus produce osteoinduction where needed. The matrix composition, enzymes (such as, by way of example, and not limitation, thrombin and plasmin), BMPs, growth factors and DBM and their concentrations, calcium salts such as, by way of example, and not limitation, calcium phosphates may be adequately formulated to optimize the longevity of this temporal scaffolding structure and the osteoinduction which needs to occur. All of the animal tissue components are biodegradable, but during osteogenesis the mixture provides a non-collapsible scaffold that can determine the shape and location of the newly formed bone.

In one embodiment of the present invention the composition of matter produced comprises a degradable tissue coated with a biodegradable polymer comprising at least one growth factor and/or a drug.

In another embodiment of the present invention, the composition of matter including a biodegradable implantable animal tissue coated with biodegradable polymer and an effective concentration of at least one growth factor, wherein the concentration of growth factor is effective in promoting wound healing.

An alternate embodiment of the present invention provides for a composition of matter that promotes the growth of cells, including a degradable animal tissue; a hydrogel coating on the surface of degradable tissue; and an effective concentration of at least one growth factor, wherein the concentration of the growth factor is effective in promoting the directed migration of the animal cells. In another embodiment, genetically altered cells and/or other cells may also be included in the tissue-coated hydrogels of this invention.

In one embodiment of the present invention, a composition of matter that promotes the proliferation and/or differentiation of animal cells is made by including an implantable animal tissue; a hydrogel; and an effective concentration of at least one growth factor, wherein the concentration is effective in promoting proliferation and/or differentiation of animal cells.

In an alternate embodiment of the present invention, the composition of matter produced is used to promote the localized delivery of at least one growth factor. Exemplary, but not limiting, growth factors are vascular endothelial growth factor (VEGF) or BMP or mixtures thereof. The use of numerous other growth factors, both known and yet to be discovered, will be readily apparent to one skilled in the art, in light of the teachings of the present invention.

One embodiment of the present invention provides for a process for promoting the healing of wounds, which is achieved by steps that include, without limitation, applying to the wound a composition that contains a non-crosslinked animal degradable animal tissue modified with a synthetic polymer and an effective concentration of at least one growth factor or one small molecule therapeutic, wherein the concentration is effective to promote wound healing.

In one embodiment of the present invention, a degradable implantable animal tissue-based composition produced is used to promote the localized delivery of a poorly water-soluble form of a bioactive compound, such as, but not limited to, chlorhexidene; chlorhexidene diacetate monohydrate or chlorhexidene dihydrochloride; chlorhexidene gluconate, silver salts such as, by way of example, and not limitation, silver chloride, silver iodide, silver acetate, silver lactate, cell cycle inhibitors such as, by way of example, and not limitation, paclitaxel, lovastatin, rapamycin, sinvastatin, rifampin; or anti-arrhythmic agents such as, by way of example, and not limitation, amiodarone.

In another embodiment of the present invention, the method for tissue crosslinking or fixation is achieved by steps that include, without limitation, linking the free radical polymerizable groups on the tissue with a covalent bond and crosslinking the free radical polymerizable groups using free radical polymerizable monomers including a primary amine group. Further crosslinking the primary amine groups using a di- or polyfunctional crosslinker such as, by way of example, and not limitation, glutaraldehyde.

In one embodiment of this of invention a bioprosthesis made using membrane like tissue is provided wherein the membrane like tissue is made using tissue engineering methodologies and has a thickness from 10 micron to 2000 microns and/or has a size >1 square inch.

In an alternate embodiment of the present invention, the method for making a degradable tissue matrix is achieved by steps that include, without limitation, substantially water-insoluble drug or bioactive compound is provided for in an alternate embodiment of the present invention. The method includes dehydrating the membrane-like biological tissue; treating dehydrated membrane-like tissue with a solution of a substantially water-insoluble bioactive compound in an organic solvent; and removing the solvent from the treated tissue.

Having fully described at least one embodiment of the present invention, other equivalent or alternative implantable tissue composition and methods will be apparent to those skilled in the art. The invention has been described above by way of illustration, and the specific embodiments disclosed are not intended to limit the invention to the particular forms disclosed. The invention is thus to cover all modifications, equivalents, and alternatives falling with the spirit and scope of the following claims.

The invention claimed is:

1. A method for forming a composite material of a tissue and synthetic biodegradable polymer, the method comprising:
    selecting a tissue suitable for implantation into a patient;
    infusing the tissue in vitro with a fluid that comprises an organic solvent and the synthetic biodegradable polymer dissolved in the fluid; and
    evaporating the fluid that comprises the solvent;
    wherein the polymer comprises a plurality of polymer functional groups that form covalent bonds with tissue functional groups in the tissue.

2. The method of claim 1 wherein the biodegradable polymer has a molecular weight from about 2000 to about 500000 Daltons and comprises a polyhydroxy acid, a polylactone, a polyhydroxyalkanoate, a polyanhydride, a polyglycolide, a poly(orthocarbonate), a poly(carbonate), or a poly(phosphonate).

3. The method of claim 1 wherein the organic solvent comprises alcohol, acetone, tetrahydrofuran, benzene, toluene, xylene, chloroform, methylene chloride, dimethyl sulfoxide, n-vinyl pyrrolidinone, or dimethylacetamide.

4. The method of claim 1 wherein the tissue is crosslinked.

5. The method of claim 1 wherein the biodegradable polymer further comprises an unsaturated group at the time of the infusion.

6. The method of claim 5 wherein the unsaturated groups are activated by free radicals, with some of the unsaturated groups reacting with the tissue and some of the unsaturated groups reacting with each other to form links within the tissue.

7. The method of claim 5 wherein unsaturated groups are cross-linked with organic di-mercapto or poly-mercapto compounds that are present in the fluid that is infused with the tissue.

8. The method of claim 5 wherein the unsaturated groups comprise acrylamide, methacrylamide, acrylate or methacrylate.

9. The method of claim 1 wherein the biodegradable polymer comprises polyethylene glycol.

10. The method of claim 1 wherein the fluid further comprises a bioactive substance.

11. The method of claim 1 wherein the tissue functional groups are amines, carboxylic acids, hydroxyls, or thiols that react with the biodegradable polymer functional groups.

12. The method of claim 1 wherein the polymer functional groups are activatable to react, at pH 7.2 at room temperature, with amine groups or thiol groups.

13. The method of claim 12 wherein the polymer functional groups comprise succinimidyl moieties.

14. The method of claim 1 wherein the tissue is chosen from the group consisting of ureter, artery, pericardial, intestinal, submucosa, cornea, and meniscus.

* * * * *